US008232285B2

(12) United States Patent
Liu et al.

(10) Patent No.: US 8,232,285 B2
(45) Date of Patent: Jul. 31, 2012

(54) QUINAZOLINONE COMPOUNDS AND METHODS OF USE THEREOF

(75) Inventors: Jifeng Liu, Winchester, MA (US); Syed M. Ali, North Andover, MA (US); Mark A. Ashwell, Carlisle, MA (US); Ping Ye, Lexington, MA (US); Yousheng Guan, North Billerica, MA (US); Shi-Chung Ng, San Diego, CA (US); Rocio Palma, North Andover, MA (US); Dan Yohannes, Cambridge, MA (US)

(73) Assignee: ArQule, Inc., Woburn, MA (US)

( * ) Notice: Subject to any disclaimer, the term of this patent is extended or adjusted under 35 U.S.C. 154(b) by 1077 days.

(21) Appl. No.: 12/142,762

(22) Filed: Jun. 19, 2008

(65) Prior Publication Data

US 2009/0130097 A1 May 21, 2009

Related U.S. Application Data

(60) Provisional application No. 60/945,838, filed on Jun. 22, 2007.

(51) Int. Cl.
A01N 43/54 (2006.01)
A61K 31/517 (2006.01)
C07D 401/00 (2006.01)
C07D 403/00 (2006.01)
C07D 413/00 (2006.01)
C07D 417/00 (2006.01)
C07D 419/00 (2006.01)
C07D 239/72 (2006.01)

(52) U.S. Cl. ......... 514/266.21; 514/266.23; 514/266.24; 514/266.3; 544/284; 544/287

(58) Field of Classification Search .................. None
See application file for complete search history.

(56) References Cited

U.S. PATENT DOCUMENTS

| 3,723,432 A | 3/1973 | Ott ........................ 260/251 QB |
| 3,925,548 A | 12/1975 | Oh ................................ 424/251 |
| 4,522,811 A | 6/1985 | Eppstein et al. .................... 514/2 |
| 4,981,856 A | 1/1991 | Hughes ........................... 514/259 |
| 5,037,829 A | 8/1991 | Fryne et al. .................... 514/259 |
| 5,057,614 A | 10/1991 | Davis et al. .................... 548/466 |
| 5,147,875 A | 9/1992 | Coates et al. .................. 514/259 |
| 5,187,167 A | 2/1993 | Hughes ........................... 514/259 |
| 5,280,027 A | 1/1994 | Andrew et al. ................. 514/259 |
| 5,292,747 A | 3/1994 | Davis et al. .................... 514/285 |
| 5,380,746 A | 1/1995 | Barth et al. .................... 514/414 |
| 5,516,915 A | 5/1996 | Barth et al. .................... 548/455 |
| 5,545,636 A | 8/1996 | Heath, Jr. et al. ............. 514/214 |
| 5,559,228 A | 9/1996 | Gillig et al. .................... 540/460 |
| 5,591,842 A | 1/1997 | Kojiri et al. ................... 536/27.1 |
| 5,591,855 A | 1/1997 | Hudkins et al. ................. 546/256 |
| 5,721,230 A | 2/1998 | Harris et al. ................... 514/214 |
| 5,721,245 A | 2/1998 | Davis et al. .................... 514/294 |
| 5,747,498 A | 5/1998 | Schnur et al. ................... 514/259 |
| 5,773,476 A | 6/1998 | Chen et al. ..................... 514/620 |
| 5,856,517 A | 1/1999 | Hurnyn et al. .................. 548/455 |
| 5,859,261 A | 1/1999 | Faul et al. ...................... 548/466 |
| RE36,736 E | 6/2000 | Davis et al. .................... 548/466 |
| 6,153,641 A | 11/2000 | Bergstrand et al. ........... 514/414 |
| 6,184,377 B1 | 2/2001 | Gao ............................. 544/234 |
| 6,524,832 B1 | 2/2003 | Kufe et al. ................. 435/173.1 |
| 6,867,198 B2 | 3/2005 | Al-Awar et al. ................ 514/44 |
| 6,900,221 B1 | 5/2005 | Norris et al. ................. 514/266.4 |
| 7,070,968 B2 | 7/2006 | Kufe et al. ................. 435/173.1 |
| 7,501,430 B2 | 3/2009 | Lapierre et al. ............... 514/275 |
| 2003/0091639 A1 | 5/2003 | Jiang et al. .................... 424/486 |
| 2004/0071775 A1 | 4/2004 | Jiang et al. .................... 424/486 |
| 2006/0251734 A1 | 11/2006 | Kufe et al. ................. 435/173.1 |

FOREIGN PATENT DOCUMENTS

| EP | 0056637 | 1/1982 |
| EP | 0384349 A1 | 8/1990 |
| EP | 0397060 A2 | 11/1990 |
| EP | 0397060 B1 | 11/1990 |
| EP | 0884319 B1 | 3/1993 |
| EP | 0825190 | 2/1998 |
| EP | 1120414 | 8/2001 |
| WO | WO 91/13070 | 9/1991 |
| WO | WO 91/13071 | 9/1991 |
| WO | WO 93/18765 | 9/1993 |
| WO | WO 95/17182 | 6/1995 |
| WO | WO 95/30682 | 11/1995 |
| WO | WO 96/06616 | 3/1996 |
| WO | WO 96/19224 | 6/1996 |
| WO | WO 97/34890 | 9/1997 |
| WO | WO 98/04551 | 2/1998 |
| WO | WO 98/04552 | 2/1998 |
| WO | WO 98/16528 | 4/1998 |
| WO | WO 98/34613 | 8/1998 |

(Continued)

OTHER PUBLICATIONS

Dorwald F. A. Side Reactions in Organic Synthesis, 2005, Wiley: VCH, Weinheim p. IX of Preface.*
Kiss, et. al., Acta Pharmaceutica Hungarica (1997), 67(6), 255-261.*
Davis et al., "Inhibitors of Protein Kinase C. 1. 2,3-Bisarylmaleimides", Journal of Medicinal Chemistry 35:177-184 (1992).
Slater et al., "Indolocarbazoles: Potent, Selective Inhibitors of Human Cytomegalovirus Replication", Bioorganic & Medicinal Chemistry 7: 1067-1074 (1999).
European Patent Office, International Search Report for International Application No. PCT/US00/33274, mailed Jun. 29, 2001.
European Patent Office, International Search Report for International Application No. PCT/US00/33273, mailed Jul. 23, 2001.
Walker, "Staurosporine: Discovery of a Potential Anti-Cancer Drug?", http://freespace.virgin.net/clive.walker1/stauroporine/staurosporine2.html (Dec. 2001).

(Continued)

Primary Examiner — Jeffrey Murray
(74) Attorney, Agent, or Firm — Sunstein Kann Murphy & Timbers LLP

(57) ABSTRACT

The present invention relates to quinazolinone compounds, and methods of preparation of these compounds. The present invention also relates to pharmaceutical compositions comprising the quinazolinone compounds. The present invention provides methods of treating a cell proliferative disorder, such as a cancer, by administering to a subject in need thereof a therapeutically effective amount of a quinazolinone compound of the present invention.

26 Claims, 2 Drawing Sheets

FOREIGN PATENT DOCUMENTS

| WO | WO 00/47575 | | 8/2000 |
|---|---|---|---|
| WO | WO 01/30768 | | 5/2001 |
| WO | WO 01/44235 | A2 | 6/2001 |
| WO | WO 01/44235 | A3 | 6/2001 |
| WO | WO 01/44247 | A2 | 6/2001 |
| WO | WO 01/74807 | | 10/2001 |
| WO | WO 01/85685 | | 11/2001 |
| WO | WO 01/98278 | | 12/2001 |
| WO | WO 02/02593 | A2 | 1/2002 |
| WO | WO 02/02593 | A3 | 1/2002 |
| WO | WO 03/11224 | A2 | 2/2003 |
| WO | WO 03/11224 | A3 | 2/2003 |
| WO | WO 03/039460 | | 5/2003 |
| WO | WO 03/043995 | | 5/2003 |
| WO | WO 03/066808 | A2 | 8/2003 |
| WO | WO 03/066808 | A3 | 8/2003 |
| WO | WO 03/070701 | A2 | 8/2003 |
| WO | WO 03/070701 | A3 | 8/2003 |
| WO | WO 03/076442 | | 9/2003 |
| WO | WO 03/097053 | | 11/2003 |
| WO | WO 03/103575 | | 12/2003 |
| WO | WO 2004/009036 | A2 | 1/2004 |
| WO | WO 2004/009036 | A3 | 1/2004 |
| WO | WO 2004/039774 | A2 | 5/2004 |
| WO | WO 2004/039774 | A3 | 5/2004 |
| WO | WO 2004/091548 | A2 | 10/2004 |
| WO | WO 2004/091548 | A3 | 10/2004 |
| WO | WO 2004/096224 | A2 | 11/2004 |
| WO | WO 2004/096224 | A3 | 11/2004 |
| WO | WO 2004/110990 | A2 | 12/2004 |
| WO | WO 2004/111058 | | 12/2004 |
| WO | WO 2005/001486 | | 1/2005 |
| WO | WO 2005/007193 | A2 | 1/2005 |
| WO | WO 2005/007193 | A3 | 1/2005 |
| WO | WO 2005/058965 | | 6/2005 |
| WO | WO 2006/044869 | | 4/2006 |
| WO | WO 2006/086484 | | 8/2006 |
| WO | WO 2006/105511 | | 10/2006 |

OTHER PUBLICATIONS

Li et al., "*An Improved Protocol for the Preparation of 3-Pyridyl- and Some Arylboronic Acids*", J. Org. Chem. 67: 5394-5397 (2002).

Marson et al., "*Highly Efficient Syntheses of 3-Aryl-2-cycloalken-l-ones, and an Evaluation of Their Liquid Crystalline Properties*", Tetrahedron 59: 4377-4381 (2003).

Zhu et al, "*Synthesis of 1,7-Annulated Indoles and Their Applications in the Studies of Cyclin Dependent Kinase Inhibitors*", Bioorganic & Medicinal Chemistry Letters 14: 3057-3061 (2004).

Al-Awar et al., "*1,7-Annulated Indolocarbazoles as Cyclin-dependent Kinase Inhibitors*", Bioorganic & Medicinal Chemistry Letters 14: 3217-3220 (2004).

European Patent Office; Authorized Officer: Helps, I., *Notification of Transmittal of the International Search Report and the Written Opinion of the International Searching Authority, or the Declaration*, PCT/US2006/004456, mailed Jul. 5, 2006, 13 pages.

European Patent Office; Authorized Officer: Helps, I., *Notification Concerning Transmittal of International Preliminary Report on Patentability and Written Opinion of the International Searching Authority*, PCT/US2006/004456, mailed Aug. 14, 2007, 8 pages.

European Searching Authority, *International Search Report*, PCT/US2008/067571, dated Jun. 16, 2009, 16 pages.

Bergnes, et. al., "*Mitotic kinesins: Prospects for Antimitoticv drug discovery*," Current Topics in Medicinal Chemistry, vol. 5, No. 2, pp. 127-145, Apr. 2005.

Coleman, et al., "*Inhibitors of the mitotic kinesin spindle protein*," Expert Opin., Thec. Patents, vol. 14, No. 12, pp. 1659-1668, Jan. 2004.

El-Sharief, et al., "*Oxidation of 3-aminoquinazolinones with lead tetraacetate. A novel synthesis of naphtha-fused azirino-pyrazolo- and 1, 4, 5-oxadiazepino-quinazolinones*," J. Chem. Research, No. 5, pp. 205-208, Jan. 2002.

Tiwari, et al., "*Synthesis and biological properties of 4-(3H)-quinazolone derivatives*," European Journal of Medicinal Chemistry, vol. 42, No. 9, pp. 1234-1238, Aug. 2007.

\* cited by examiner

QUINAZOLINONE COMPOUNDS AND METHODS OF USE THEREOF

CROSS-REFERENCE TO RELATED APPLICATIONS

This application claims the benefit of U.S. Provisional Applications No. 60/945,838, filed Jun. 22, 2007, the contents of which are incorporated herein by reference in their entirety.

BACKGROUND OF THE INVENTION

Cancer is the second leading cause of death in the United States, exceeded only by cardiovascular disease. (*Cancer Facts and Figures* 2005, American Cancer Society, Inc.) Despite recent advances in cancer diagnosis and treatment, surgery and radiotherapy may be curative if a cancer is found early, but current drug therapies for metastatic disease are by and large only palliative and seldom offer a long-term cure. Even with new chemotherapies entering the market, the need continues for effective new drugs used either in monotherapy or in combination with existing agents as first line therapy, and as second and third line therapies in treatment of resistant tumors.

Improving the specificity of agents used to treat cancer is of considerable interest because of the therapeutic benefits which would be realized if the side effects associated with the administration of these agents could be reduced. One approach for cancer treatment is targeting mitotic processes of mammalian cells. Examples of the therapeutic agents targeting mitosis include the taxanes, and the camptothecin class of topoisomerase I inhibitors.

An emerging target class for cancer treatment is mitotic kinesins. Mitotic kinesins are enzymes essential for assembly and function of the mitotic spindle, but are not generally part of other microtubule structures, such as in nerve processes. Mitotic kinesins play an essential role during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP (also termed Eg5). KSP belongs to an evolutionarily conserved kinesin subfamily of plus-end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in non-human organisms bundle antiparallel microtubules and slide them relative to one another, thus forcing the two spindle poles apart. KSP may also mediate anaphase B spindle elongation and focusing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004423 and U37426], and a fragment of the KSP gene (TRIP5) has been described [Lee, et al., Mol. Endocrinol., 9:243-54 (1995); GenBank accession number L40372]. Xenopus KSP homologs (Eg5), as well as Drosophila K-LP61 F/KRP 130 have been reported.

Certain quinazolinones have been recently described as being inhibitors of KSP [PCT Publ. WO 01/30768, May 3, 2001; PCT Publ. WO 01/98278, Dec. 27, 2001; PCT Publ. WO 01/30768, May 3, 2001; PCT Publ. WO 03/039460, May 15, 2003; PCT Publ. WO 03/043995, May 30, 2003; PCT Publ. WO 03/070701, Aug. 28, 2003; PCT Publ. WO 03/097053, Nov. 27, 2003; and PCT Publ. WO 04/009036, Jan. 29, 2004].

Quinazolinone derivatives are privileged structures present in many biologically active compounds such methaqualone, a sedative-hypnotic agent, chloroqualone, an antitussive agent, and piriqualone, an anticonvulsant. It has been known that quinazolinones and derivatives have a wide variety of biological properties such as hypnotic, analgesic, anticonvulsant, antitussive and anti-inflammatory activities.

Quinazolinone derivatives for which specific biological uses have been described include U.S. Pat. No. 5,147,875 describing 2-(substituted phenyl)-4-oxoquinazolines with bronchodilator activity is described. U.S. Pat. Nos. 3,723, 432, 3,740,442, and 3,925,548 describe a class of 1-substituted-4-aryl-2(1H)-quinazolinone derivatives useful as anti-inflammatory agents. European patent publication EP 0 056 637 B1 claims a class of 4(3H)-quinazolinone derivatives for treating hypertension. European patent publication EP 0 884 319 A1 describes pharmaceutical compositions of quinazolin-4-one derivatives used for the treatment of neurodegenerative, psychotropic, and drug and alcohol induced central and peripheral nervous system disorders.

Quinazolinone derivatives are one of a growing list of therapeutic agents used for the treatment of cellular proliferate disorders, including cancer. In this area, for example, PCT WO 96/06616 describes a pharmaceutical composition containing a quinazolinone derivative to inhibit vascular smooth cell proliferation. PCT WO 96/19224 uses this same quinazolinone derivative to inhibit mesangial cell proliferation. U.S. Pat. Nos. 4,981,856, 5,081,124, and 5,280,027 describes the use of quinazolinone derivatives to inhibit thymidylate synthase, the enzyme that catalyzes the methylation of deoxyuridine monophosphate to produce thymidine monophosphate which is required for DNA synthesis. U.S. Pat. Nos. 5,747,498 and 5,773,476 describes quinazolinone derivatives used for the treatment of cancer characterized by over-activity or inappropriate activity of tyrosine receptor kinase. U.S. Pat. No. 5,037,829 claims (1H-azol-1-ylmethyl) substituted quinazoline compositions for the treatment of carcinomas that occur in epithelial cells. PCT WO 98/34613 describes a composition containing a quinazolinone derivative useful for attenuating neovascularization and for treating malignancies. U.S. Pat. No. 5,187,167 describes pharmaceutical compositions comprising quinazolin-4-one derivatives that possess anti-tumor activity.

The references cited herein are not admitted to be prior art to the claimed invention.

SUMMARY OF THE INVENTION

The present invention provides a compound of formula I, or pharmaceutically acceptable salts thereof:

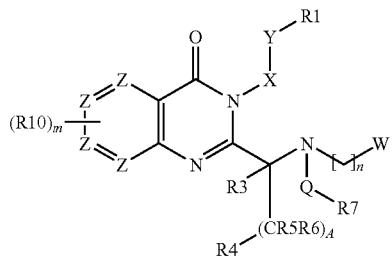

Wherein m, n and A are independently selected from the group consisting of 0, 1, 2, 3, and 4.

R1 is selected from the group consisting of H, alkyl, aryl, substituted aryl, haloaryl, bi-aryl, or bis-aryl, alkenyl, alkynyl, heteroaryl, cycloalkyl, heterocyclyl, haloalkyl, and perfluoroalkyl;

Y is selected from the group consisting of a bond, —C=O, —S=O, and —S(O)$_2$;

X is selected from the group consisting of NR2, O, S and CHR2; R1 and R2, taken together, may form a ring; when X is CHR2, R4 is alkynyl, or alkenyl;

R2 is selected from the group consisting of hydrogen, alkyl including lower alkyl, aryl, alkenyl, alkynyl, heteroaryl, alkylheteroaryl, cycloalkyl, heterocyclyl, and perfluoroalkyl;

R3 is selected from H, alkyl, aryl, alkylaryl, heteroaryl, perfluoroalkyl, alkenyl, and alkynyl;

R4 is selected from H, alkyl, substituted aryl, heteroaryl, alkenyl, alkynyl, and S-alkyl;

Each R5 and each R6 are independently selected from the group consisting of H, halogen, hydroxyl, nitrogen, amino, cyano, alkoxy, alkylthio, methylenedioxy, or haloalkyloxy; or alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido;

Q is either absent or selected from the group consisting of —CO—, —COO—, —CONR11, —C(=S)—, —CH$_2$—, —SO—, and —SO$_2$—;

R7 is selected from the group consisting of hydrogen, alkyl, aryl, alkylaryl, heteroaryl, aryls substituted with heterocycles;

W is selected from H or NR8R9; where R8 and R9 are independently selected from the group consisting of hydrogen, alkyl, aryl, heteroaryl, alkenyl, alkynyl, COR13, —CO$_2$R13, —CONR14R14, —SOR13, —SO$_2$R13, —C(=S)R14, —C(=NH)R14, —C(=O)NR15R15, and —C(=S)NR14R15, or R8 and R9 together with the N they are bonded to optionally form a heterocycle or substituted heterocycle;

Each Z is independently selected from the group consisting of N, and C; m is 0 when all Zs are N.

Each R10 is independently selected from the group consisting of hydrogen, halogen, hydroxyl, nitro, amino, cyano, alkoxy, alkylthio, methylenedioxy, or haloalkyloxy; alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido;

R11, R12, R13, R14, and R15 are independently selected from the group consisting of hydrogen, alkyl, aryl, alkylaryl, heteroaryl, oxaalkyl, oxaalkylaryl, and substituted oxaalkylaryl.

In an embodiment, the stereochemistry of the compound is of "R" configuration.

The present invention also provides a pharmaceutical composition comprising a compound of formula I in combination with a pharmaceutically acceptable carrier or excipient. In an embodiment, the pharmaceutical composition further comprises a second chemotherapeutic agent.

The present invention further provides a method of treating a cell proliferative disorder. The method comprises administering to a subject in need thereof a therapeutically effective amount of a compound of formula I, or a pharmaceutically acceptable salt thereof, or a prodrug or metabolite thereof, in combination with a pharmaceutically acceptable carrier, wherein said cell proliferative disorder is treated.

In an embodiment, the cell proliferative disorder is a precancerous condition. In another embodiment, the cell proliferative disorder is a cancer. In a further embodiment, the cancer is adenocarcinoma, squamous carcinoma, sarcoma, lymphoma, multiple myeloma, or leukemia. Alternatively, the cancer is lung cancer, colon cancer, breast cancer, pancreatic cancer, prostate cancer, acute leukemia, chronic leukemia, multiple melanoma, ovarian cancer, malignant glioma, leiomyosarcoma, hepatoma, or head and neck cancer. The cancer can be primary cancer or metastatic cancer.

In an embodiment, the compound of formula I, or a pharmaceutically acceptable salt thereof, or a prodrug or metabolite thereof, is administered in combination with a second chemotherapeutic agent.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1A:
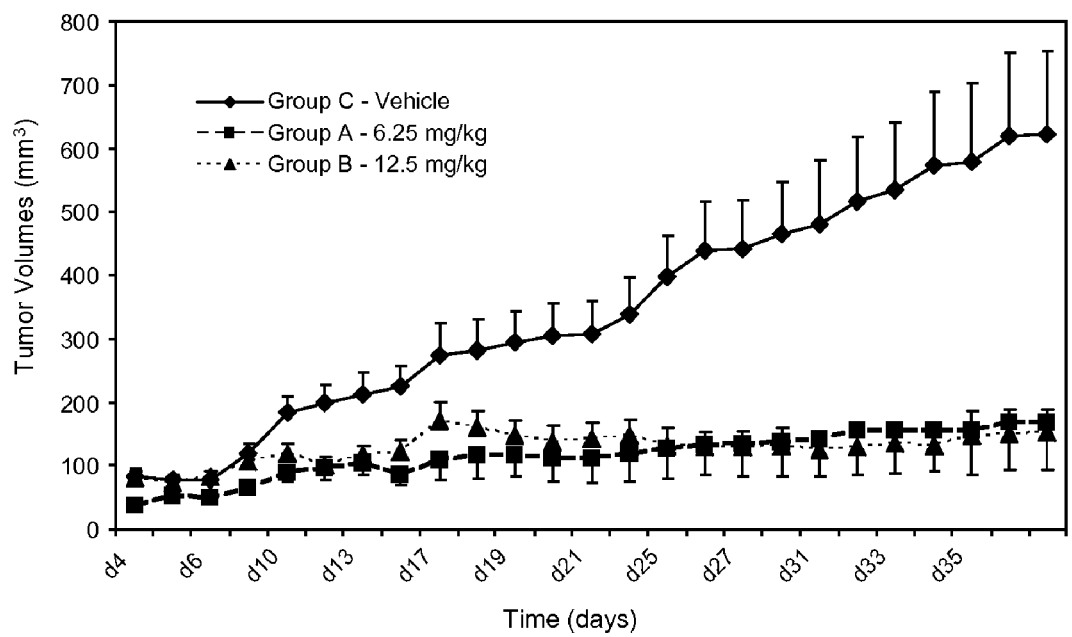
FIGS. 1A and 1B shows the effect of N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide on PACA-2 xenograft model.

This invention relates to quinazolinone derivatives. In an embodiment, the compounds of the present invention are inhibitors of mitotic kinesins, the mitotic kinesin KSP in particular. In a further embodiment, the compounds of the present invention are useful for treating cellular proliferative diseases including cancer.

1. Aryl Quinazolinone Derivatives

The present invention relates to new aryl quinazolinone derivatives, their pharmaceutically acceptable salts, stereoisomers, and prodrugs that can be used to treat cellular proliferative diseases, disorders associated with KSP kinesin activity, and inhibit KSP kinesin.

In one embodiment, the aryl quinazolinone derivatives are compounds of formula I, or pharmaceutically acceptable salts thereof:

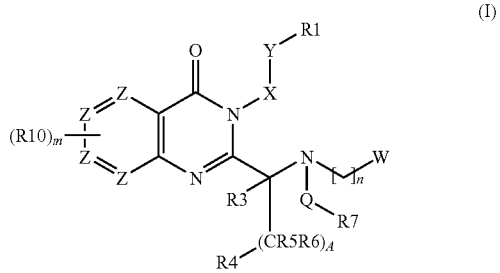

(I)

Wherein m, n and A are independently selected from the group consisting of 0, 1, 2, 3, and 4.

R1 is selected from the group consisting of H, alkyl, aryl, substituted aryl, haloaryl, bi aryl, or bis aryl, alkenyl, alkynyl, heteroaryl, cycloalkyl, heterocyclyl, haloalkyl, and perfluoroalkyl;

Y is selected from the group consisting of a bond, —C=O, —S=O, and —S(O)$_2$;

X is selected from the group consisting of NR2, O, S and CHR2; R1 and R2, taken together, may form a ring; when X is CHR2, R4 is alkynyl, or alkenyl;

R2 is selected from the group consisting of hydrogen, alkyl including lower alkyl, aryl, alkenyl, alkynyl, heteroaryl, alkylheteroaryl, cycloalkyl, heterocyclyl, and perfluoroalkyl;

R3 is selected from H, alkyl, aryl, alkylaryl, heteroaryl, perfluoroalkyl, alkenyl, and alkynyl;

R4 is selected from H, alkyl, aryl, substituted aryl, heteroaryl, alkenyl, alkynyl, and S-alkyl;

Each R5 and each R6 are independently selected from the group consisting of H, halogen, hydroxyl, nitrogen, amino, cyano, alkoxy, alkylthio, methylenedioxy, or haloalkyloxy; or alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido;

Q is either absent or selected from the group consisting of —CO, —COO, —CONR11, —C(=S), —CH$_2$, —SO, and —SO$_2$;

R7 is selected from the group consisting of hydrogen, alkyl, aryl, alkylaryl, heteroaryl, aryls substituted with heterocycles;

W is selected from H or NR8R9; where R8 and R9 are independently selected from the group consisting of hydrogen, alkyl, aryl, heteroaryl, alkenyl, alkynyl, COR13, —CO$_2$R13, —CONR14R14, —SOR13, —SO$_2$R13, —C(=S)R14, —C(=NH)R14, —C(=O)NR15R15, and —C(=S)NR14R15; or R8 and R9 together with the N they are bonded to optionally form a heterocycle or substituted heterocycle;

Each Z is independently selected from the group consisting of N, and C; m is 0 when Z is N.

Each R10 is independently selected from the group consisting of hydrogen, halogen, hydroxyl, nitro, amino, cyano, alkoxy, alkylthio, methylenedioxy, or haloalkyloxy; alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido;

R11, R12, R13, R14, and R15 are independently selected from the group consisting of hydrogen, alkyl, aryl, alkylaryl, heteroaryl, oxaalkyl, oxaalkylaryl, and substituted oxaalkylaryl.

In an embodiment, A is 0, 1, or 2.
In an embodiment, A is 1, and R5 and R6 are H.
In an embodiment, m is 1.
In an embodiment, n is 3.
In an embodiment, n is 2.
In an embodiment, R8 and R9 are H.
In an embodiment, X is NR2. In a further embodiment, X is NH$_2$. In an alternative embodiment, X is O or S.
In another embodiment, X is CHR2. In a further embodiment, X is ethynyl.
In an embodiment, Y is a bond.
In an embodiment, R1 is phenyl.
In an embodiment, R2 is H.
In an embodiment, R3 is H.
In an embodiment, R4 is ethynyl, methyl, ethyl, propyl, or tert-butyl.
In an embodiment, R5 and R6 are H.
In an embodiment, Q is absent.
In an embodiment, Q is CO, CH2, CHR12, or SO2.
In an embodiment, R7 is unsubstituted or substituted phenyl.
In an embodiment W is H.
In an embodiment, R8 and R9 are H.

Some representative compounds of Formula I are shown as follows: N-(3-Amino-propyl)-3-chloro-N-[(R)-1-(7-chloro-4-oxo-3-phenylamino-3,4-dihydro-quinazolin-2-yl)-but-3-ynyl]-2-fluoro-benzamide, N-(3-Aminopropyl)-N-[1-(3-anilino-6-chloro-4-oxo-3,4-dihydroquinazolin-2-yl)propyl]-4-methylbenzamide, 2-{(R)-1-[(3-Amino-propyl)-benzylamino]-propyl}-7-chloro-3-phenylamino-3H-quinazolin-4-one, 2-{(R)-1-[(3-Amino-propyl)-(4-methyl-benzyl)-amino]-but-3-ynyl}-7-chloro-3-phenylamino-3H-quinazolin-4-one, N-(2-Aminoethyl)-N-[1-(3-anilino-7-chloro-4-oxo-3,4-dihydroquinazolin-2-yl)propyl]-3-chloro-2-fluorobenzamide, N-(3-Amino-propyl)-N-[1-(7-chloro-4-oxo-3-phenylamino-3,4-dihydro-quinazolin-2-yl)-3-methylsulfanyl-propyl]-4-pyrazol-1-yl-benzamide, N-(3-Amino-propyl)-N-[(R)-1-(7-chloro-4-oxo-3-phenylamino-3,4-dihydro-quinazolin-2-yl)-but-3-ynyl]-4-methyl-benzenesulfonamide, N-(3-Amino-propyl)-N-[(R)-1-(7-chloro-4-oxo-3-phenylamino-3,4-dihydro-quinazolin-2-yl)-propyl]-3-fluoro-benzenesulfonamide, N-(3-Aminopropyl)-N-[1-(3-anilino-7-chloro-4-oxo-3,4-dihydroquinazolin-2-yl)pentyl]-4-methylbenzamide, N-(3-Aminopropyl)-N-[1-(3-anilino-7-chloro-4-oxo-3,4-dihydroquinazolin-2-yl)-3,3-dimethylbutyl]-4-bromobenzamide, N-(3-Aminopropyl)-N-[1-(3-anilino-6-methyl-4-oxo-3,4-dihydroquinazolin-2-yl)propyl]-4-methylbenzamide, N-(3-Aminopropyl)-N-[1-(7-chloro-4-oxo-3-phenoxy-3,4-dihydroquinazolin-2-yl)propyl]-4-methylbenzamide, and N-(3-Aminopropyl)-N-[(1R)-1-(3-anilino-7-chloro-4-oxo-3,4-dihydroquinazolin-2-yl)propyl]-1,3,5-trimethyl-1H-pyrazole-4-sulfonamide, N-(3-Amino-propyl)-N-[(R)-1-(7-chloro-4-oxo-3-phenylamino-3,4-dihydroquinazolin-2-yl-but-3-ynyl]-2,3,5,6-tetrafluoro-benzamide, (R)-N-(3-Aminopropyl)-N-(1-(7-chloro-4-oxo-3-(phenylamino)-3,4-dihydroquinazolin-2-yl)but-3-ynyl)-2,3,4,5-tetrafluorobenzamide, N-(3-Aminopropyl)-3-chloro-N-(1-(7-chloro-4-oxo-3-(phenylamino)-3,4-dihydroquinazolin-2-yl)pent-3-ynyl)-2-fluorobenzamide, N-(3-Amino-propyl)-N-[(R)-1-(7-chloro-4-oxo-3-phenylamino-3,4-dihydro-quinazolin-2-yl)-but-3- ynyl]-2,3-difluoro-4-methyl-benzamide, (R)-N-(3-Aminopropyl)-N-(1-(7-chloro-4-oxo-3-phenylamino)-3,4-dihydroquinazolin-2-yl)but-3-ynyl)-2,3-difluoro-6-methoxybenzamide, (R)-N-(3-Aminopropyl)-N-(1-(7-chloro-4-oxo-3-phenylamino)-3,4-dihydroquinazolin-2-yl)but-3-ynyl)-2,3-difluoro-4-methoxybenzamide, (R)-N-(3-Aminopropyl)-4-chloro-N-(1-(7-chloro-4-oxo-3-phenylamino)-3,4-dihydroquinazolin-2-yl)but-3-ynyl)-2,6-difluoro-benzamide, (R)-N-(3-Aminopropyl)-N-(1-(7-chloro-4-oxo-3-(phenylamino)-3,4-dihydroquinazolin-2-yl)but-3-ynyl)-3,5-difluorobenzamide, (R)-N-(3-Aminopropyl)-N-(1-(7-chloro-4-oxo-3-(phenylamino)-3,4-dihydroquinazolin-2-yl)but-3-ynyl)-2,3,5-trifluorobenzamide, (R)-N-(3-Aminopropyl)-N-(1-(7-chloro-4-oxo-3-(phenylamino)-3,4-dihydroquinazolin-2-yl)but-3-ynyl)-2,3-difluorobenzamide.

Representative compounds of the present invention are also shown in the Examples.

As used in this description and the accompanying claims, all technical and scientific terms used herein have the same meaning as commonly understood by one of ordinary skill in the art to which this invention belongs unless defined otherwise. In case of a conflict in terminology, the present specification controls. The following terms generally have the following meanings.

As used herein, the term "alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl). "Alkyl" further includes alkyl groups that have oxygen, nitrogen, or sulfur atoms replacing one or more hydrocarbon backbone carbon atoms. In certain embodiments, a straight chain or branched alkyl has six or fewer carbon atoms in its backbone (e.g., $C_1$-$C_6$ for straight chain, $C_3$-$C_6$ for branched chain), and more preferably four or fewer.

The term "alkyl" also includes both "unsubstituted" and "substituted alkyls", the latter of which refers to alkyl moieties having substituents replacing a hydrogen on one or more carbon of the hydrocarbon backbone. Such substituents can include, for example, alkyl, alkenyl, alkynyl, hydroxyl, alkylcarbonyl, arylcarbonyl, alkoxycarbonyl, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl ($S(O)_2NH_2$), aminesulfoxide (NHS(O) or S(O)NH), sulfonamide ($NHS(O)_2$ or $S(O)_2NH$), nitro, —$CF_3$, halogen, cyano, azido, heterocyclyl, alkylaryl, or an aromatic or heteroaromatic moiety. An "alkylaryl" or aralkyl moiety is an alkyl moiety substituted with an aryl (e.g., methylphenyl (benzyl)). "Alkyl" also includes the side chains of natural and unnatural amino acids.

Aryl includes groups with aromaticity, including 5- and 6-membered "unconjugated", or single-ring aromatic groups that may include from one to four heteroatoms, as well as "conjugated", or multicyclic systems with at least one aromatic ring. Examples of aryl groups include phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term "aryl" includes multicyclic groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthidine, indole, benzofuran, purine, benzofuran, deazapurine, or indolizine. Those aryl groups having heteroatoms in a ring structure may also be referred to as "aryl heterocycles", "heterocycles", "heterocyclyls", "heteroaryls" or "heteroaromatics" e.g., pyridine, pyrazole, pyrimidine, furan, isoxazole, imidazole [2,1,b]thiazole, triazole, pyrazine, benzothiophene, imidazole, or thiophene.

The aryl ring can be substituted at one or more ring positions with such substituents as described above, as for example, halogen, hydroxyl, alkyl, alkoxy, alkylcarbonyloxy, arylcarbonyloxy, alkoxycarbonyloxy, aryloxycarbonyloxy, carboxylate, carboxyacid, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, carboxyalkyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, or sulfur replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, phenyl, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

As used herein, "amine" or "amino" includes compounds where a nitrogen atom is covalently bonded to at least one carbon or heteroatom. "Alkylamino" includes groups of compounds wherein nitrogen is bound to at least one additional alkyl group. Examples of alkylamino groups include benzylamino, methylamino, ethylamino, and phenethylamino. "Dialkylamino" includes groups wherein the nitrogen atom is bound to at least two additional alkyl groups. Examples of dialkylamino groups include dimethylamino and diethylamino. "Arylamino" and "diarylamino" include groups wherein the nitrogen is bound to at least one or two aryl groups, respectively. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl, or heterocycle. Substituents on amide groups may be further substituted.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "cycloalkyl" includes saturated acyclic groups (e.g., cyclopropyl, cyclopentyl, cyclohexyl, cycloheptyl, cyclooctyl). Preferred cycloalkyls have from three to eight carbon atoms in their ring structure, and more preferably have five or six carbon atoms in the ring structure. Cycloalkyls includes both "unsubstituted cycloalkyls" and "substituted cycloalkyls", the latter of which refers to replacing a hydrogen on one or more of the carbons in the ring structure. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The terms "heterocyclyl" or "heterocyclic group" include closed ring structures, e.g., 3- to 10-, or 4- to 7-membered rings, which include one or more heteroatoms. "Heteroatom"

includes atoms of any element other than carbon or hydrogen. Examples of heteroatoms include nitrogen, oxygen, or sulfur.

Heterocyclyl groups can be saturated or unsaturated and include pyrrolidine, pyrazine, pyrimidine, oxolane, 1,3-dioxolane, thiolane, tetrahydrofuran, tetrahydropyran, piperidine, piperazine, pyrrolidine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, carboxyacid, alkylcarbonyl, alkoxycarbonyl, aminocarbonyl, alkylthiocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "hydroxy" or "hydroxyl" includes groups with an —OH or —$O^-$.

The term "halogen" includes fluorine, bromine, chlorine, iodine, etc. The term "perhalogenated" generally refers to a moiety wherein all hydrogens are replaced by halogen atoms.

The term "C1-C6" includes one to six carbon atoms (C1, C2, C3, C4, C5 or C6). The term "C2-C6" includes two to six carbon atoms (C2, C3, C4, C5 or C6). The term "C3-C6" includes three to six carbon atoms (C3, C4, C5 or C6). The term "C3-C8" includes three to eight carbon atoms (C3, C4, C5, C6, C7 or C8). The term "C5-C8" includes five to eight carbon atoms (C5, C6, C7 or C8).

It should be noted that any heteroatom or carbon atom with unsatisfied valences is assumed to have the hydrogen atom to satisfy the valences.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood accordingly that the isomers arising from such asymmetry (e.g. all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

In the specification, the singular forms also include the plural, unless the context clearly dictates otherwise.

2. The Synthesis of Compounds

The present invention also provides methods for the synthesis of the compounds of Formula I. In one embodiment, the present invention provides a method for the synthesis of compounds according to the following schemes, and the protocols shown in the Examples.

Throughout the description, where compositions are described as having, including, or comprising specific components, it is contemplated that embodiments of the compositions may also consist essentially of, or consists of, the recited components. Similarly, where methods or processes are described as having, including, or comprising specific process steps, the processes may also include embodiments that consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$ ed.; John Wiley & Sons: New York, 1999, incorporated by reference herein, are useful and recognized reference textbooks of organic synthesis known to those in the art. The following descriptions of synthetic methods are designed to illustrate, but not limit, general procedures for the preparation of compounds of the invention.

The compounds of this invention with general formula (I) may be prepared according to the following schemes from commercially available starting materials or starting materials, which can be prepared using literature procedures. These schemes show the preparation of representative compounds of this invention.

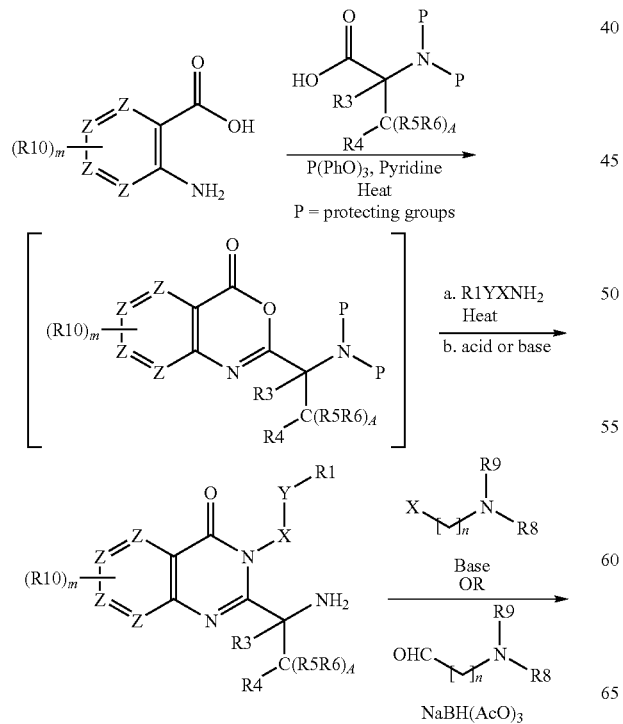

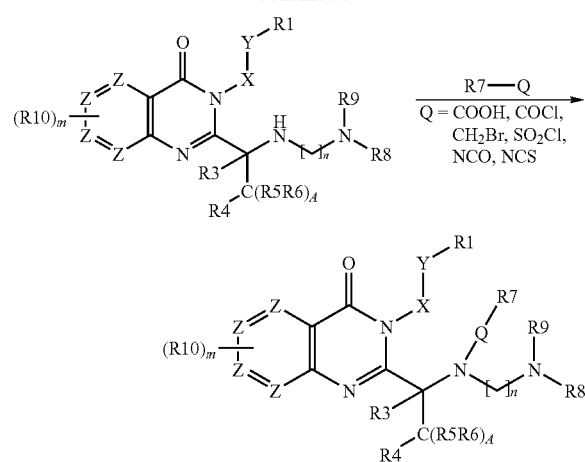

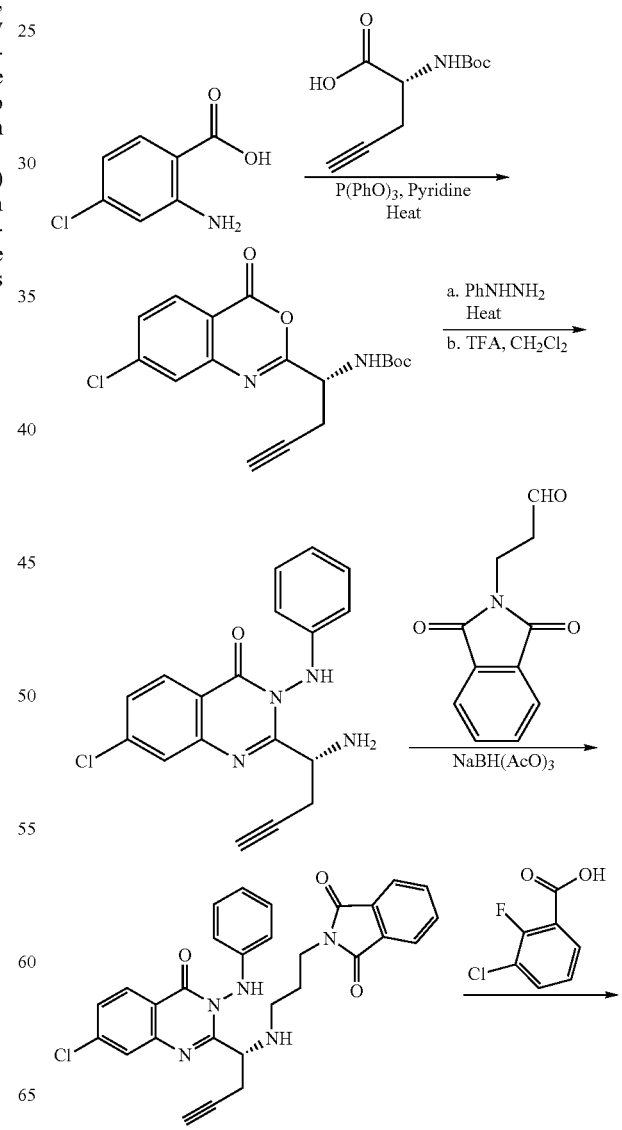

-continued

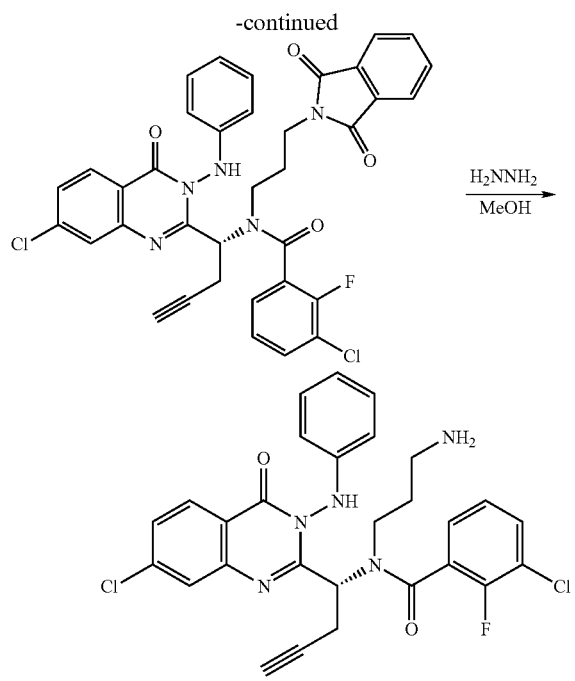

The compounds of formula I of this invention may be prepared by employing reaction as shown in schemes 1 and 2.

Compounds encompassed in the invention can be produced according to this or other synthetic processes without departing from the spirit or essential characteristics of the invention. All changes that come within the meaning and range of equivalency of the compounds are intended to be embraced herein. Thus, it is expected that one of ordinary skill in the art would know how to alter the synthetic schemes illustrated herein so as to produce a desired substitution pattern on a compound, produce an increased or decreased product yield, minimize reaction side products, eliminate the use of dangerous or toxic chemical reactants, and/or to produce a desired amount of product (e.g., scale-up reaction size for commercial manufacture), and the like.

The present invention further provides a compound prepared by one of the synthetic processes disclosed herein, such as those disclosed in the Examples.

3. Methods of Treatment

The present invention also provides a method for the treatment of a cell proliferative disorder in a mammal comprising administering to a mammal in need of such treatment, a therapeutically effective amount of a compound of Formula I. The invention further provides the use of a compound of Formula I for the preparation of a medicament useful for the treatment of a cell proliferative disorder. In one embodiment, the invention provides for the treatment of cancer or precancerous conditions in a mammal comprising administering to a mammal in need of such treatment, a therapeutically effective amount of a compound of Formula I. The mammal can be any mammal, e.g., a human, a primate, mouse, rat, dog, cat, cow, horse, pig. For example, the mammal is a human.

An effective amount of a compound of Formula I is used in a method to treat a cell proliferative disorder in a mammal without affecting normal cells of the mammal. For example, a therapeutically effective amount of a compound of Formula I is used in a method for treating cancer in a mammal by inducing cell death in cancer cells without affecting normal cells in the mammal. Cell death can occur by either apoptosis or necrosis mechanisms. In another example, administration of a therapeutically effective amount of a compound of Formula I induces cell death in abnormally proliferating cells without inducing cell death in normal cells.

The invention also provides a method of protecting against a cell proliferative disorder in a mammal by administering a therapeutically effective amount of a compound of Formula I to a mammal. The invention also provides the use of a compound of Formula I for the preparation of a medicament useful for the prevention of a cell proliferative disorder. In one embodiment, the invention provides for the prevention of cancer in a mammal comprising administering to a mammal in need of such treatment, a therapeutically effective amount of a compound of Formula I.

The compounds of the invention may be administered in the form of pharmaceutical compositions, e.g., as described herein.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large (e.g., a patient that has been diagnosed with a genetic or environmental risk factor). In one aspect, a subject in need thereof has a precancerous condition. In a preferred aspect, a subject in need thereof has cancer.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

As used herein, "monotherapy" refers to administration of a single active or therapeutic compound to a subject in need thereof. Preferably, monotherapy will involve administration of a therapeutically effective amount of an active compound. For example, cancer monotherapy with a compound according to an embodiment of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. In another aspect, treating cancer results in a reduction in tumor volume. In another aspect, treating cancer results in a decrease in number of tumors. In another aspect, treating cancer results in a decrease in number of metastatic lesions in other tissues or organs distant from the primary tumor site. In another aspect, treating cancer results in an increase in average survival time of a population of treated subjects in comparison to a population receiving carrier alone. In another aspect, treating cancer results in an increase in average survival time of a population of treated subjects in comparison to a population of untreated subjects. In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in tumor growth rate. In another aspect, treating cancer results in a decrease in tumor regrowth.

In another aspect, treating or preventing a cell proliferative disorder results in a reduction in the rate of cellular proliferation. In another aspect, treating or preventing a cell proliferative disorder results in a reduction in the proportion of proliferating cells. In another aspect, treating or preventing a cell proliferative disorder results in a decrease in size of an area or zone of cellular proliferation. In another aspect, treating or preventing a cell proliferative disorder results in a decrease in the number or proportion of cells having an abnormal appearance or morphology.

In additional aspects, a compound of the present invention, or a pharmaceutically acceptable salt, metabolite, analog or derivative thereof, can be administered in combination with a chemotherapeutic agent. Exemplary chemotherapeutics with activity against cell proliferative disorders are known to those of ordinary skill in the art, and may be found in reference texts such as the *Physician's Desk Reference*, 59$^{th}$ Edition, Thomson PDR (2005). For example, the chemotherapeutic agent can be a taxane, an aromatase inhibitor, an anthracycline, a microtubule targeting drug, a topoisomerase poison drug, a targeted monoclonal or polyclonal antibody, an inhibitor of a molecular target or enzyme (e.g., a kinase inhibitor), or a cytidine analogue drug. In preferred aspects, the chemotherapeutic agent can be, but is not restricted to, tamoxifen, raloxifene, anastrozole, exemestane, letrozole, cisplatin, carboplatin, TAXOL® (paclitaxel), cyclophosphamide, lovastatin, minosine, GEMZAR® (gemcitabine HCl), araC, 5-fluorouracil (5-FU), methotrexate (MTX), TAXOTERE® (docetaxel), ZOLADEX® (goserelin), vincristin, vinblastin, nocodazole, teniposide, etoposide, epothilone, navelbine, camptothecin, daunonibicin, dactinomycin, mitoxantrone, amsacrine, doxorubicin (adriamycin), epirubicin, idarubicin, or GLEEVEC® (imatanib), IRESSA® (gefitinib), TARCEVA® (erlotinib), NEXAVAR® (sorafenib), SUTENT® (sunitinib malate), HERCEPTIN® (trastuzumab), RITUXAN® (Rituximab), ERBITUX® (cetuximab), AVASTIN® (bevacizumab), or agents listed in http://www.cancer.org/docroot/cdg/cdg_0.asp. In another aspect, the chemotherapeutic agent can be a cytokine such as G-CSF (granulocyte colony stimulating factor). In another aspect, a compound of the present invention, or a pharmaceutically acceptable salt, metabolite, analog or derivative thereof may be administered in combination with radiation therapy. In yet another aspect, a compound of the present invention, or a pharmaceutically acceptable salt, metabolite, analog or derivative thereof may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

4. The Pharmaceutical Compositions and Formulations

A "pharmaceutically acceptable salt" or "salt" of the disclosed compound is a product of the disclosed compound that contains an ionic bond, and is typically produced by reacting the disclosed compound with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches, bioerodable implants and inhalants. In one embodiment, the active compound is mixed under sterile conditions with a pharmaceutically acceptable carrier, and with any preservatives, buffers, or propellants that are required.

The present invention also provides pharmaceutical formulations comprising a compound of Formula I in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A compound of Formula I is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of Formula I (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a compound of Formula I is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not so high as to cause unacceptable side effects. The state of the disease condition (e.g., cancer, psoriasis, and the like) and the health of the patient should be closely monitored during and for a reasonable period after treatment.

EXAMPLES

Examples are provided below to further illustrate different features of the present invention. The examples also illustrate useful methodology for practicing the invention. These examples do not limit the claimed invention.

Example 1

General Procedure A: Synthesis of N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide (1)

General Procedure A, Step 1: [(R)-1-(7-Chloro-4-oxo-3-phenylamino-3,4-dihydro-quinazolin-2-yl)-but-3-ynyl]-carbamic Acid Tert-butyl Ester

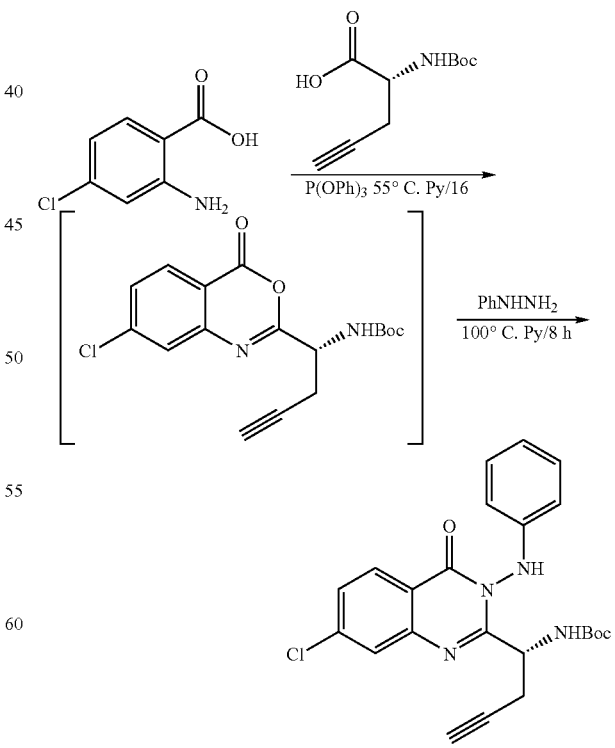

To a mixture of (R)-2-tert-butoxycarbonylamino-pent-4-ynoic acid (5.0 g, 23.5 mmol) in anhydrous pyridine (20 ml)

were added 2-amino-4-chloro-benzoic acid (4.03 g, 23.5 mmol) and triphenyl phosphite (7.40 ml). The reaction mixture was then heated at 55° C. for 16 h. To this was added phenylhydrazine (2.8 ml, 28.2 mmol). The resulting mixture was stirred at 100° C. for 8 h. After the solvent was removed, the residue was purified by flash column (hexane to 20% ethyl acetate in hexane) to give [(R)-1-(7-chloro-4-oxo-3-phenylamino-3,4-dihydro-quinazolin-2-yl)-but-3-ynyl]-carbamic acid tert-butyl ester (5.5 g, 53.4%) as off-white solid. M.p. 155-157° C. [LCMS]: 439 [M+H]. 400 MHz $^1$H NMR: (DMSO-d$_6$) δ 9.21 and 9.0 (s, s, 1H, rotamers), 8.08 (m, 1H), 7.81 (m, 1H), 7.60 (dd, J=2.0, 6.4 Hz, 1H), 7.31-7.18 (m, 3H), 6.89-6.67 (m, 3H), 5.14-4.97 (m, br, 1H), 2.86 (m, br, 2H), 2.25 (m, 1H), 1.32 (s, 9H).

Example 2

General Procedure A. Step 2: 2-((R)-1-Amino-but-3-ynyl)-7-chloro-3-phenylamino-3H-quinazolin-4-one

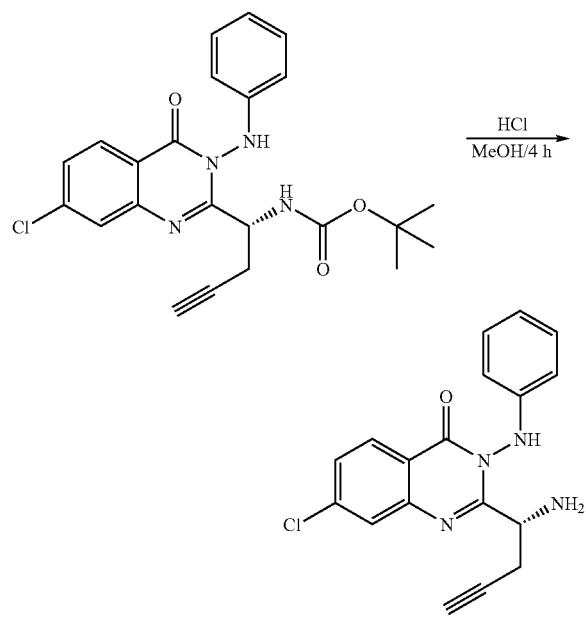

To a mixture of (R)-[1-(7-chloro-4-oxo-3-phenylamino-3,4-dihydro-quinazolin-2-yl)-but-3-ynyl]-carbamic acid tert-butyl ester (5.35 g, 12.2 mmol) in methanol (65 ml) was added HCl in dioxane (4M, 20 ml). The resulting solution was stirred and the reaction completion was monitored using HPLC/LCMS. The solvent was then removed and the mixture was triturated with diethyl ether to afford 2-((R)-1-amino-but-3-ynyl)-7-chloro-3-phenylamino-3H-quinazolin-4-one (4.60 g, 100%) as off-white solid. M.p. 175-180° C. LCMS: m/e 339 [M+H]. $^1$H NMR: (DMSO d$_6$) δ 9.27 (s, 1H), 8.73 (s, br, 3H), 8.15 (d, J=8.4 Hz, 1H), 7.79 (d, J=2.0 Hz, 1H), 7.70 (dd, J=2.0 and 8.4 Hz, 1H), 7.32 (t, J=8.0 Hz, 2H), 6.92 (t, J=7.6 Hz 1H), 6.68 (m, 2H), 4.90, 4.58 (m, 1H, rotomers), 3.18 (m, 1H), 3.08 (m 2H).

Example 3

General Procedure A, Step 3: 2-{3-[(R)-1-(7-chloro-4-oxo-3-phenylamino-3,4-dihydro-quinazolin-2-yl)-but-3-ynylamino]-propyl}-isoindole-1,3-dione To a mixture of (R)-(1-amino-but-3-ynyl)-7-chloro-3-phenylamino-3H-quinazolin-4-one (4.60 g, 12.2 mmol) and diisopropylethylamine (DIPEA) (5.5 ml) in dichloromethane (60 ml) was added a solution of 3-(1,3-dioxo-1,3-dihydro-isoindol-2-yl)-propionaldehyde (2.45 g, 12.1 mmol) in dichloroethane (10 ml), followed by a solution of sodium triacetoxy borohydride (NaBH(OAc)$_3$) (0.25M in dichloroethane, 100 ml). The reaction mixture was stirred at room temperature and the reaction progress was monitored by HPLC/MS. Upon completion, a saturated sodium carbonate solution (100 ml) was added. The resulted organic layer was collected and washed with brine solution. The solvent was removed and residue was purified by flash column to afford 2-{3-[(R)-1-(7-chloro-4-oxo-3-phenylamino-3,4-dihydro-quinazolin-2-yl)-but-3-ynylamino]-propyl}-isoindole-1,3-dione (6.1 g, 95%) as off-white solid. M.p. 78-80° C. LCMS: m/e 526 [M+H]. $^1$H NMR (DMSO-d$_6$): δ 9.09 (s, br, 1H), 8.07 (d, J=8.8 Hz, 1H), 7.74 (m, 1H), 7.83-7.76 (m, 5H), 7.58 (dd, J=8.8 and 2.0 Hz, 1H), 7.17 (t, J=7.6 Hz, 2H), 6.83 (brm, 1H), 6.65 (m, 2H), 4.1 and 4.0 (s, s, br, 1H, rotomers), 3.6 (t, J=6.8 Hz, 2H), 2.75 (s, br, 1H), 2.67-2.52 (brm, 2H), 2.35 (brm, 2H), 1.67 (brm, 2H).

Example 4

General Procedure A, Step 4: 3-Chloro-N-[(R)-1-(7-chloro-4-oxo-3-phenylamino-3,4-dihydro-quinazolin-2-yl)-but-3-ynyl]-N-[3-(1,3-dioxo-1,3-dihydro-isoindol-2-yl)-propyl]-2-fluoro-benzamide

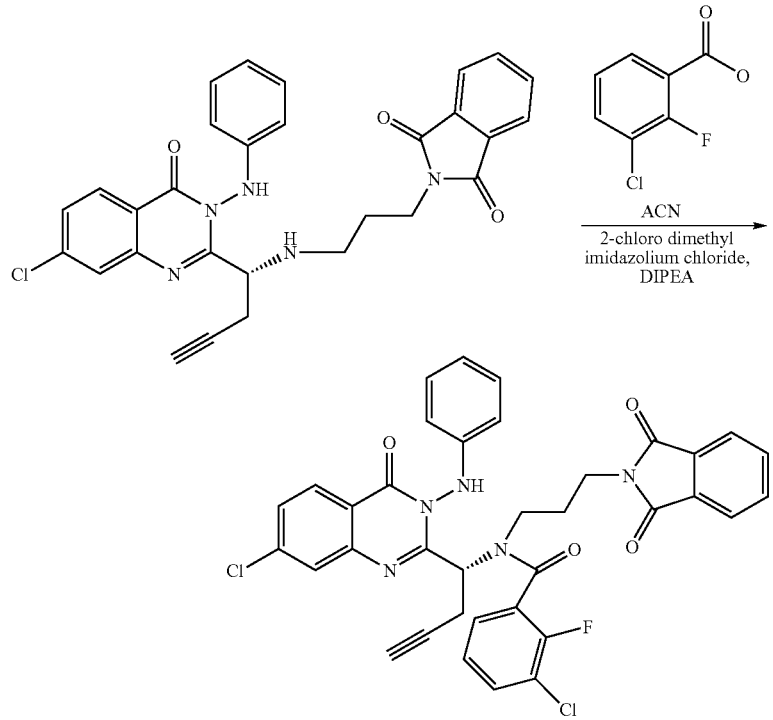

To a solution of 3-chloro-2-fluoro-benzoic acid (3.2 g, 18.3 mmol) of in acetonitrile (30 ml) was added 2-chloro-1,3-dimethylimidazolium chloride (DMC) (3.3 g, 19.5 mmol), followed by diisopropylethyl amine (6.8 ml, 39 mmol). The resulted solution was stirred at room temperature for 10 min, then transferred into flask containing (R)-2-{3-[1-(7-chloro-4-oxo-3-phenylamino-3,4-dihydro-quinazolin-2-yl)-but-3-ynylamino]-propyl}-isoindole-1,3-dione (6.1 g) in a 2.5M solution of diisopropylethyl amine in acetonitrile (30 ml). The reaction mixture was stirred at room temperature and the reaction progress was monitored by HPLC/MS. Upon completion, a saturated solution of sodium carbonate (100 ml) was added. The organic layers were collected and the aqueous layer was washed with EtOAc (2×50 ml). The combined organic layers were washed with brine (100 ml) and dried over sodium sulfate. The solvent was removed and residue was separated on silica gel column to afford 3-chloro-N-[(R)-1-(7-chloro-4-oxo-3-phenylamino-3,4-dihydro-quinazolin-2-yl)-but-3-ynyl]-N-[3-(1,3-dioxo-1,3-dihydro-isoindol-2-yl)propyl]-2-fluoro-benzamide as off-white solid (7.6 g, 96%). M.p. 130-132° C. LCMS: m/e 682 [M+H]. $^1$H NMR (CDCl$_3$): δ 8.09 (m, 1H), 7.71 (m, 3H), 7.46 (m, 1H), 7.35 (m, 2H), 7.29 (m, 1H), 7.16 (m, 1H), 7.10 (m, 1H), 7.03 (m, 1H), 6.90 (m, 1H), 6.82 (m, 1H), 6.68 (m, 1H), 6.50 (m, 1H), 3.73 (m, 1H), 3.58 (m, 1H), 3.51 (m, 1H), 3.38 (m, 1H), 3.26 (m, 1H), 3.06 (m, 1H), 2.88 (m, 1H), 2.01 (s, 1H), 1.80 (m, 1H), 1.54 (m, 1H).

Example 5

General Procedure A, Step 5: N-(3-Amino-propyl)-3-chloro-N-[(R)-1-(7-chloro-4-oxo-3-phenylamino-3,4-dihydro-quinazolin-2-yl)-but-3-ynyl]-2-fluoro-benzamide (1)

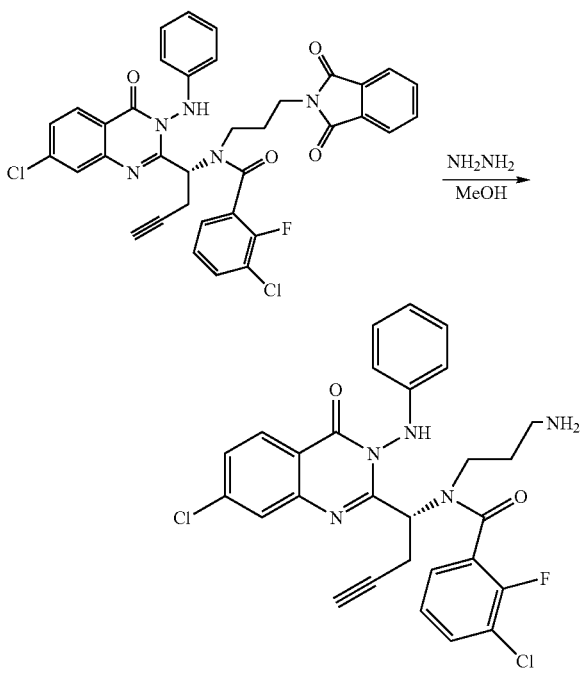

To a solution of (R)-3-chloro-N-[1-(7-chloro-4-oxo-3-phenylamino-3,4-dihydro-quinazolin-2-yl)-but-3-ynyl]-N-[3-(1,3-dioxo-1,3-dihydro-isoindol-2-yl)-propyl]-2-fluoro-benzamide (1.13 g, 1.65 mmol) in methanol (10 ml) and the solution was purged with N$_2$. To this solution was added hydrazine (110 μl). The mixture was then stirred at room temperature and the reaction progress was monitored by HPLC/MS. The reaction mixture was then filtered and solvent was removed from the filtrate. The residue was purified by flash column to afford N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide (708 mg, 91%) as off-white solid, M.p. 101-103° C. LCMS: m/e 552 [M+H]. $^1$H NMR (CDCl$_3$): δ 8.13 (d, J=8.8 Hz, 1H), 7.83 (s, 1H), 7.45 (dd, J=4.8 and 2.0 Hz, 1H), 7.32 (m, 1H), 7.22 (t, J=8.0 Hz, 1H), 7.15 (t, J=8.0 Hz, 1H), 7.05 (t, J=8.0 Hz, 1H), 6.95 (m, 1H), 6.84 (t, J=7.2 Hz, 1H), 6.72 (d, J=7.2 Hz, 1H), 6.48 (d, J=7.2 Hz 1H), 3.62 (m, 1H), 3.48 (m, 1H), 3.28 (br, 1H), 3.14 (m, 1H), 3.02 (br, 1H), 2.59 (m, 2H), 2.30 (br, 1H), 2.02 (t, 2.4 Hz, 1H), 1.36 (m, 2H).

Example 6

N-(3-Aminopropyl)-N-[1-(3-anilino-7-chloro-4-oxo-3,4-dihydroquinazolin-2-yl)propyl]-4-bromobenzamide (2)

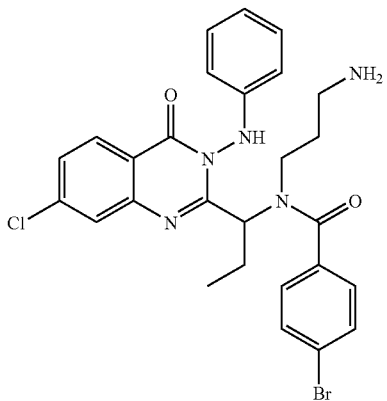

This was synthesized as described in general procedure A, except N-Boc-DL-2-amino butyric acid was used instead of (R)-2-tert-butoxycarbonylamino-pent-4-ynoic acid and 4-bromo benzoic acid was used instead of 2-fluoro-3-chloro benzoic acid as described in general procedure A. LCMS: m/e 570 [M+H].

Example 7

N-(3-Aminopropyl)-N-[1-(3-anilino-7-chloro-4-oxo-3,4-dihydroquinazolin-2-yl)propyl]-4-methylbenzamide (3)

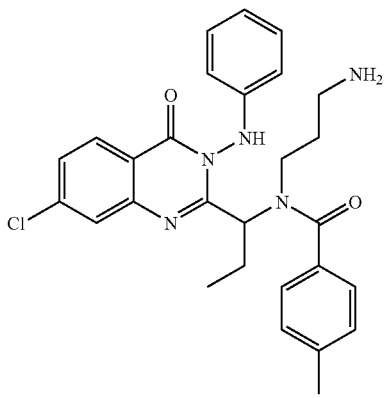

This product was synthesized as described in general procedure A, except N-Boc-DL-2-amino butyric acid was used instead of (R)-2-tert-butoxycarbonylamino-pent-4-ynoic acid and 4-methyl benzoic acid was used instead of 2-fluoro-3-chloro benzoic acid as described in general procedure A. LCMS: m/e 505 [M+H].

Example 8

N-(3-Aminopropyl)-N-[1-(3-anilino-7-chloro-4-oxo-3,4-dihydroquinazolin-2-yl)propyl]-4-chlorobenzamide (4)

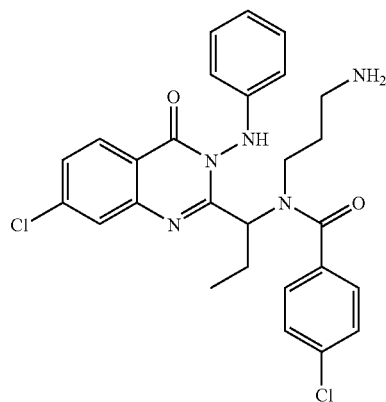

This product was synthesized as described in general procedure A, except N-Boc-DL-2-amino butyric acid was used instead of (R)-tert-butoxycarbonylamino-pent-4-ynoic acid and 4-chloro benzoic acid was used instead of 2-fluoro-3-chloro benzoic acid as described in general procedure A. LCMS: m/e 525 [M+H].

Example 9

N-(3-Aminopropyl)-N-[1-(3-anilino-7-chloro-4-oxo-3,4-dihydroquinazolin-2-yl)propyl]-4-nitrobenzamide (5)

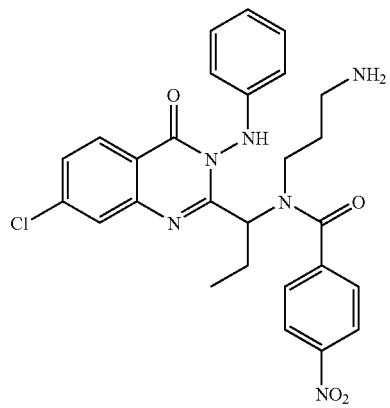

This product was synthesized as described in general procedure A, except N-Boc-DL-2-amino butyric acid was used instead of (R)-tert-butoxycarbonylamino-pent-4-ynoic acid and 4-nitro benzoic acid was used instead of 2-fluoro-3-chloro benzoic acid as described in general procedure A. LCMS: m/e 536 [M+H].

Example 10

N-(3-Aminopropyl)-N-[1-(3-anilino-7-chloro-4-oxo-3,4-dihydroquinazolin-2-yl)propyl]-3,4-dichlorobenzamide (6)

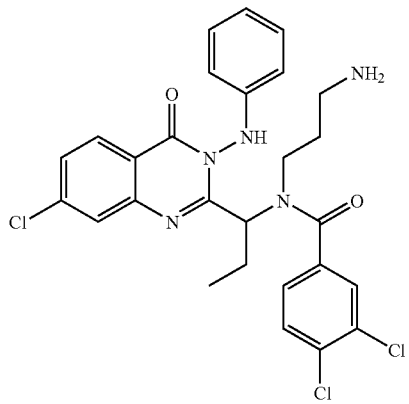

This compound was synthesized as described in general procedure A, except N-Boc-DL-2-amino butyric acid was used instead of (R)-tert-butoxycarbonylamino-pent-4-ynoic acid and 3,4-dichloro benzoic acid was used instead of 2-fluoro-3-chloro benzoic acid as described in general procedure A. LCMS: m/e 559 [M+H].

Example 11

N-(3-Aminopropyl)-N-[1-(3-anilino-7-chloro-4-oxo-3,4-dihydroquinazolin-2-yl)propyl]-2,3-difluorobenzamide (7)

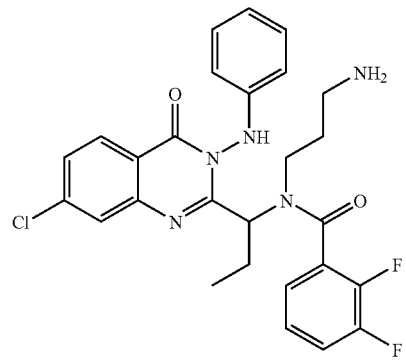

This compound was synthesized as described in general procedure A, except N-Boc-DL-2-amino butyric acid was used instead of (R)-tert-butoxycarbonylamino-pent-4-ynoic acid and 2,3-difluoro benzoic acid was used instead of 2-fluoro-3-chloro benzoic acid as described in general procedure A. LCMS: m/e 527 [M+H].

Example 12

N-(3-Aminopropyl)-N-[1-(3-anilino-7-chloro-4-oxo-3,4-dihydroquinazolin-2-yl)propyl]-4-fluorobenzamide (8)

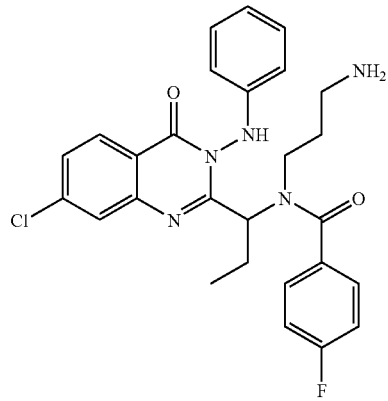

This compound was synthesized as described in general procedure A, except N-Boc-DL-2-amino butyric acid was used instead of (R)-tert-butoxycarbonylamino-pent-4-ynoic acid and 4-fluoro benzoic acid was used instead of 2-fluoro-3-chloro benzoic acid as described in general procedure A. LCMS: m/e 509 [M+H].

Example 13

N-(3-Aminopropyl)-N-[1-(3-anilino-7-chloro-4-oxo-3,4-dihydroquinazolin-2-yl)propyl]-3,4-difluorobenzamide (9)

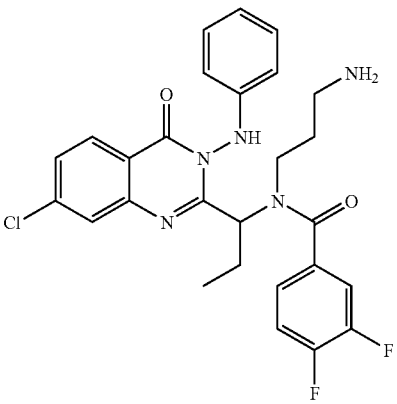

This compound was synthesized as described in general procedure A, except N-Boc-DL-2-amino butyric acid was used instead of (R)-tert-butoxycarbonylamino-pent-4-ynoic acid and 3,4-difluoro benzoic acid was used instead of 2-fluoro-3-chloro benzoic acid as described in general procedure A. LCMS: m/e 527 [M+H].

Example 14

N-(3-Aminopropyl)-N-[1-(3-anilino-7-chloro-4-oxo-3,4-dihydroquinazolin-2-yl)propyl]-2,3,4-trifluorobenzamide (10)

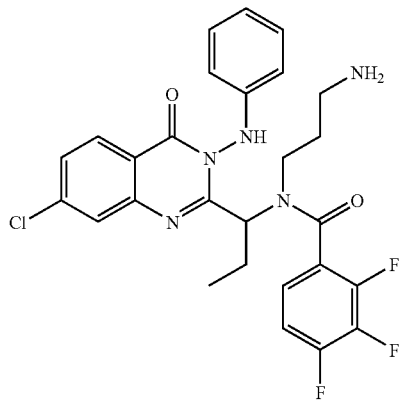

This compound was synthesized as described in general procedure A, except N-Boc-DL-2-amino butyric acid was used instead of (R)-tert-butoxycarbonylamino-pent-4-ynoic acid and 2,3,4-trifluoro benzoic acid was used instead of 2-fluoro-3-chloro benzoic acid as described in general procedure A. LCMS: m/e 545 [M+H].

Example 15

N-(3-Aminopropyl)-N-[1-(3-anilino-7-chloro-4-oxo-3,4-dihydroquinazolin-2-yl)propyl]-3,5-dichlorobenzamide (11)

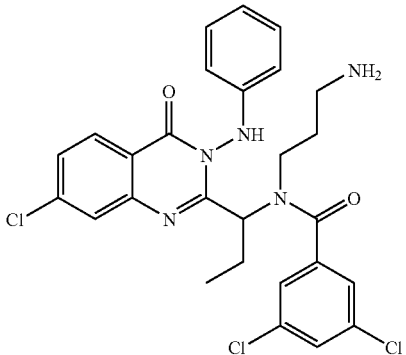

This compound was synthesized as described in general procedure A, except N-Boc-DL-2-amino butyric acid was used instead of (R)-tert-butoxycarbonylamino-pent-4-ynoic acid and 3,5-dichloro benzoic acid was used instead of 2-fluoro-3-chloro benzoic acid as described in general procedure A. LCMS: m/e 560 [M+H].

Example 16

N-(3-Aminopropyl)-N-[1-(3-anilino-7-chloro-4-oxo-3,4-dihydroquinazolin-2-yl)propyl]-2,3-dichlorobenzamide (12)

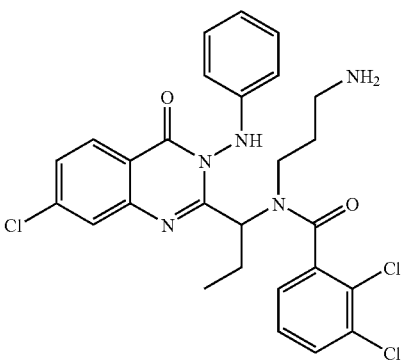

This compound was synthesized as described in general procedure A, except N-Boc-DL-2-amino butyric acid was used instead of (R)-tert-butoxycarbonylamino-pent-4-ynoic acid and 2,3-dichloro benzoic acid was used instead of 2-fluoro-3-chloro benzoic acid as described in general procedure A. LCMS: m/e 560 [M+H].

Example 17

N-(3-Aminopropyl)-N-[1-(3-anilino-7-chloro-4-oxo-3,4-dihydroquinazolin-2-yl)propyl]-3-chloro-4-fluorobenzamide (13)

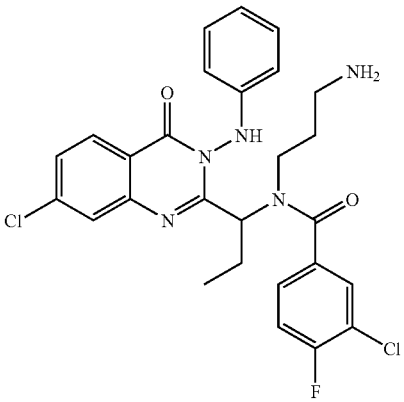

This compound was synthesized as described in general procedure A, except N-Boc-DL-2-amino butyric acid was used instead of (R)-tert-butoxycarbonylamino-pent-4-ynoic acid and 3-chloro-4-fluoro benzoic acid was used instead of 2-fluoro-3-chloro benzoic acid as described in general procedure A. LCMS: m/e 543 [M+H].

Example 18

N-(3-Aminopropyl)-N-[1-(3-anilino-7-chloro-4-oxo-3,4-dihydroquinazolin-2-yl)propyl]-3-bromobenzamide (14)

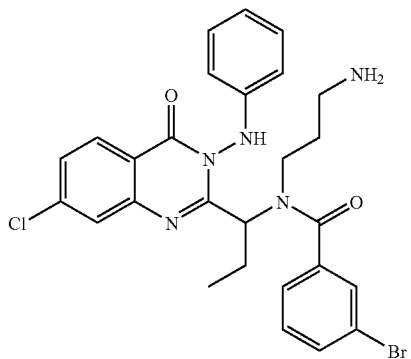

This compound was synthesized as described in general procedure A, except N-Boc-DL-2-amino butyric acid was used instead of (R)-tert-butoxycarbonylamino-pent-4-ynoic acid and 3-bromo benzoic acid was used instead of 2-fluoro-3-chloro benzoic acid as described in general procedure A. LCMS: m/e 570 [M+H].

Example 19

N-(3-Aminopropyl)-N-[1-(3-anilino-7-chloro-4-oxo-3,4-dihydroquinazolin-2-yl)propyl]-4-iodobenzamide (15)

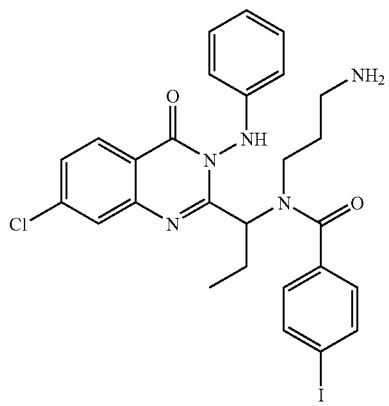

This compound was synthesized as described in general procedure A, except N-Boc-DL-2-amino butyric acid was used instead of (R)-tert-butoxycarbonylamino-pent-4-ynoic acid and 4-iodo benzoic acid was used instead of 2-fluoro-3-chloro benzoic acid as described in general procedure A. LCMS: m/e 617 [M+H].

Example 20

N-(3-Aminopropyl)-N-[1-(3-anilino-7-chloro-4-oxo-3,4-dihydroquinazolin-2-yl)propyl]-3-fluoro-4-methylbenzamide (16)

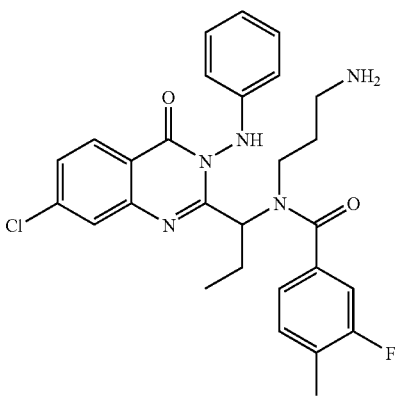

This compound was synthesized as described in general procedure A, except N-Boc-DL-2-amino butyric acid was used instead of (R)-tert-butoxycarbonylamino-pent-4-ynoic acid and 3-fluoro-4-methyl benzoic acid was used instead of 2-fluoro-3-chloro benzoic acid as described in general procedure A. LCMS: m/e 523 [M+H].

Example 21

N-(3-Aminopropyl)-N-[1-(3-anilino-7-chloro-4-oxo-3,4-dihydroquinazolin-2-yl)propyl]-2,6-difluoro-3-methylbenzamide (17)

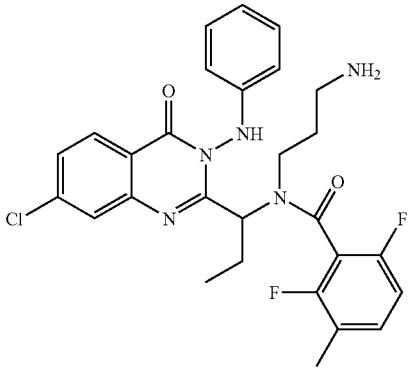

This compound was synthesized as described in "general procedure A," except N-Boc-DL-2-amino butyric acid was used instead of (R)-tert-butoxycarbonylamino-pent-4-ynoic acid and 2,6-difluoro-3-methyl benzoic acid was used instead of 2-fluoro-3-chloro benzoic acid as described in general procedure A. LCMS: m/e 541 [M+H].

Example 22

N-(3-Aminopropyl)-N-[1-(3-anilino-7-chloro-4-oxo-3,4-dihydroquinazolin-2-yl)propyl]-4-fluoro-3-methylbenzamide (18)

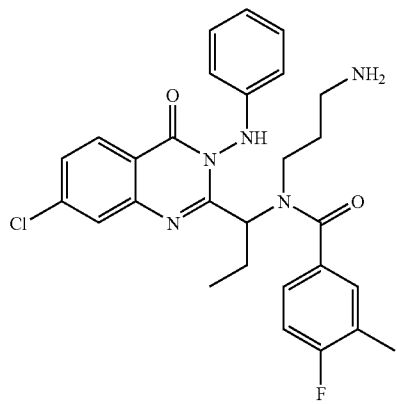

This compound was synthesized as described in "general procedure A," except N-Boc-DL-2-amino butyric acid was used instead of (R)-tert-butoxycarbonylamino-pent-4-ynoic acid and 4-fluoro-3-methyl benzoic acid was used instead of 2-fluoro-3-chloro benzoic acid as described in general procedure A. LCMS: m/e 523 [M+H].

Example 23

N-(3-Aminopropyl)-N-[1-(3-anilino-7-chloro-4-oxo-3,4-dihydroquinazolin-2-yl)propyl]-3-chloro-2-fluorobenzamide (19)

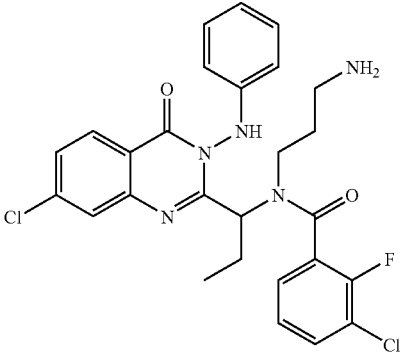

This compound was synthesized as described in "general procedure A," except N-Boc-DL-2-amino butyric acid was used instead of (R)-tert-butoxycarbonylamino-pent-4-ynoic acid as described in general procedure A. LCMS: m/e 543 [M+H].

Example 24

N-(3-Aminopropyl)-N-[1-(3-anilino-7-chloro-4-oxo-3,4-dihydroquinazolin-2-yl)propyl]-3-chloro-2,4-difluorobenzamide (20)

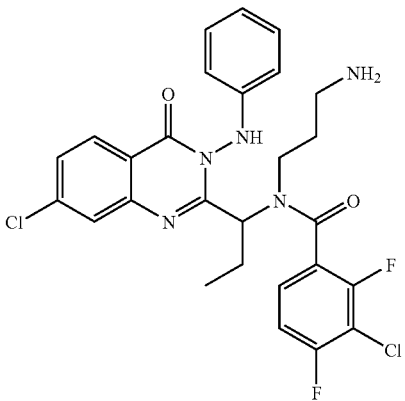

This compound was synthesized as described in "general procedure A," except N-Boc-DL-2-amino butyric acid was used instead of (R)-tert-butoxycarbonylamino-pent-4-ynoic acid and 3-chloro-2,4-difluoro benzoic acid was used instead of 2-fluoro-3-chloro benzoic acid as described in general procedure A. LCMS: m/e 561 [M+H].

Example 25

N-(3-Aminopropyl)-N-[1-(3-anilino-7-chloro-4-oxo-3,4-dihydroquinazolin-2-yl)propyl]-2,3-difluoro-4-methylbenzamide (21)

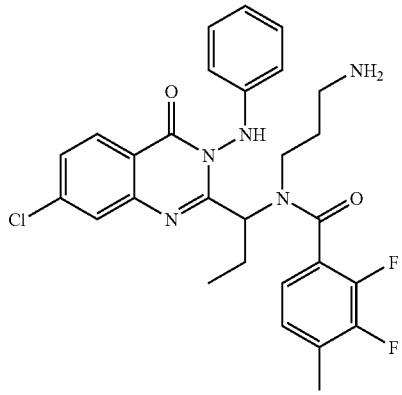

This compound was synthesized as described in "general procedure A," except N-Boc-DL-2-amino butyric acid was used instead of (R)-tert-butoxycarbonylamino-pent-4-ynoic acid and 2,3-difluoro-4-methyl benzoic acid was used instead

Example 26

N-(3-Aminopropyl)-N-[1-(3-anilino-7-chloro-4-oxo-3,4-dihydroquinazolin-2-yl)propyl]quinoline-2-carboxamide (22)

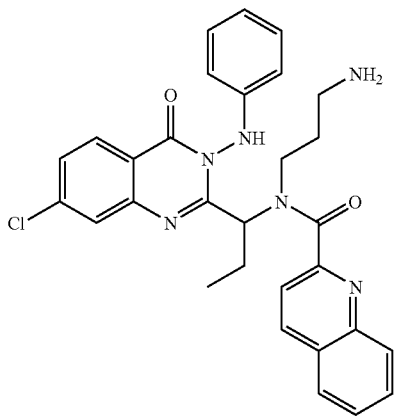

This compound was synthesized as described in "general procedure A," except N-Boc-DL-2-amino butyric acid was used instead of (R)-tert-butoxycarbonylamino-pent-4-ynoic acid and quinoline-2-carboxylic acid was used instead of 2-fluoro-3-chloro benzoic acid as described in general procedure A. LCMS: m/e 542 [M+H].

Example 27

N-(3-Aminopropyl)-N-[1-(3-anilino-7-chloro-4-oxo-3,4-dihydroquinazolin-2-yl)propyl]-4-(1H-pyrazol-1-yl)benzamide (23)

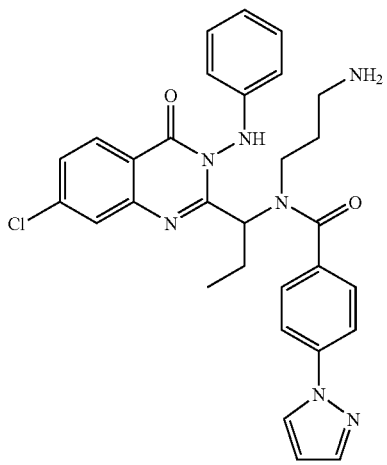

This compound was synthesized as described in "general procedure A," except N-Boc-DL-2-amino butyric acid was used instead of (R)-tert-butoxycarbonylamino-pent-4-ynoic acid and 4-pyrazole-yl benzoic acid was used instead of 2-fluoro-3-chloro benzoic acid as described in general procedure A. LCMS: m/e 541 [M+H].

Example 28

N-(3-Aminopropyl)-N-(1-{7-chloro-3-[(3-fluorophenyl)amino]-4-oxo-3,4-dihydroquinazolin-2-yl}propyl)-4-methylbenzamide (24)

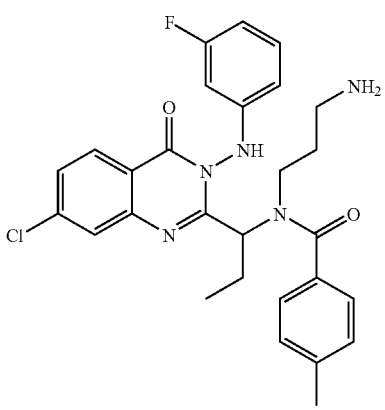

This compound was synthesized as described in "general procedure A," except 3-fluoro phenyl hydrazine was used instead of phenyl hydrazine, N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 523 [M+H].

Example 29

N-(3-Aminopropyl)-N-(1-{7-chloro-3-[(2-fluorophenyl)amino]-4-oxo-3,4-dihydroquinazolin-2-yl}propyl)-4-methylbenzamide (25)

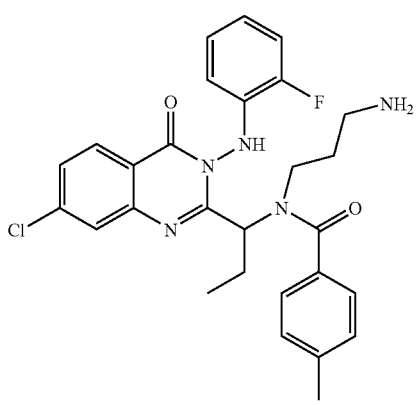

This compound was synthesized as described in "general procedure A," except 2-fluoro phenyl hydrazine was used instead of phenyl hydrazine, N-Boc-DL-2-amino butyric acid was used instead of (R)-tert-butoxycarbonylamino-pent-4-ynoic acid and 4-methyl benzoic acid was used instead of

Example 30

N-(3-Aminopropyl)-N-(1-{7-chloro-3-[(2,5-difluorophenyl)amino]-4-oxo-3,4-dihydroquinazolin-2-yl}propyl)-4-methylbenzamide (26)

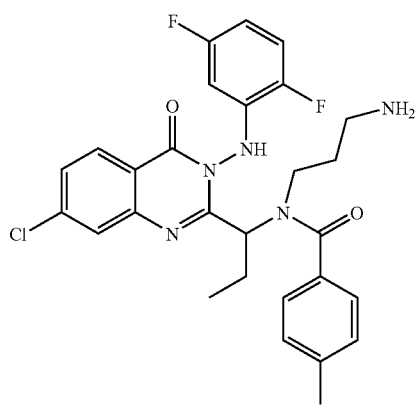

This compound was synthesized as described in "general procedure A," except 2,5-difluoro phenyl hydrazine was used instead of phenyl hydrazine, N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 541 [M+H].

Example 31

N-(3-Aminopropyl)-N-[1-(3-anilino-6-chloro-4-oxo-3,4-dihydroquinazolin-2-yl)propyl]-4-methylbenzamide (27)

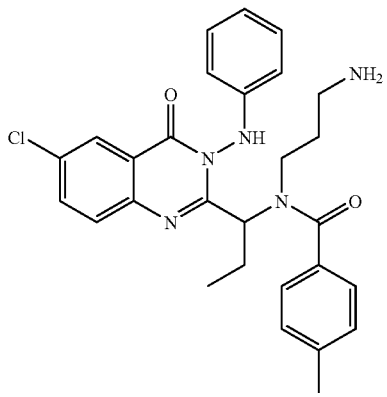

This compound was synthesized by using 2-amino-5-chloro benzoic acid instead of 2-amino-4-chloro benzoic acid as described in "general procedure A," and, N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 505 [M+H].

Example 32

N-(3-Aminopropyl)-N-[1-(3-anilino-6-methyl-4-oxo-3,4-dihydroquinazolin-2-yl)propyl]-4-methylbenzamide (28)

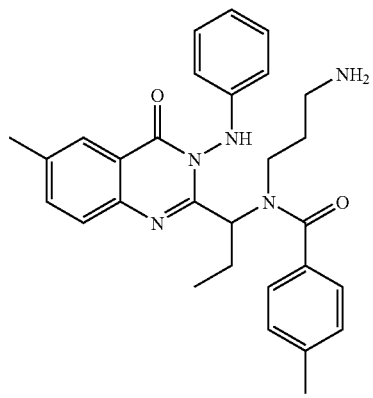

This compound was synthesized by using 2-amino-5-methyl benzoic acid instead of 2-amino-4-chloro benzoic acid as described in "general procedure A," and N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 484 [M+H].

Example 33

N-(3-Aminopropyl)-N-[1-(7-chloro-4-oxo-3-phenoxy-3,4-dihydroquinazolin-2-yl)propyl]-4-methylbenzamide (29)

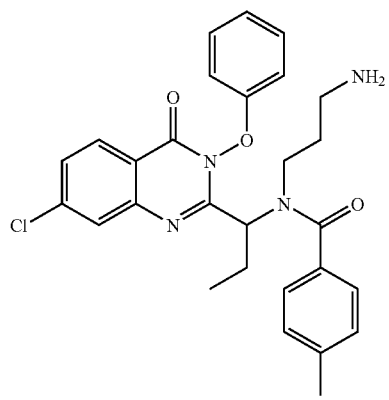

This compound was synthesized by using O-phenyl hydroxylamine instead of phenyl hydrazine in procedure as described in "general procedure A,", N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 506 [M+H].

Example 34

General Procedure B

Sulfonylation of 2-{3-[(R)-1-(7-chloro-4-oxo-3-phenylamino-3,4-dihydro-quinazolin-2-yl)-but-3-ynylamino]-propyl}-isoindole-1,3-dione followed by deprotection.

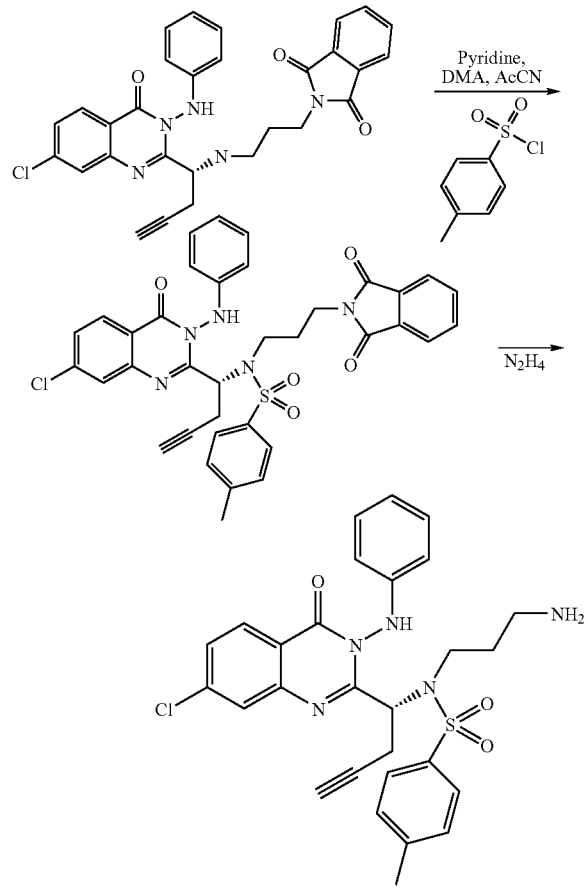

Example 35

Synthesis of N-(3-amino-propyl)-N-[(R)-1-(7-chloro-4-oxo-3-phenylamino-3,4-dihydro-quinazolin-2-yl)-but-3-ynyl]-4-methyl-benzenesulfonamide (30)

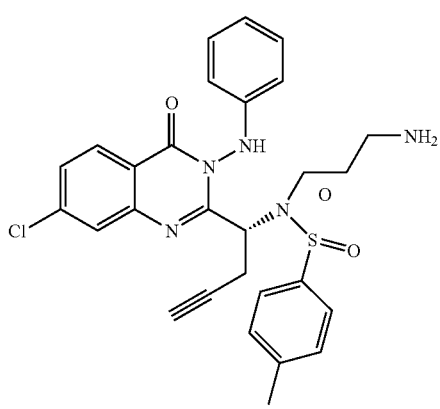

A solution of 2-{3-[(R)-1-(7-chloro-4-oxo-3-phenylamino-3,4-dihydro-quinazolin-2-yl)-but-3-ynylamino]-propyl}-isoindole-1,3-dione (52.6 mg, 0.10 μmol) in pyridine (0.5 mL) was treated with respective sulfonyl chloride (in this case 4-methyl benzenesulfonyl chloride, 0.25M solution in DMA/AcCN (1:1), 0.5 mL, 0.125 μmol). The mixture was stirred at 45° C. for 24 h. Solvent was removed under reduced pressure. Residue was taken in MeOH (1.0 mL) and treated with hydrazine (0.25 mL). Reaction mixture was stirred at room temperature for 16 h and solvent removed under reduced pressure. The product was purified with reverse phase chromatography to give final product. Yield (10.4 mg, 20%). LCMS: m/e 551 [M+H].

Example 36

N-(3-Aminopropyl)-N-[(1R)-1-(3-anilino-7-chloro-4-oxo-3,4-dihydroquinazolin-2-yl)propyl]-3-fluorobenzenesulfonamide (31)

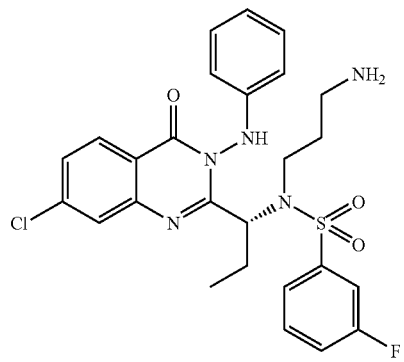

This compound was synthesized as described in "general procedure A," except N-Boc-D-2-amino butyric acid was used instead of (R)-tert-butoxycarbonylamino-pent-4-ynoic acid and 3-fluoro benzenesulfonyl chloride was used as described in general procedure B. LCMS: m/e 545 [M+H].

Example 37

N-(3-Aminopropyl)-N-{1-[3-(benzyloxy)-7-chloro-4-oxo-3,4-dihydroquinazolin-2-yl]propyl}-4-methylbenzamide (32)

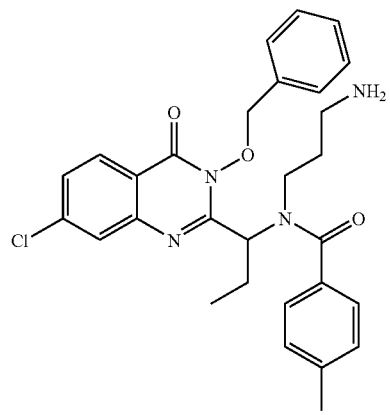

This compound was synthesized by using O-benzyl hydroxylamine instead of phenyl hydrazine as described in "general procedure A," except N-Boc-DL-2-amino butyric acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 520 [M+H].

Example 38

N-(3-Aminopropyl)-N-[(1R)-1-(3-anilino-7-chloro-4-oxo-3,4-dihydroquinazolin-2-yl)propyl]-1,3,5-trimethyl-1H-pyrazole-4-sulfonamide (33)

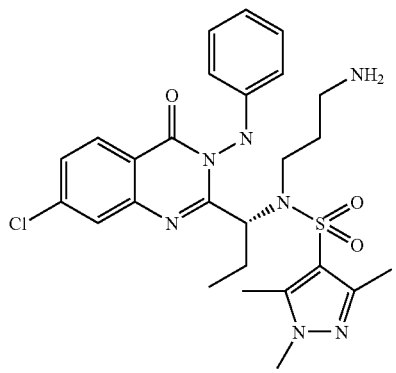

This compound was synthesized as described in "general procedure A," except N-Boc-D-2-amino butyric acid was used instead of (R)-tert-butoxycarbonylamino-pent-4-ynoic acid and 1,3,5-trimethyl-1H-pyrazole-4-sulfonyl chloride was used as described in general procedure B. LCMS: m/e 559 [M+H].

Example 39

N-(3-Aminopropyl)-N-[(1R)-1-(3-anilino-7-chloro-4-oxo-3,4-dihydroquinazolin-2-yl)propyl]thiophene-3-sulfonamide (34)

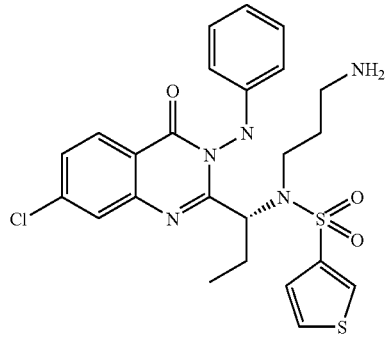

This compound was synthesized as described in "general procedure A," except N-Boc-D-2-amino butyric acid was used instead of (R)-tert-butoxycarbonylamino-pent-4-ynoic acid and thiophene-3-sulfonyl chloride was as described in general procedure B. LCMS: m/e 533 [M+H].

Example 40

N-(3-Aminopropyl)-N-[1-(3-anilino-7-chloro-4-oxo-3,4-dihydroquinazolin-2-yl)-3-methylbutyl]-3,4-difluorobenzamide (35)

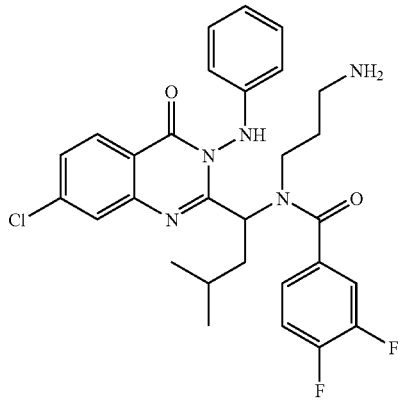

This compound was synthesized as described in general procedure A, except N-Boc-DL-leucine was used instead of (R)-tert-butoxycarbonylamino-pent-4-ynoic acid and 3,4-difluoro benzoic acid was used instead of 2-fluoro-3-chloro benzoic acid as described in general procedure A. LCMS: m/e 555 [M+H].

Example 41

N-(3-Aminopropyl)-N-[1-(3-anilino-7-chloro-4-oxo-3,4-dihydroquinazolin-2-yl)-3-methylbutyl]-3,5-dichlorobenzamide (36)

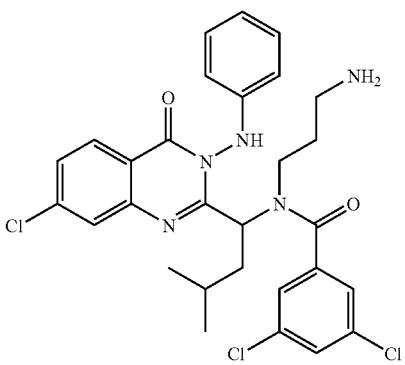

This compound was synthesized as described in general procedure A, except N-Boc-DL-leucine was used instead of (R)-tert-butoxycarbonylamino-pent-4-ynoic acid and 3,5-dichloro benzoic acid was used instead of 2-fluoro-3-chloro benzoic acid as described in general procedure A. LCMS: m/e 588 [M+H].

Example 42

N-(3-Aminopropyl)-N-[1-(3-anilino-7-chloro-4-oxo-3,4-dihydroquinazolin-2-yl)-3-methylbutyl]-3-chloro-4-fluorobenzamide (37)

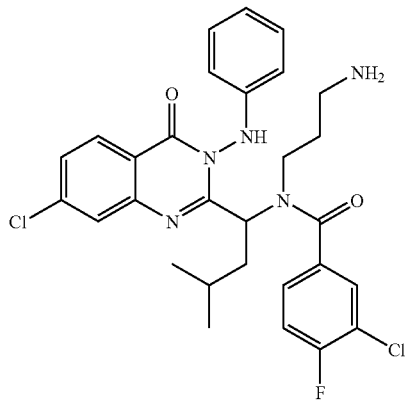

This compound was synthesized as described in general procedure A, except N-Boc-DL-leucine was used instead of (R)-tert-butoxycarbonylamino-pent-4-ynoic acid and 3-chloro-4-fluoro benzoic acid was used instead of 2-fluoro-3-chloro benzoic acid as described in general procedure A. LCMS: m/e 571 [M+H].

Example 43

N-(3-Aminopropyl)-N-[1-(3-anilino-7-chloro-4-oxo-3,4-dihydroquinazolin-2-yl)-3-(methylthio)propyl]-3-chloro-2-fluorobenzamide (38)

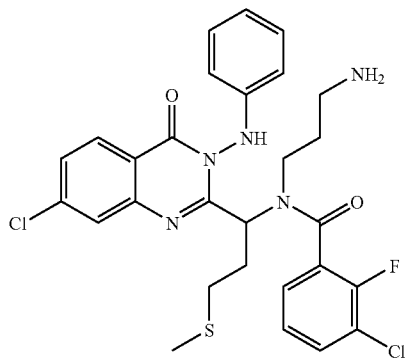

This compound was synthesized as described in general procedure A, except N-Boc-DL-methionine was used instead of (R)-tert-butoxycarbonylamino-pent-4-ynoic acid as described in general procedure A. LCMS: m/e 589 [M+H].

Example 44

N-(3-Aminopropyl)-N-[1-(3-anilino-7-chloro-4-oxo-3,4-dihydroquinazolin-2-yl)-3-(methylthio)propyl]-2,3-difluoro-4-methylbenzamide (39)

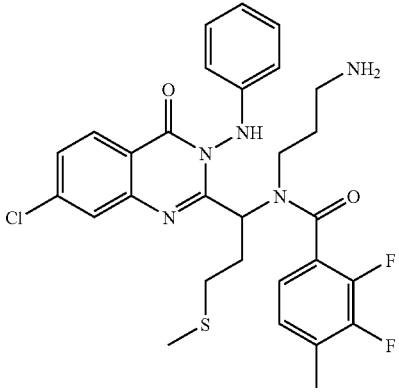

This compound was synthesized as described in general procedure A, except N-Boc-DL-methionine was used instead of (R)-tert-butoxycarbonylamino-pent-4-ynoic acid and 2,3-difluoro-4-methyl benzoic acid was used instead of 2-fluoro-3-chloro benzoic acid as described in general procedure A. LCMS: m/e 587 [M+H].

Example 45

N-(3-Aminopropyl)-N-[1-(3-anilino-7-chloro-4-oxo-3,4-dihydroquinazolin-2-yl)-3-(methylthio)propyl]-4-(1H-pyrazol-1-yl)benzamide (40)

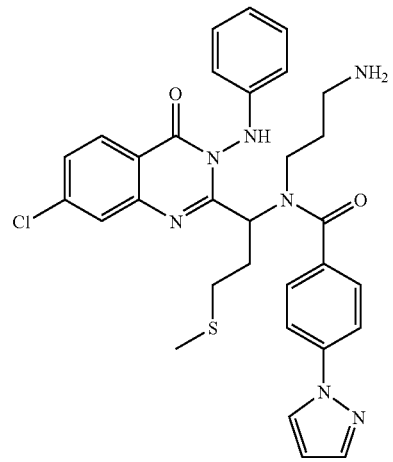

This compound was synthesized as described in general procedure A, except N-Boc-DL-methionine was used instead of (R)-tert-butoxycarbonylamino-pent-4-ynoic acid and 4-pyrazol-1-yl-benzoic acid was used instead of 2-fluoro-3-chloro benzoic acid as described in general procedure A. LCMS: m/e 603 [M+H].

Example 46

N-(3-Aminopropyl)-N-[1-(3-anilino-7-chloro-4-oxo-3,4-dihydroquinazolin-2-yl)ethyl]-3,4-dichlorobenzamide (41)

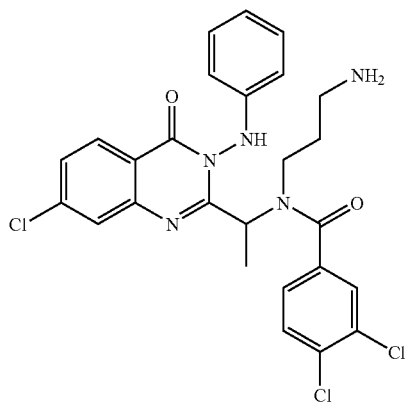

This compound was synthesized as described in general procedure A, except N-Boc-DL-alanine was used instead of (R)-tert-butoxycarbonylamino-pent-4-ynoic acid and 3,4-dichloro-benzoic acid was used instead of 2-fluoro-3-chloro benzoic acid as described in general procedure A. LCMS: m/e 546 [M+H].

Example 47

N-(3-Aminopropyl)-N-[1-(3-anilino-7-chloro-4-oxo-3,4-dihydroquinazolin-2-yl)-2-methylpropyl]-2,3-difluorobenzamide (42)

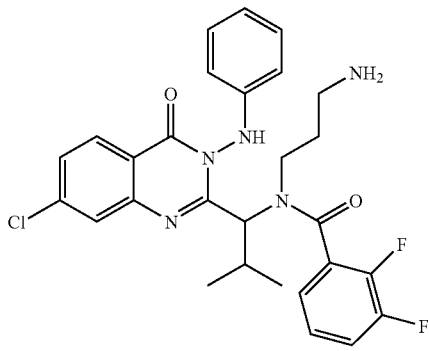

This compound was synthesized as described in general procedure A, except N-Boc-DL-valine was used instead of (R)-tert-butoxycarbonylamino-pent-4-ynoic acid and 2,3-difluoro-benzoic acid was used instead of 2-fluoro-3-chloro benzoic acid as described in general procedure A. LCMS: m/e 541 [M+H].

Example 48

N-(3-Aminopropyl)-N-[1-(3-anilino-7-chloro-4-oxo-3,4-dihydroquinazolin-2-yl)-2-methylpropyl]-4-fluorobenzamide (43)

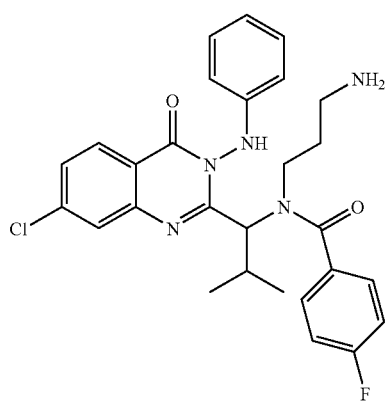

This compound was synthesized as described in general procedure A, except N-Boc-DL-valine was used instead of (R)-tert-butoxycarbonylamino-pent-4-ynoic acid and 4-fluoro-benzoic acid was used instead of 2-fluoro-3-chloro benzoic acid as described in general procedure A. LCMS: m/e 523 [M+H].

Example 49

N-(3-Aminopropyl)-N-[1-(3-anilino-7-chloro-4-oxo-3,4-dihydroquinazolin-2-yl)-2-methylpropyl]-3-bromobenzamide (44)

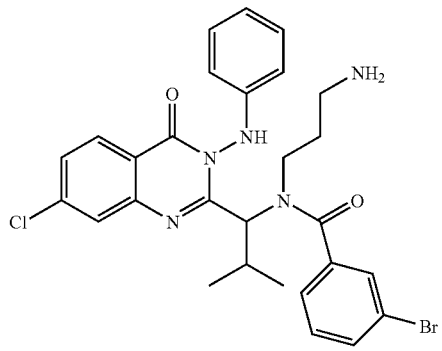

This compound was synthesized as described in general procedure A, except N-Boc-DL-valine was used instead of (R)-tert-butoxycarbonylamino-pent-4-ynoic acid and 3-bromo-benzoic acid was used instead of 2-fluoro-3-chloro benzoic acid as described in general procedure A. LCMS: m/e 584 [M+H].

Example 50

N-(3-Aminopropyl)-N-1-(3-anilino-7-chloro-4-oxo-3,4-dihydroquinazolin-2-yl)-2-methylpropyl]-4-chloro-2,5-difluorobenzamide (45)

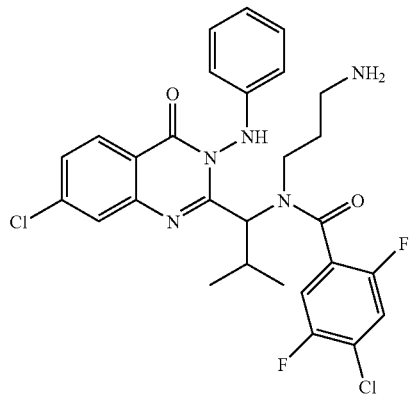

This compound was synthesized as described in general procedure A, except N-Boc-DL-valine was used instead of (R)-tert-butoxycarbonylamino-pent-4-ynoic acid and 2,5-difluoro-4-chloro benzoic acid was used instead of 2-fluoro-3-chloro benzoic acid as described in general procedure A. LCMS: m/e 575 [M+H].

Example 51

N-(3-Aminopropyl)-N-[1-(3-anilino-7-chloro-4-oxo-3,4-dihydroquinazolin-2-yl)-2-methylpropyl]-3-fluoro-4-methylbenzamide (46)

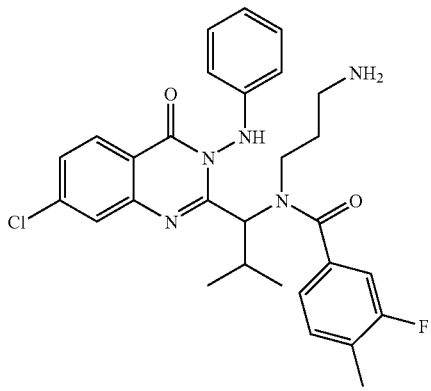

This compound was synthesized as described in general procedure A, except N-Boc-DL-valine was used instead of (R)-tert-butoxycarbonylamino-pent-4-ynoic acid and 3-fluoro-4-methyl benzoic acid was used instead of 2-fluoro-3-chloro benzoic acid as described in general procedure A. LCMS: m/e 537 [M+H].

Example 52

N-(3-Aminopropyl)-N-[1-(3-anilino-7-chloro-4-oxo-3,4-dihydroquinazolin-2-yl)-2-methylpropyl]quinoline-2-carboxamide (47)

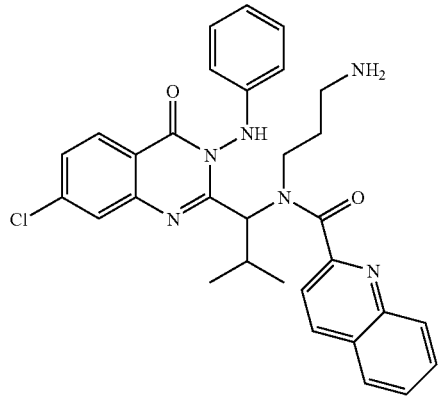

This compound was synthesized as described in general procedure A, except N-Boc-DL-valine was used instead of (R)-tert-butoxycarbonylamino-pent-4-ynoic acid and quinoline-2-carboxylic acid was used instead of 2-fluoro-3-chloro benzoic acid as described in general procedure A. LCMS: m/e 556 [M+H].

Example 53

N-(3-Aminopropyl)-N-[1-(3-anilino-7-chloro-4-oxo-3,4-dihydroquinazolin-2-yl)-2-(2-thienyl)ethyl]-4-bromobenzamide (48)

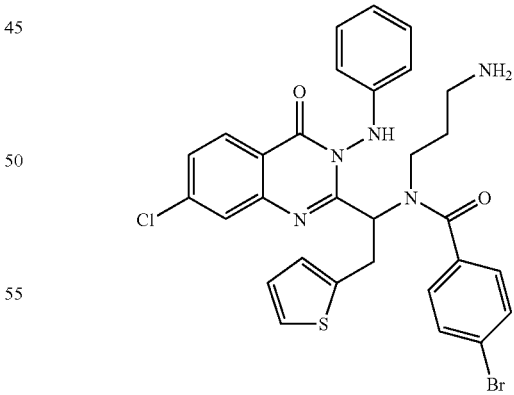

This compound was synthesized as described in general procedure A, except N-Boc-beta-(2-thienyl)-DL-alanine was used instead of (R)-tert-butoxycarbonylamino-pent-4-ynoic acid and 4-bromo benzoic acid was used instead of 2-fluoro-3-chloro benzoic acid as described in general procedure A. LCMS: m/e 638 [M+H].

Example 54

N-(3-Aminopropyl)-N-[1-(3-anilino-7-chloro-4-oxo-3,4-dihydroquinazolin-2-yl)-2-(2-thienyl)ethyl]-4-methylbenzamide (49)

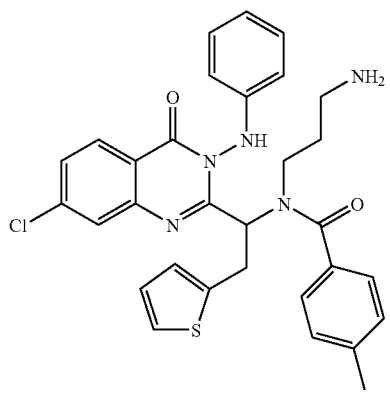

This compound was synthesized as described in general procedure A, except N-Boc-beta-(2-thienyl)-DL-alanine was used instead of (R)-tert-butoxycarbonylamino-pent-4-ynoic acid and 4-methyl benzoic acid was used instead of 2-fluoro-3-chloro benzoic acid as described in general procedure A. LCMS: m/e 573 [M+H].

Example 55

N-(3-Aminopropyl)-N-[1-(3-anilino-7-chloro-4-oxo-3,4-dihydroquinazolin-2-yl)-2-(2-thienyl)ethyl]-2,3-difluorobenzamide (50)

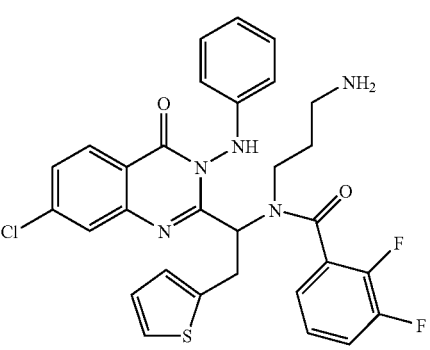

This compound was synthesized as described in general procedure A, except N-Boc-beta-(2-thienyl)-DL-alanine was used instead of (R)-tert-butoxycarbonylamino-pent-4-ynoic acid and 2,3-difluoro benzoic acid was used instead of 2-fluoro-3-chloro benzoic acid as described in general procedure A. LCMS: m/e 595 [M+H].

Example 56

N-(3-Aminopropyl)-N-[1-(3-anilino-7-chloro-4-oxo-3,4-dihydroquinazolin-2-yl)-2-(2-thienyl)ethyl]-4-fluorobenzamide (51)

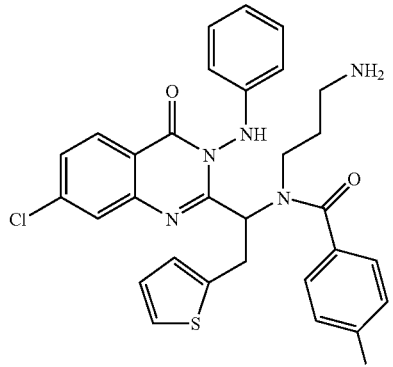

This compound was synthesized as described in general procedure A, except N-Boc-beta-(2-thienyl)-DL-alanine was used instead of (R)-tert-butoxycarbonylamino-pent-4-ynoic acid and 4-fluoro benzoic acid was used instead of 2-fluoro-3-chloro benzoic acid as described in general procedure A. LCMS: m/e 577 [M+H].

Example 57

N-(3-Aminopropyl)-N-[1-(3-anilino-7-chloro-4-oxo-3,4-dihydroquinazolin-2-yl)-2-(2-thienyl)ethyl]-3,4-difluorobenzamide (52)

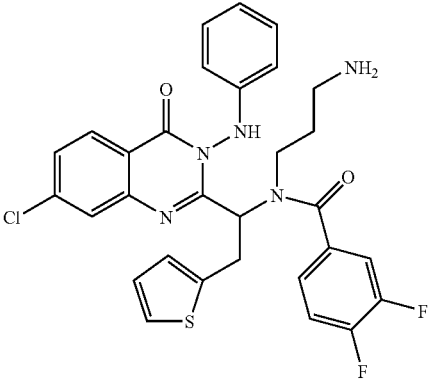

This compound was synthesized as described in general procedure A, except N-Boc-beta-(2-thienyl)-DL-alanine was used instead of (R)-tert-butoxycarbonylamino-pent-4-ynoic acid and 3,4-difluoro benzoic acid was used instead of 2-fluoro-3-chloro benzoic acid as described in general procedure A. LCMS: m/e 595 [M+H].

Example 58

N-(3-Aminopropyl)-N-[1-(3-anilino-7-chloro-4-oxo-3,4-dihydroquinazolin-2-yl)-2-(2-thienyl)ethyl]-3-chloro-4-fluorobenzamide (53)

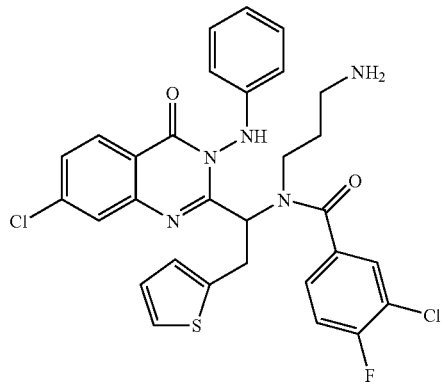

This compound was synthesized as described in general procedure A, except N-Boc-beta-(2-thienyl)-DL-alanine was used instead of (R)-tert-butoxycarbonylamino-pent-4-ynoic acid and 3-chloro-4-fluoro benzoic acid was used instead of 2-fluoro-3-chloro benzoic acid as described in general procedure A LCMS: m/e 611 [M+H]

Example 59

N-(3-Aminopropyl)-N-[1-(3-anilino-7-chloro-4-oxo-3,4-dihydroquinazolin-2-yl)-2-(4-hydroxyphenyl)ethyl]-3,4-dichlorobenzamide (54)

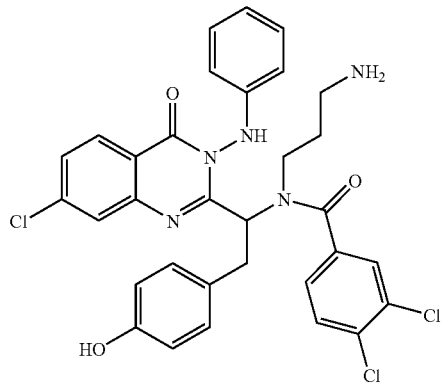

This compound was synthesized as described in general procedure A, except N-Boc-DL-tyrosine was used instead of (R)-tert-butoxycarbonylamino-pent-4-ynoic acid and 3,4-dichloro benzoic acid was used instead of 2-fluoro-3-chloro benzoic acid as described in general procedure A. LCMS: m/e 638 [M+H].

Example 60

N-(3-Aminopropyl)-N-[1-(3-anilino-7-chloro-4-oxo-3,4-dihydroquinazolin-2-yl)-2-(4-hydroxyphenyl)ethyl]-2,3,4-trifluorobenzamide (55)

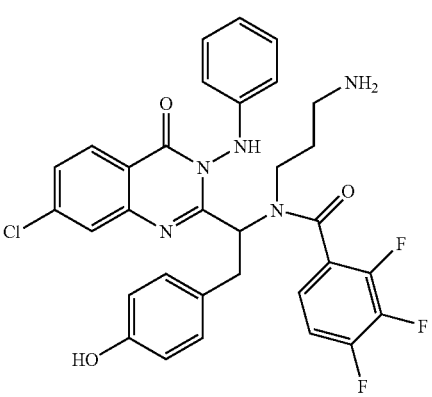

This compound was synthesized as described in general procedure A, except N-Boc-DL-tyrosine was used instead of (R)-tert-butoxycarbonylamino-pent-4-ynoic acid and 2,3,4-trifluoro benzoic acid was used instead of 2-fluoro-3-chloro benzoic acid as described in general procedure A. LCMS: m/e 623 [M+H].

Example 61

N-(3-Aminopropyl)-N-[1-(3-anilino-7-chloro-4-oxo-3,4-dihydroquinazolin-2-yl)but-3-yn-1-yl]-4-chloro-2,5-difluorobenzamide (56)

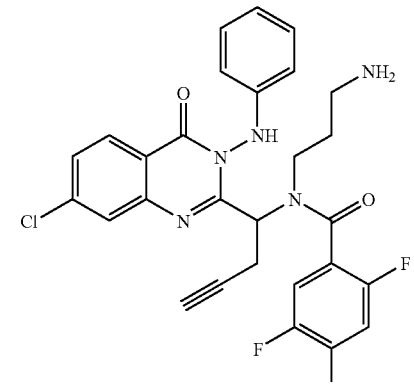

This compound was synthesized as described in general procedure A, except DL-tert-butoxycarbonylamino-pent-4-ynoic acid was used instead of (R)-tert-butoxycarbonylamino-pent-4-ynoic acid and 2,5-difluoro-4-chloro benzoic acid was used instead of 2-fluoro-3-chloro benzoic acid as described in general procedure A. LCMS: m/e 571 [M+H].

Example 62

N-(3-Aminopropyl)-N-[1-(3-anilino-7-chloro-4-oxo-3,4-dihydroquinazolin-2-yl)but-3-yn-1-yl]-3-chloro-2-fluorobenzamide (57)

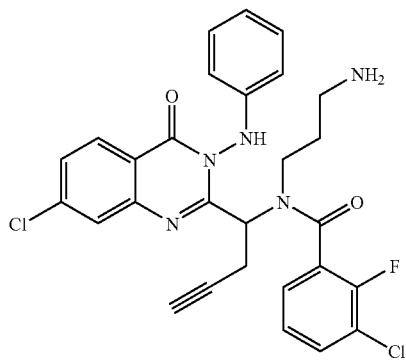

This compound was synthesized as described in general procedure A, except DL-tert-butoxycarbonylamino-pent-4-ynoic acid was used as described in general procedure A. LCMS: m/e 553 [M+H].

Example 63

N-(3-Aminopropyl)-N-[1-(3-anilino-7-chloro-4-oxo-3,4-dihydroquinazolin-2-yl)-3,3-dimethylbutyl]-4-bromobenzamide (58)

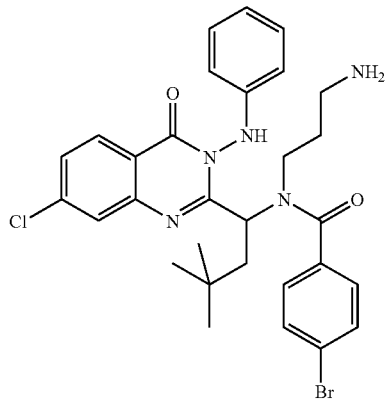

This compound was synthesized as described in general procedure A, except beta-tert butyl-N-Boc-DL-alanine was used instead of (R)-tert-butoxycarbonylamino-pent-4-ynoic acid and 4-bromo benzoic acid was used instead of 2-fluoro-3-chloro benzoic acid as described in general procedure A. LCMS: m/e 612 [M+H].

Example 64

N-(3-Aminopropyl)-N-[1-(3-anilino-7-chloro-4-oxo-3,4-dihydroquinazolin-2-yl)pentyl]-4-methylbenzamide (59)

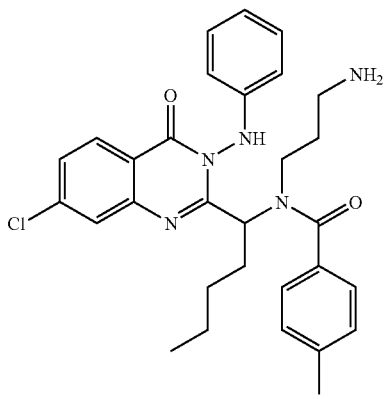

This compound was synthesized as described in general procedure A, except 2-amino hexanoic acid was used instead of (R)-tert-butoxycarbonylamino-pent-4-ynoic acid and 4-methyl benzoic acid was used instead of 2-fluoro-3-chloro benzoic acid as described in general procedure A. LCMS: m/e 533 [M+H].

Example 65

N-(2-Aminoethyl)-N-[1-(3-anilino-7-chloro-4-oxo-3,4-dihydroquinazolin-2-yl)propyl]-4-chlorobenzamide (60)

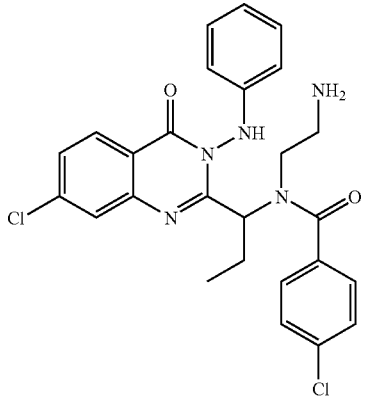

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde and 4-chloro benzoic acid was used instead of 2-fluoro-3-chloro benzoic acid as described in general procedure A. LCMS: m/e 511 [M+H].

Example 66

N-(2-Aminoethyl)-N-[1-(3-anilino-7-chloro-4-oxo-3,4-dihydroquinazolin-2-yl)propyl]-4-methylbenzamide (61)

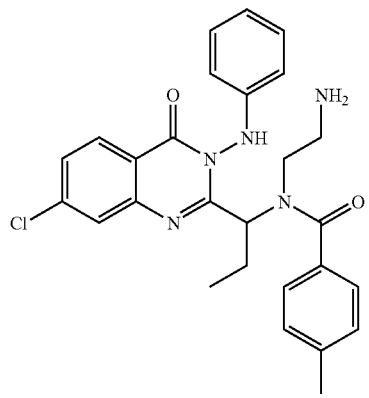

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde and 4-methyl benzoic acid was used instead of 2-fluoro-3-chloro benzoic acid as described in general procedure A LCMS: m/e 491 [M+H].

Example 67

N-(2-Aminoethyl)-N-[1-(3-anilino-7-chloro-4-oxo-3,4-dihydroquinazolin-2-yl)propyl]-2,6-difluoro-3-methylbenzamide (62)

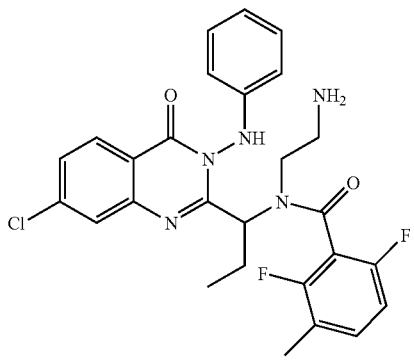

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde and 2,6-difluoro-3-methyl benzoic acid was used instead of 2-fluoro-3-chloro benzoic acid as described in general procedure A. LCMS: m/e 527 [M+H].

Example 68

N-(2-Aminoethyl)-N-[1-(3-anilino-7-chloro-4-oxo-3,4-dihydroquinazolin-2-yl)propyl]-4-fluoro-3-methylbenzamide (63)

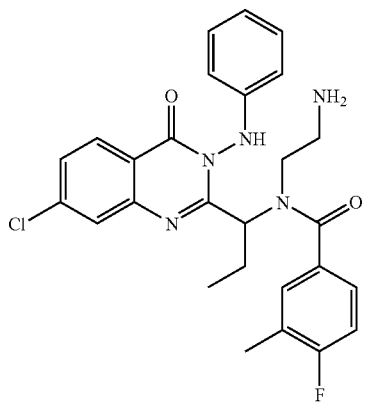

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde and 4-fluoro-3-methyl benzoic acid was used instead of 2-fluoro-3-chloro benzoic acid as described in general procedure A. LCMS: m/e 509 [M+H].

Example 69

N-(2-Aminoethyl)-N-[1-(3-anilino-7-chloro-4-oxo-3,4-dihydroquinazolin-2-yl)propyl]-3-chloro-2-fluorobenzamide (64)

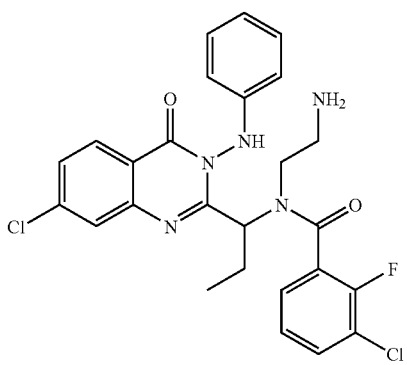

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde as described in general procedure A. LCMS: m/e 529 [M+H].

Example 70

N-(2-Aminoethyl)-N-[1-(3-anilino-7-chloro-4-oxo-3,4-dihydroquinazolin-2-yl)propyl]-2,3-difluoro-4-methylbenzamide (65)

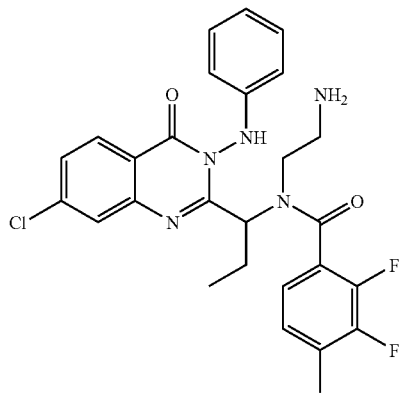

This compound was synthesized as described in general procedure A, except N-Boc-DL-2-amino butyric acid was used instead of (R)-tert-butoxycarbonylamino-pent-4-ynoic acid, (1,3-dioxo-1,3-dihydro-isoindol-2-yl)-acetaldehyde was used instead of 3-(1,3-dioxo-1,3-dihydro-isoindol-2-yl)-propionaldehyde and 2,3-difluoro-4-methyl benzoic acid was used instead of 2-fluoro-3-chloro benzoic acid as described in general procedure A. LCMS: m/e 527 [M+H].

Example 71

General Procedure C

Reductive amination of 2-{3-[(R)-1-(7-chloro-4-oxo-3-phenylamino-3,4-dihydro-quinazolin-2-yl)-but-3-ynylamino]-propyl}-isoindole-1,3-dione followed by deprotection.

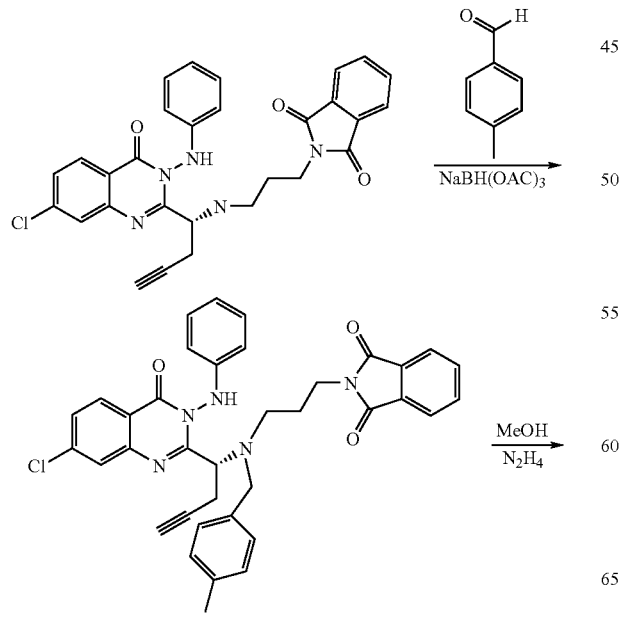

Example 72

2-{(R)-1-[(3-Amino-propyl)-(4-methyl-benzyl)-amino]-but-3-ynyl}-7-chloro-3-phenylamino-3H-quinazolin-4-one (66)

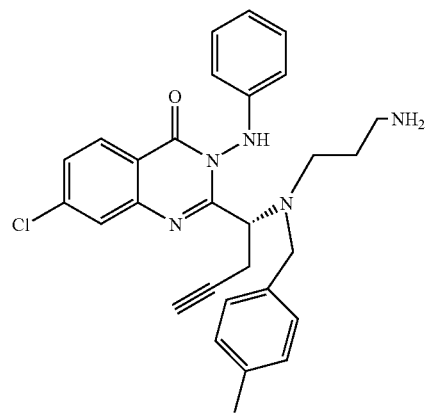

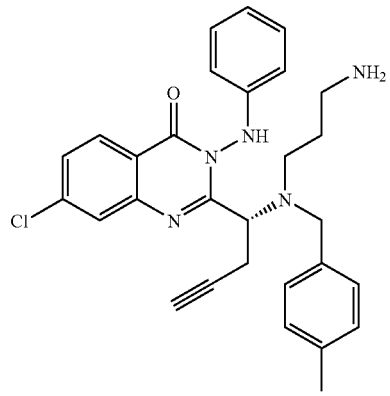

A solution of 2-{3-[(R)-1-(7-chloro-4-oxo-3-phenylamino-3,4-dihydro-quinazolin-2-yl)-but-3-ynylamino]-propyl}-isoindole-1,3-dione (52.6 mg, 0.10 μmol) in dichloroethane (0.5 mL) was treated with respective aldehydes (in this case 4-methyl benzaldehyde, 0.25M solution in DCE, 0.8 mL, 0.2 μmol). The mixture was stirred at room temperature for 16 h. Solvent was removed under reduced pressure. Residue was taken in MeOH (1.0 mL) and treated with hydrazine (0.25 mL). Reaction mixture was stirred at room temperature for 16 h and solvent removed under reduced pressure. The product was purified with reverse phase chromatography to give final product. Yield (14 mg, 24%). LCMS: m/e 500 [M+H].

Example 73

2-{1-[(3-Aminopropyl)(4-methyl-benzyl)amino]propyl}-3-anilino-7-chloro-3H-quinazolin-4-one (67)

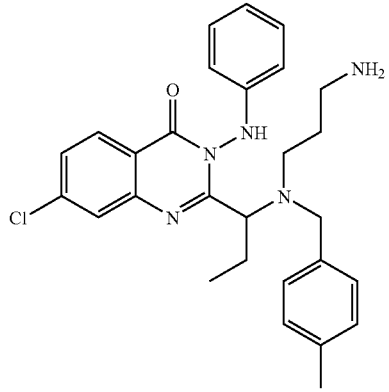

This compound was synthesized as described in general procedure C except 2-{3-[1-(7-chloro-4-oxo-3-phenylamino-3,4-dihydro-quinazolin-2-yl)-propylamino]-propyl}-isoindole-1,3-dione was used instead of (R)-2-(3-(1-(7-chloro-4-oxo-3-(phenylamino)-3,4-dihydroquinazolin-2-yl)but-3-ynylamino)propyl)isoindoline-1,3-dione. LCMS: m/e 491 [M+H].

Example 74

2-{(R)-1-[(3-Amino-propyl)-(4-methyl-benzyl)-amino]-propyl}-7-chloro-3-phenylamino-3H-quinazolin-4-one (68)

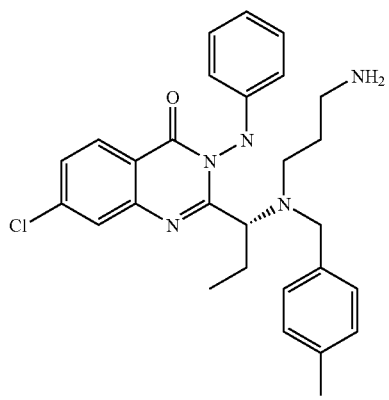

This compound was synthesized as described in general procedure C except 2-{3-[(R)-1-(7-chloro-4-oxo-3-phenylamino-3,4-dihydro-quinazolin-2-yl)-propylamino]-propyl}-isoindole-1,3-dione was used instead of (R)-2-(3-(1-(7-chloro-4-oxo-3-(phenylamino)-3,4-dihydroquinazolin-2-yl)but-3-ynylamino)propyl)isoindoline-1,3-dione. LCMS: m/e 491 [M+H].

Example 75

2-{(1R)-1-[(3-Aminopropyl)(4-fluoro-3-methylbenzyl)amino]propyl}-3-anilino-7-chloro-3H-quinazolin-4-one (69)

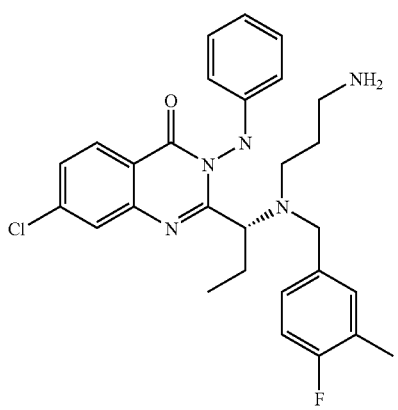

This compound was synthesized as described in general procedure C except 2-{3-[(R)-1-(7-chloro-4-oxo-3-phenylamino-3,4-dihydro-quinazolin-2-yl)-propylamino]-propyl}-isoindole-1,3-dione was used instead of (R)-2-(3-(1-(7-chloro-4-oxo-3-(phenylamino)-3,4-dihydroquinazolin-2-yl)but-3-ynylamino)propyl)isoindoline-1,3-dione and 4-fluoro-3-methyl benzaldehyde was used instead of 4-methyl benzaldehyde. LCMS: m/e 508.04 [M+H].

Example 76

2-{(1R)-1-[(3-aminopropyl)(benzyl)amino]propyl}-3-anilino-7-chloro-3H-quinazolin-4-one (70)

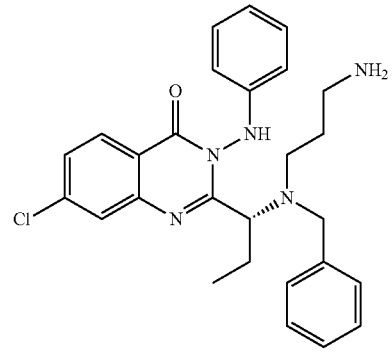

This compound was synthesized as described in general procedure C except 2-{3-[(R)-1-(7-chloro-4-oxo-3-phenylamino-3,4-dihydro-quinazolin-2-yl)-propylamino]-propyl}-isoindole-1,3-dione was used instead of (R)-2-(3-(1-(7-chloro-4-oxo-3-(phenylamino)-3,4-dihydroquinazolin-2-yl)but-3-ynylamino)propyl)isoindoline-1,3-dione and benzaldehyde was used instead of 4-methyl benzaldehyde. Yield (16%). LCMS: m/e 477.04 [M+H].

Example 77

General Procedure D; Synthesis of (R)-N-(3-aminopropyl)-3-chloro-N-(1-(7-chloro-4-oxo-3-(phenylamino)-3,4-dihydroquinazolin-2-yl)but-3-ynyl)-2-fluorobenzamide (1)

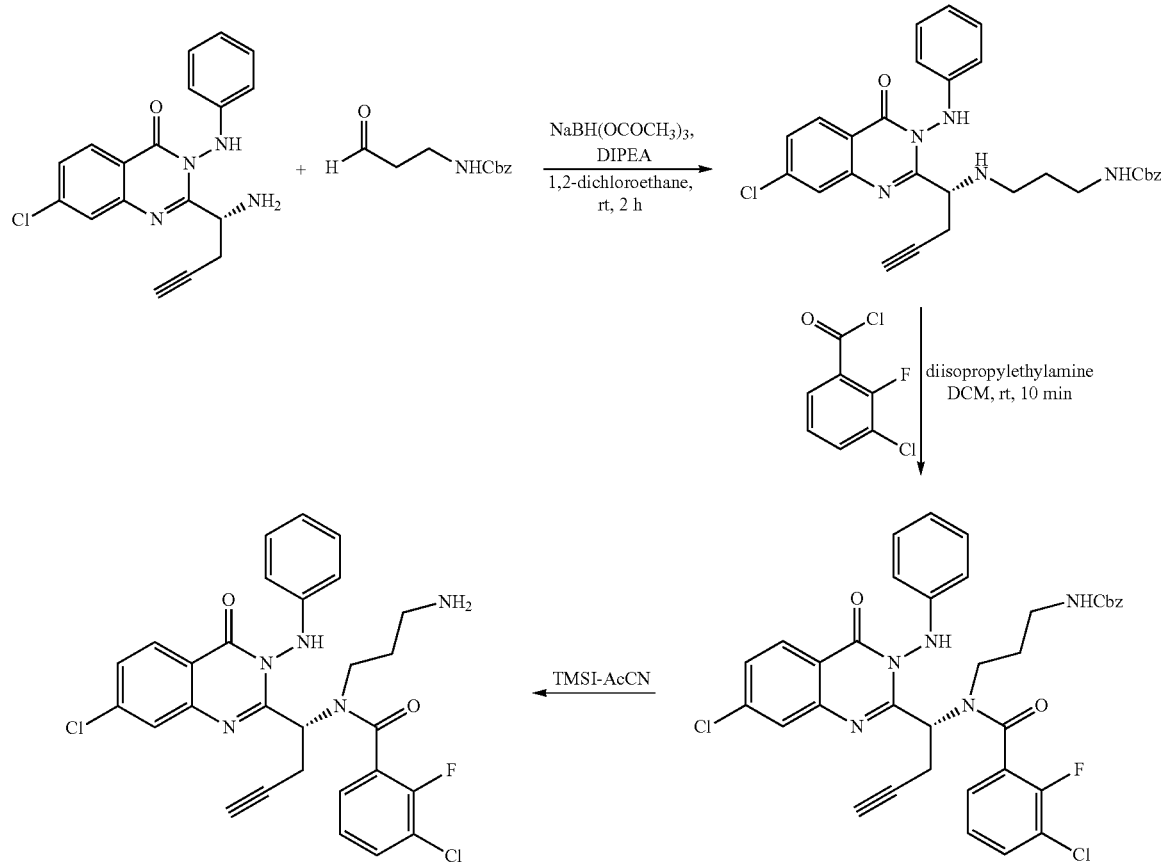

Example 78

(R)-benzyl 3-(1-(7-chloro-4-oxo-3-(phenylamino)-3,4-dihydroquinazolin-2-yl)but-3-ynylamino)propyl Carbamate

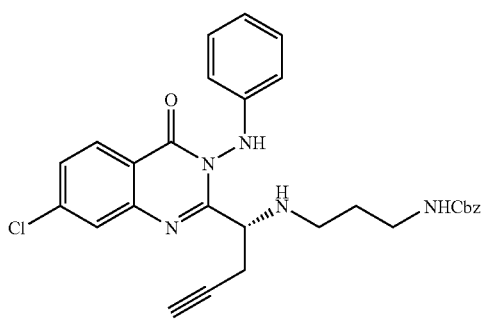

(R)-2-(1-Aminobut-3-ynyl)-7-chloro-3-(phenylamino)quinazolin-4(3H)-one (185 mg, 0.54 mmol) was dissolved in 1,2-dichloroethane (10 mL) and N,N-diisopropylethylamine (1.62 mmol) was added and stirred for 5 min where upon of 3-N-carbonyloxybenzyl propanaldehyde (0.59 mmol) and sodiumtriacetocyborohydride (1.18 mmol) were added and reaction was allowed to stir for 18 hours as LCMS showed presence of starting material after few hours. Upon completion, the reaction was quenched with sodium carbonate solution and extracted with 100 mL of dichloromethane and the organic layer was dried over sodium sulfate. Removal of solvent under reduced pressure gave (R)-benzyl 3-(1-(7-chloro-4-oxo-3-(phenylamino)-3,4-dihydroquinazolin-2-yl)but-3-ynylamino)propylcarbamate (>90%). M.p.=63-65° C.; 400 MHz $^1$H NMR (DMSO-d$_6$) δ: 9.09 (s, 1H), 8.07 (d, J=8.8, 1H), 7.83 (s, br, 1H), 7.59-7.56 (dd, J=2.0; 6.4, 1H), 7.29 (m, 5H), 7.18 (m, 2H), 6.83 (t, J=7.6, 1H), 6.67 (d, J=8.0, 2H), 4.95 (s, 2H), 4.20 (s, br, 1H), 4.00, s, br, 1H), 3.03-2.98 (dd, 2H), 2.75-2.5 (m, 3H), 2.3 (m, br 2H), 1.46 (m, 2H); LCMS: 530 [M+H].

Example 79

(R)-Benzyl 3-(3-chloro-N-(1-(7-chloro-4-oxo-3-(phenylamino)-3,4-dihydroquinazolin-2-yl)but-3-ynyl-2-fluorobenzamido)propyl Carbamate

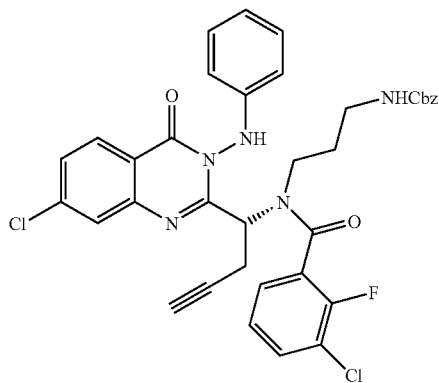

(R)-Benzyl 3-(1-(7-chloro-4-oxo-3-(phenylamino)-3,4-dihydroquinazolin-2-yl)but-3-ynylamino)propylcarbamate (0.28 g, 0.53 mmol) was dissolved in dichloromethane (5 mL). Triethylamine (0.22 mL, 1.60 mmol) was added followed by the addition of 2-fluoro-3-chlorobenzoyl chloride (0.112 g, 0.58 mmol). The reaction was stirred under a nitrogen atmosphere until the reaction was complete (LC/MS) (total of 5 min). The mixture was stirred for an additional 10 min, diluted with dichloromethane (50 mL) and washed with aqueous sodium bicarbonate (5 mL), water (5 ml×2) and brine solution and dried over anhydrous sodium sulfate. The solid was removed by filtration and the solvent removed under vacuum to provide (R)-benzyl 3-(3-chloro-N-(1-(7-chloro-4-oxo-3-(phenylamino)-3,4-dihydroquinazolin-2-yl)but-3-ynyl)-2-fluorobenzamido)propyl-carbamate as an orange solid (0.31 g, 0.45 mmol, 84%). mp 103-105° C. $^1$H-NMR (DMSO-d$_6$): δ 9.41-8.94 (m, 1H), 8.21-5.62 (m, 16H), 5.35-4.80 (m, 2H), 3.46-1.15 (m, 11H). LC/MS: 686 [M+H].

Example 80

(R)-N-(3-Aminopropyl)-3-chloro-N-(1-(7-chloro-4-oxo-3-(phenylamino)-3,4-dihydroquinazolin-2-yl)but-3-ynyl)-2-fluorobenzamide (1)

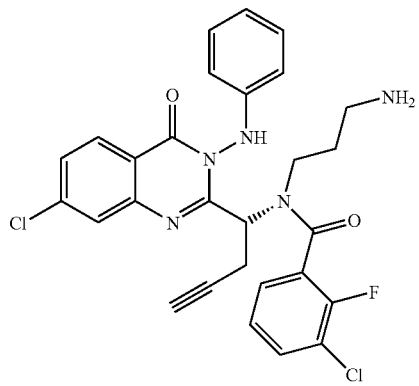

(R)-Benzyl 3-(3-chloro-N-(1-(7-chloro-4-oxo-3-(phenylamino)-3,4-dihydroquinazolin-2-yl)but-3-ynyl)-2-fluorobenzamido) propyl carbamate (0.62 g, 0.90 mmol), 1-ethynylcyclohexene (0.478 mL, 4.50 mmol) in ACN (20 mL) was added iodo-trimethylsilane (1.3 mL, 9.0 mmol). The reaction mixture was stirred at room temperature for 3 h. The resulting mixture was quenched with 10% aq Na$_2$CO$_3$ (40 mL). The layers were separated and the aqueous layer was washed with DCM (2×30 mL). The combined organic layers were washed with brine (1×40 mL), dried over MgSO$_4$, filtered and concentrated to yield an orange solid (1.2 g). The residue was separated on silica gel column (25%-50% EtOAc/Hex) to provide (R)-N-(3-aminopropyl)-3-chloro-N-(1-(7-chloro-4-oxo-3-(phenylamino)-3,4-dihydroquinazolin-2-yl)but-3-ynyl)-2-fluorobenzamide (0.24 g, 48%); mp 175° C. $^1$H-NMR (DMSO-d$_6$): δ 9.39-8.94 (m, 1H), 8.18-5.90 (m, 11H), 5.00-4.74 (m, 1H), 4.00-0.85 (m, 11H). LC/MS: 552 [M+H].

Example 81

N-(3-Amino-propyl)-N-[(R)-1-(7-chloro-4-oxo-3-phenylamino-3,4-dihydroquinazolin-2-yl-but-3-ynyl]-2,3,5,6-tetrafluoro-benzamide (71)

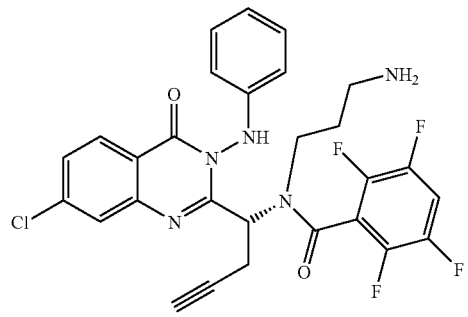

This compound was synthesized as described in general procedure D, except 1,2,4,5 tetrafluoro benzoyl chloride was used instead of 2-fluoro-3-chloro benzoyl chloride. M.p. 156-158° C. LCMS: m/e 572 [M+H]. $^1$H NMR (CDCl$_3$): δ 9.21-9.04 (m, 1H), 8.18-7.52 (m, 4H), 7.31-7.05 (m, 2H), 6.97-6.63 (m, 2H), 6.58-6.22 (m, 1H), 5.02-4.83 (m, 1H), 4.05-3.88 (m, 1H), 3.81-2.84 (m, 4H), 2.93-2.60 (m, 1H), 2.56-1.37 (m, 5H).

Example 82

(R)-N-(3-Aminopropyl)-N-(1-(7-chloro-4-oxo-3-(phenylamino)-3,4-dihydroquinazolin-2-yl)but-3-ynyl)-2,3,4,5-tetrafluorobenzamide (72)

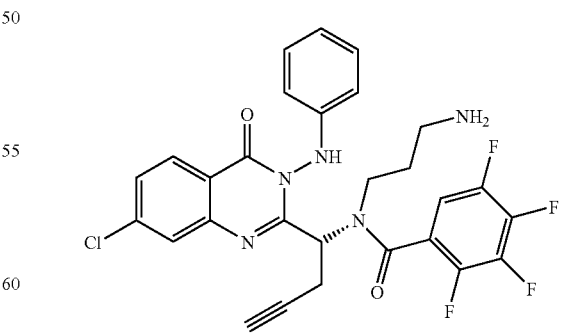

This compound was synthesized as described in general procedure D, except 2,3,4,5 tetrafluoro benzoyl chloride was used instead of 2-fluoro-3-chloro benzoyl chloride, M.p.=155-158° C.; 400 MHz $^1$H NMR (DMSO-d$_6$) δ: 9.4-4.8 (m, 12H), 4.0-0.8 (m, 10H); LCMS: 572 [M+H].

Example 83

(R)-N-(3-Aminopropyl)-N-(1-(7-chloro-4-oxo-3-(phenylamino)-3,4-dihydroquinazolin-2-yl)but-3-ynyl)benzo[b]thiophene-2-carboxamide (73)

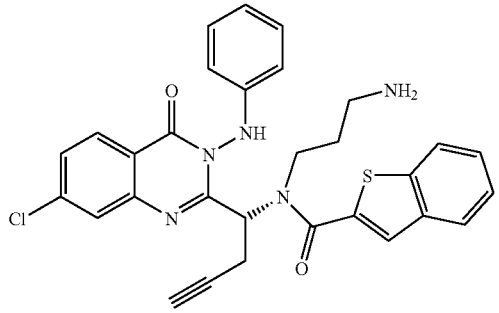

This compound was synthesized as described in general procedure D, except benzo[b]thiophene-2-carbonyl chloride was used instead of 2-fluoro-3-chloro benzoyl chloride, M.p.=103-106° C.; 400 MHz $^1$H NMR (DMSO-d$_6$) δ: 9.3-5.7 (m, 16H), 4.1-0.7 (m, 10H); LCMS: 556 [M+H].

Example 84

N-(3-Aminopropyl)-3-chloro-N-(1-(7-chloro-4-oxo-3-(phenylamino)-3,4-dihydroquinazolin-2-yl)pent-3-ynyl)-2-fluorobenzamide (74)

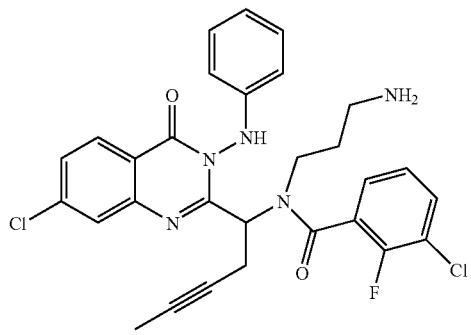

This compound was synthesized as described in general procedure D, except (DL)-2-tert-butoxycarbonylamino-hex-4-ynoic acid was used instead of (R)-2-tert-butoxycarbonylamino-pent-4-ynoic acid M.p.=185-190° C.; $^1$H NMR 400 MHz (DMSO-d$_6$) δ: 9.4-4.9 (m, 14H), 4.1-1.0 (m, 12H); LCMS: 566 [M+H].

Example 85

N-(3-Amino-propyl)-N-[(R)-1-(7-chloro-4-oxo-3-phenylamino-3,4-dihydro-quinazolin-2-yl)-but-3-ynyl]-4-methyl-benzamide (75)

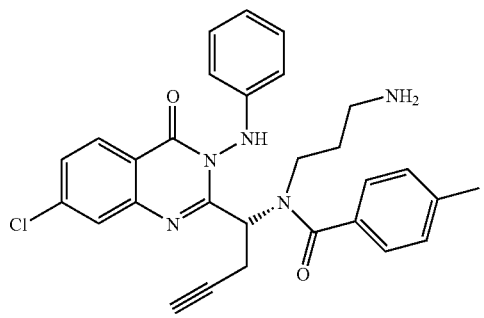

This compound was synthesized as described in general procedure D, except 4-methyl benzoyl chloride was used instead of 2-fluoro-3-chloro benzoyl chloride. M.p.=130-133° C. (Dec.); 400 MHz $^1$H NMR (DMSO-d$_6$) δ: 9.2-6.3 (m, 15H), 4.0-0.8 (m, 13H); LCMS: 514 [M+H].

Example 86

N-(3-Amino-propyl)-N-[(R)-1-(7-chloro-4-oxo-3-phenylamino-3,4-dihydro-quinazolin-2-yl)-but-3-ynyl]-2,3-difluoro-4-methyl-benzamide (76)

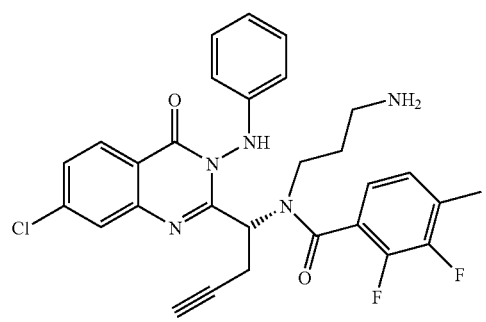

This compound was synthesized as described in general procedure D, except 2,3-difluoro-4-methyl benzoyl chloride was used instead of 2-fluoro-3-chloro benzoyl chloride. M.p.=175-180° C.; 400 MHz $^1$H NMR (DMSO-d$_6$) δ: 9.7-6.2 (m, 13H), 4.9-1.2 (m, 13H); LCMS: 550 [M+H].

Example 87

(R)-N-(3-Aminopropyl)-N-(1-(7-chloro-4-oxo-3-phenylamino-3,4-dihydroquinazolin-2-yl)but-3-ynyl)-2,3-difluoro-6-methoxybenzamide (77)

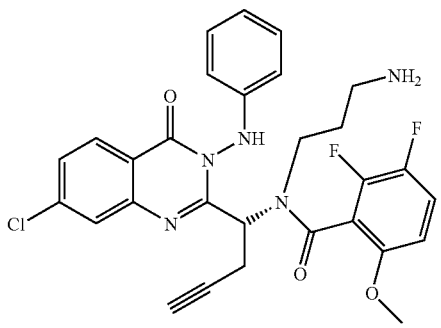

This compound was synthesized as described in general procedure D, except 2,3-di-fluoro-6-methoxy benzoyl chloride was used instead of 2-fluoro-3-chloro benzoyl chloride. M.p. 138-145° C. $^1$H NMR 400 MHz (DMSO): δ 9.17-8.9 (m, 1H), 8.07 (s, 1H), 7.94-7.68 (m, 1H), 7.65-7.50 (m, 4H), 7.19-7.04 (m, 3H), 6.87-6.79 (m, 2H), 6.69-6.51 (m, 3H), 6.24-6.18 (m, 1H), 4.89 (d, J=10.56 Hz 1H), 3.87-3.74 (m, 2H), 3.64-3.36 (m, 2H), 3.19-2.88 (m, 2H), 2.69-2.53 (m, 2H), 1.65-1.55 (m, 1H). LCMS: m/e 566 [M+H].

Example 88

(R)-N-(3-Aminopropyl)-N-(1-(7-chloro-4-oxo-3-phenylamino)-3,4-dihydroquinazolin-2-yl)but-3-ynyl)-2,3-difluoro-4-methoxybenzamide (78)

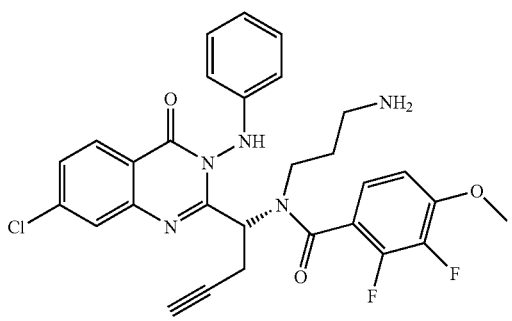

This compound was synthesized as described in general procedure D, except 2,3-di-fluoro-4-methoxy benzoyl chloride was used instead of 2-fluoro-3-chloro benzoyl chloride. M.p. 135-140° C. $^1$H NMR (DMSO): δ 9.12-9.00 (m, 1H), 8.14-6.48 (m, 13H), 5.28 (br, 1H), 3.91-3.86 (m, 1H), 3.81-3.73 (m, 2H), 3.46-3.30 (m, 2H), 3.28-3.06 (m, 1H), 2.96-2.89 (m, 1H), 2.73-2.65 (m, 1H), 2.45-2.56 (m, 1H), 2.31-2.13 (m, 1H), 2.06 (s, 1H). LCMS: m/e 566.17 [M+H].

Example 89

(R)-N-(3-Aminopropyl)-4-chloro-N-(1-(7-chloro-4-oxo-3-phenylamino)-3,4-dihydroquinazolin-2-yl)but-3-ynyl)-2,6-difluoro-benzamide (79)

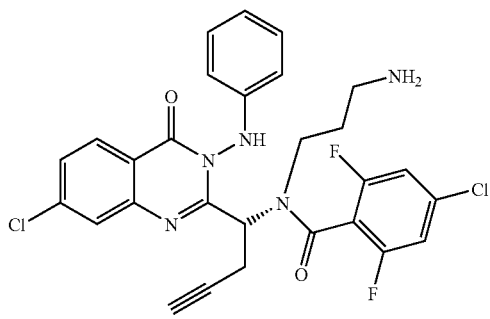

This compound was synthesized as described in general procedure D, except 2,6-di-fluoro-4-chloro benzoyl chloride was used instead of 2-fluoro-3-chloro benzoyl chloride. M.p. 140-145° C. $^1$H NMR (DMSO): δ 9.09-9.05 (m, 1H), 8.11-07 (m, 1H), 7.92-7.89 (m, 1H), 7.85-7.73 (m, 1H), 7.68-7.52 (m, 4H), 7.35-7.17 (m, 2H), 7.15-7.04 (m, 3H), 6.86-6.81 (m, 2H), 6.56-6.54 (d, J=8.22 Hz, 1H), 6.28-6.26 (d, J=8.22 Hz, 1H), 4.98-4.96 (m, 1H), 3.94-3.62 (m, 2H), 3.16-2.93 (m, 4H), 2.77-2.65 (m, 2H). LCMS: m/e 571 [M+H].

Example 90

(R)-N-(3-Aminopropyl)-N-(1-(7-chloro-4-oxo-3-(phenylamino)-3,4-dihydroquinazolin-2-yl)but-3-ynyl)-3,5-difluorobenzamide (80)

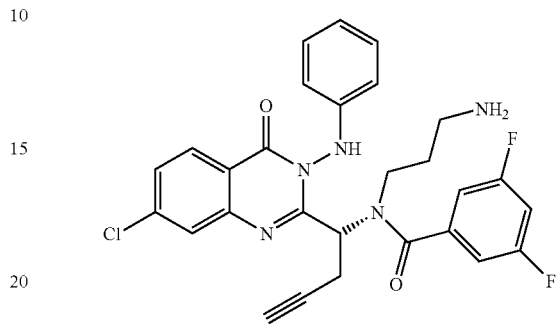

This compound was synthesized as described in general procedure D, except 3,5-di-fluoro benzoyl chloride was used instead of 2-fluoro-3-chloro benzoyl chloride, M.p. 165-167° C. LCMS: m/e 536 [M+H]. 1H NMR (DMSO-d6): δ 9.18 (s, 1H), 8.12 (m, 1H), 7.95 (s, 1H), 7.65 (m, 3H), 7.38 (d, J=8.0 Hz, 2H), 7.04 (m, 2H), 6.79 (m, 1H), 6.46 (d, J=7.6 Hz, 1H), 4.97 (m, 1H), 3.18 (m, 2H), 3.01 (m, 2H), 2.73 (m, 2H), 1.91 (s, 1H), 1.73 (m, 2H), 1.33-1.19 (m, 2H).

Example 91

(R)-N-(3-Aminopropyl)-N-(1-(7-chloro-4-oxo-3-(phenylamino)-3,4-dihydroquinazolin-2-yl)but-3-ynyl)-2,3,5-trifluorobenzamide (81)

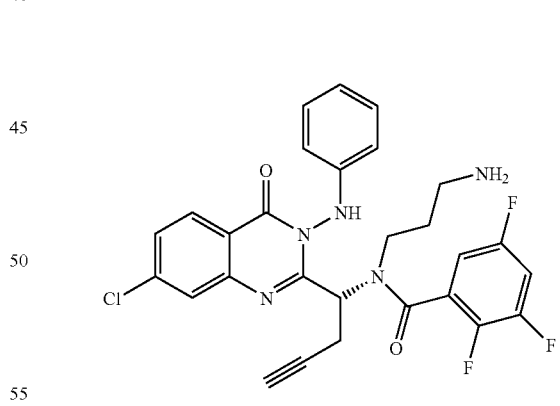

This compound was synthesized as described in general procedure D, except 2,3,5-tri-fluoro benzoyl chloride was used instead of 2-fluoro-3-chloro benzoyl chloride, m.p. 168-170° C. LCMS: m/e 554 [M+H]. $^1$H NMR (CDCl$_3$): δ 8.14 (s, 1H), 8.06 (t, J=6.8 Hz, 1H), 7.81 (m, 1H), 7.41 (m, 1H), 7.06 (m, 2H), 6.81-6.88 (m, 2H), 6.62-6.72 (m, 3H), 5.04 (t, J=13.2 Hz), 3.79 (m, 1H), 3.63-3.81 (m, 2H), 3.52 (m, 1H), 3.15 (q, J=7.2 Hz, 1H), 2.97 (br s, 2H), 2.63-2.69 (m, 1H), 2.06 (d, J=6.8 Hz, 1H), 1.95 (m, 1H), 1.44 (t, J=7.2 Hz, 1H), 1.26 (m, 1H).

Example 92

(R)-N-(3-Aminopropyl)-N-(1-(7-chloro-4-oxo-3-(phenylamino)-3,4-dihydroquinazolin-2-yl)but-3-ynyl)-2,3-difluorobenzamide (82)

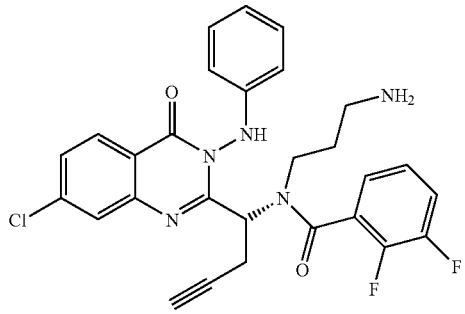

This compound was synthesized as described in general procedure D, except 2,3-di-fluoro benzoyl chloride was used instead of 2-fluoro-3-chloro benzoyl chloride, m.p. 168-170° C. LCMS: m/e 536 [M+H]. $^1$H NMR (CDCl$_3$): δ 8.14 (s, 1H), 8.06 (t, J=6.8 Hz, 1H), 7.81 (m, 1H), 7.41 (m, 1H), 7.06 (m, 2H), 6.81-6.88 (m, 2H), 6.62-6.72 (m, 3H), 5.04 (t, J=13.2 Hz, 1H), 3.79 (m, 1H), 3.63-3.81 (m, 2H), 3.52 (m, 1H), 3.15 (q, J=7.2 Hz, 1H), 2.97 (br s, 2H), 2.63-2.69 (m, 1H), 2.06 (d, J=6.8 Hz, 1H), 1.95 (m, 1H), 1.44 (t, J=7.2 Hz, 1H), 1.26 (m, 1H).

Example 93

General Procedure E; Synthesis of (R)-N-(3-aminopropyl)-3-chloro-2-fluoro-N-(1-(4-oxo-3-(phenylamino)-3,4-dihydropyrido[3,2-d]pyrmidin-2-yl)but-3-ynyl)benzamide (83)

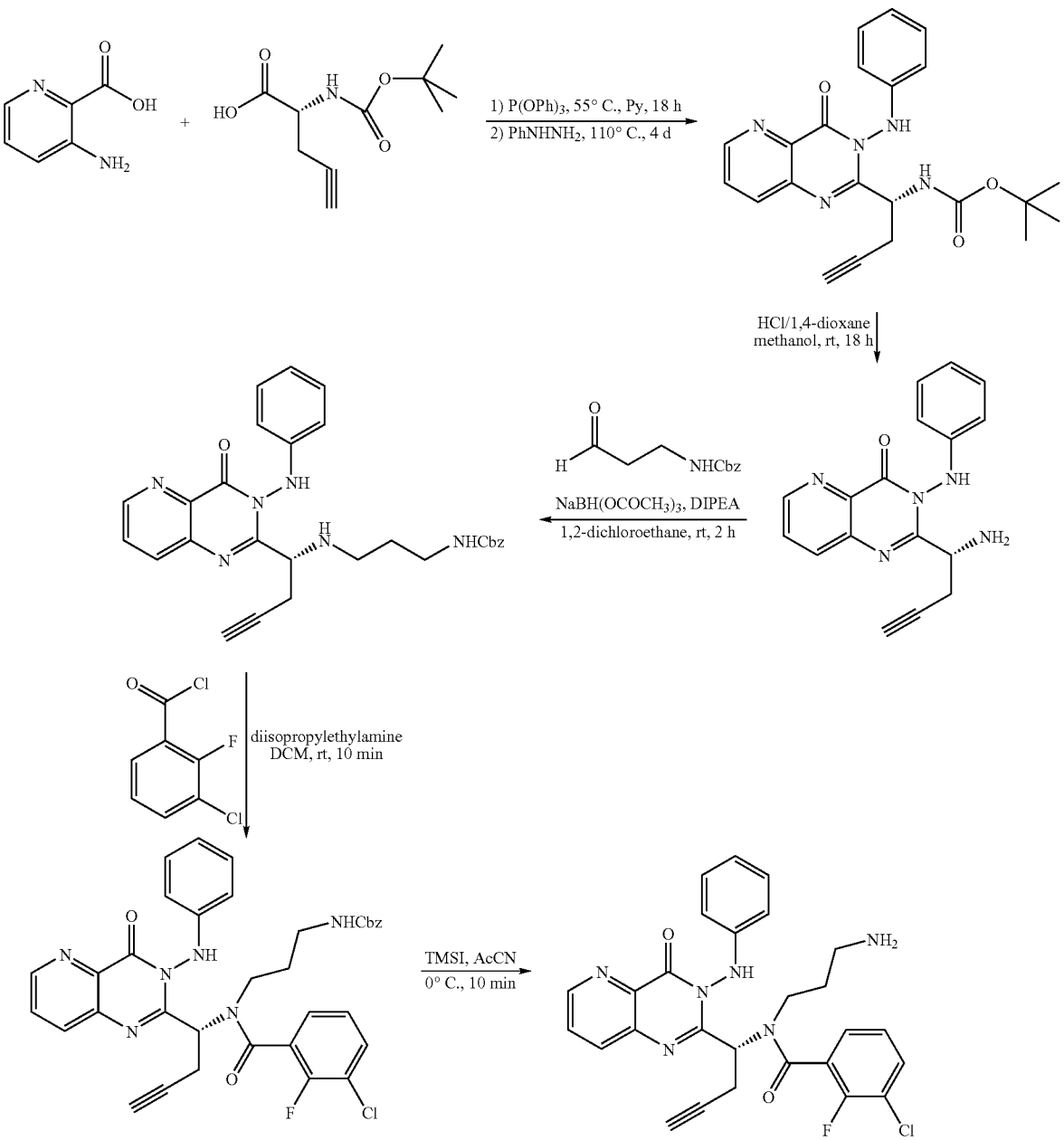

Example 94

(R)-tert-butyl 1-(4-oxo-3-(phenylamino)-3,4-dihydropyrido[3,2-d]pyrimidin-2-yl)but-3-ynylcarbamate

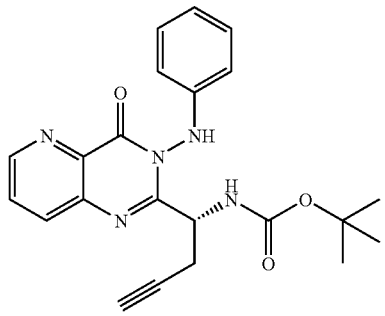

To a mixture of 3-aminopicolinic acid (1.94 g, 14.06 mmol) and D-boc-propargylglycine in pyridine (anhydrous, 50 ml) was added triphenylphosphite (4.43 ml, 16.87 mmol). The mixture was heated at 55° C. for 18 hours. After cooling to room temperature, phenyl hydrazine (1.66 ml, 16.87 mmol) was added. The resulted mixture was stirred at 110° C. for four days. The solvent was removed under reduced pressure. 250 ml of EtOAc and 80 ml of water were added to the residue. The organic layer was separated, then washed with brine (80 ml), dried over $Na_2SO_4$ and concentrated to dryness under reduced pressure. The crude produce was purified by flash silica gel chromatography eluting with hexanes/EtOAc (1:1) to afford (R)-tert-butyl 1-(4-oxo-3-(phenylamino)-3,4-dihydropyrido[3,2-d]pyrimidin-2-yl)but-3-ynylcarbamate (2.12 g, 37%) as a light brown solid, M.p. 108-110° C. LCMS: m/e 406 [M+H]. $^1$H NMR, 400 MHz ($CDCl_3$): δ 8.87 (d, J=4 Hz, 1H), 8.15 (d, J=8.0 Hz, 1H), 7.73 (m, 1H), 7.24 (m, 3H), 7.00 (t, J=8.0 Hz, 1H), 6.78 (s, 2H), 5.88 (m, 1H), 5.32 (s, 1H), 3.10-2.62 (m, 2H), 1.96 (s, 1H), 1.45 (s, 9H).

Example 95

(R)-2-(1-Aminobut-3-ynyl)-3-(phenylamino)pyrido[3,2-d]pyrimidin-4(3H)-one

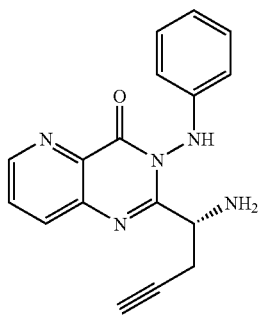

To a solution of (R)-tert-butyl 1-(4-oxo-3-(phenylamino)-3,4-dihydropyrido[3,2-d]pyrimidin-2-yl)but-3-ynylcarbamate (1.20 g, 2.96 mmol) in methanol (15 ml) was added 4.5 ml of HCl (4.0 M in 1,4-dioxane). The reaction was carried out at room temperature for 18 hours. The solvent was removed under reduced pressure to afford (R)-2-(1-aminobut-3-ynyl)-3-(phenylamino)pyrido[3,2-d]pyrimidin-4(3H)-one (1.1 g) as a light brown solid, M.p. 206-208° C. LCMS: m/e 306 [M+H]. 1H NMR (400 MHz) (DMSO-$d_6$): δ 9.34 (s, 1H), 8.85 (s, 1H), 8.20 (d, J=8 Hz, 1H), 7.94 (dd, J=8.0 Hz and 3.2 Hz, 1H), 7.22 (t, J=7.6 Hz, 2H), 6.91 (t, J=7.6 Hz, 1H), 6.80 (s, J=8 Hz, 1H), 4.98 (m, 3H), 4.53 (s, 1H), 3.11 (m, 2H).

Example 96

(R)-Benzyl 3-(1-(4-oxo-3-(phenylamino)-3,4-dihydropyrido[3,2-d]pyrimidin-2-yl)but-3-ynylamino)propylcarbamate

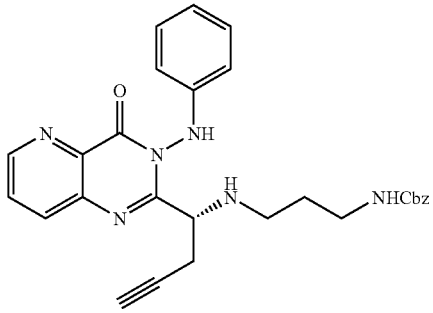

To a solution of (R)-2-(1-aminobut-3-ynyl)-3-(phenylamino)pyrido[3,2-d]pyrimidin-4(3H)-one (500 mg, 1.46 mmol) and diisopropylethylamine (638 μl, 3.66 mmol) in 1,2-dichloroethane (20 ml) was added 3-[(benzyloxycarbonyl)amino]propionaldehyde (303 mg, 1.46 mmol) and sodium triacetoxyborohydride (620 mg, 2.93 mmol). The reaction was stirred at room temperature for 2 hours before 10 ml of sodium carbonate was added. 200 ml of 1,2-dichloroethane and 40 ml of water were added to the reaction mixture. The organic layer was separated and washed with brine (50 ml), dried over $Na_2SO_4$ and concentrated to dryness under reduced pressure. The crude produce was purified by flash silica gel chromatography eluting with $CH_2Cl_2/CH_3OH$ (18:1) to afford (R)-benzyl 3-(1-(4-oxo-3-(phenylamino)-3,4-dihydropyrido[3,2-d]pyrimidin-2-yl)but-3-ynylamino)propyl carbamate (365 mg, 50%) as a off-white solid, M.p. 75-77° C. LCMS: m/e 497 [M+H]. 1H NMR ($CDCl_3$): δ8.85 (dd, J=6.4 Hz and 1.6 Hz, 1H), 8.12 (d, J=8 Hz, 1H), 7.65 (br, 1H), 7.31 (m, 5H), 7.23 (t, J=8.4 Hz, 3H), 6.99 (t, J=7.2 Hz, 1H), 6.72 (d, J=7.6 Hz, 2H), 5.61 (s, 1H), 5.07 (m, 2H), 4.29 (s, 1H), 3.37-3.22 (m, 2H), 2.74 (s, 2H), 2.52 (m, 2H), 1.03 (m, 4H).

Example 97

(R)-Benzyl 3-(3-chloro-2-fluoro-N-(1-(4-oxo-3-(phenylamino)-3,4-dihydropyrido[3,2-d]pyrimidin-2-yl)but-3-ynyl)benzamido)propylcarbamate

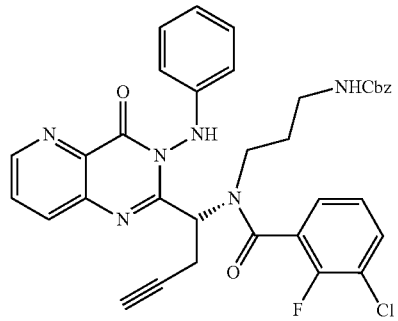

To a solution of (R)-benzyl 3-(1-(4-oxo-3-(phenylamino)-3,4-dihydropyrido[3,2-d]pyrimidin-2-yl)but-3-ynylamino)

propylcarbamate (130 mg, 0.262 mmol) and diisopropylethylamine (50 μl, 0.288 mmol) in dichloromethane (anhydrous, 2.0 ml) was added 3-chloro-2-fluorobenzoyl chloride (55 mg, 0.288 mmol). The reaction was carried out at room temperature for 10 minutes. 150 ml of dichloromethane was added to the reaction mixture, then washed with sat.NaHCO₃ solution (30 ml), water (30 ml), and brine (30 ml), dried over Na₂SO₄ and concentrated to dryness under reduced pressure. The crude produce was purified by flash silica gel chromatography eluting with hexanes/EtOAc (1:1) to afford (R)-benzyl 3-(3-chloro-2-fluoro-N-(1-(4-oxo-3-(phenylamino)-3,4-dihydropyrido[3,2-d]pyridin-2-yl)but-3-ynyl)benzamido)propylcarbamate (125 mg, 74%) as a pale yellow solid, M.p. 100-102° C. LCMS: m/e 653 [M+H]. 1H NMR (CDCl₃): δ 8.88 (d, J=2.8 Hz, 1H), 8.15 (d, J=8.8 Hz, 1H), 7.70 (m, 1H), 7.35 (m, 6H), 7.23 (m, 2H), 7.08 (t, J=7.2 Hz, 2H), 6.88 (s, 1H), 6.51 (s, 2H), 5.25 (s, 1H), 5.13-4.99 (m, 2H), 3.77 (m, 1H), 3.51 (m, 1H), 3.30-3.14 (m, 2H), 2.05 (m, 1H), 1.64 (s, 1H), 1.45 (m, 2H), 1.26 (m, 2H).

Example 98

(R)-N-(3-Aminopropyl)-3-chloro-2-fluoro-N-(1-(4-oxo-3-(phenylamino)-3,4-dihydropyrido[3,2-d]pyrimidin-2-yl)but-3-ynyl)benzamide (83)

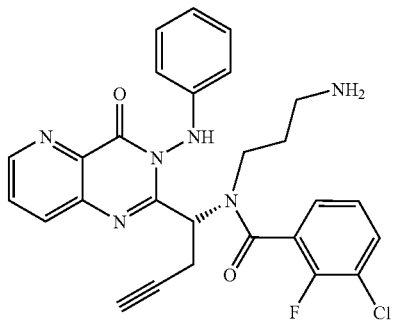

To a solution of (R)-benzyl 3-(3-chloro-2-fluoro-N-(1-(4-oxo-3-(phenylamino)-3,4-dihydropyrido[3,2-d]pyrimidin-2-yl)but-3-ynyl)benzamido)propylcarbamate (100 mg, 0.153 mmol) in acetonitrile (2 ml) was slowly added iodotrimethylsilane (83 μl, 0.613 mmol) at 0° C. After stirring for 10 minutes, 0.5 ml of sat.NaHCO₃ solution was added to quench the reaction. 100 ml of dichloromethane was added to the reaction mixture, then washed with water (30 ml), brine (30 ml), dried over Na₂SO₄ and concentrated to dryness under reduced pressure. The crude product was purified by preparative HPLC. The resulted product (TFA salt) was dissolved in dichloromethane (100 ml) and washed with sat.NaHCO₃ solution (20 ml), sat.NaCl solution (20 ml), dried over Na₂SO₄ and concentrated to dryness under reduced pressure. To a solution of the residue in EtOAc (2 ml) was added HCl:EtOAc (3.0 M, 1.0 ml). The mixture was stirred at room temperature for 30 minutes and concentrated to afford (R)-N-(3-aminopropyl)-3-chloro-2-fluoro-N-(1-(4-oxo-3-(phenylamino)-3,4 dihydropyrido[3,2-d]pyrimidin-2-yl)but-3-ynyl)benzamide (40 mg, 44%, 2HCl) as a pale yellow solid, M.p. 198-200° C. LCMS: m/e 519 [M+H]. ¹H NMR (CD₃OD): δ 8.93 (s. 1H), 8.59 (d, J=8.0 Hz, 1H), 8.12 (s, 1H), 7.52 (s, 1H), 7.27 (d, J=6.4 Hz, 2H), 7.10 (s, 2H), 7.00 (m, 1H), 6.85 (s, 1H), 6.53 (s, 1H), 6.38 (s, 1H), 5.51 (s, 1H), 5.26 (s, 1H), 3.73-3.59 (m, 2H), 2.65-2.29 (m, 2H), 2.01-1.59 (m, 2H), 1.19 (m, 4H).

Example 99

(R)-N-(3-Aminopropyl)-2,3-difluoro-4-methyl-N-(1-(4-oxo-3-(phenylamino)-3,4-dihydropyrido[3,2-d]pyrimidin-2-yl)but-3-ynyl)benzamide (84)

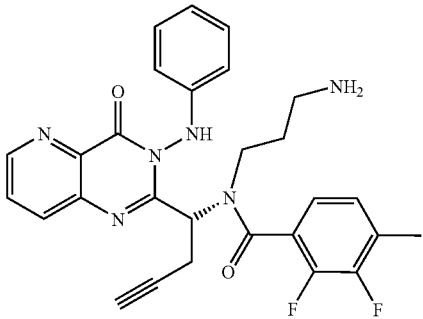

This compound was synthesized as described in general procedure E, except 2,3-di-fluoro-4-methy benzoyl chloride was used instead of 2-fluoro-3-chloro benzoyl chloride as a yellow solid, M.p. 185-187° C. LCMS: m/e 517 [M+H]. ¹H NMR (DMSO-d₆): δ 9.18 (m. 1H), 8.87 (m, 1H), 8.31 (m, 1H), 7.95 (m, 1H), 7.78 (s, 1H), 7.21 (m, 1H), 7.08 (m, 1H), 6.84 (m, 2H), 6.52 (d, J=8.0 Hz, 1H), 6.33 (m, 1H), 5.23 (s, 1H), 4.99 (m, 1H), 4.18 (s, 2H), 3.47 (m, 1H), 3.24 (m, 1H), 2.91 (m, 1H), 2.72 (m, 1H), 2.33 (m, 2H), 2.05 (s, 3H), 1.67 (m, 2H).

Example 100

(R)-N-(3-Aminopropyl)-2,6-difluoro-3-methyl-N-(1-(4-oxo-3-(phenylamino)-3,4-dihydropyrido[3,2-d]pyrimidin-2-yl)but-3-ynyl)benzamide (85)

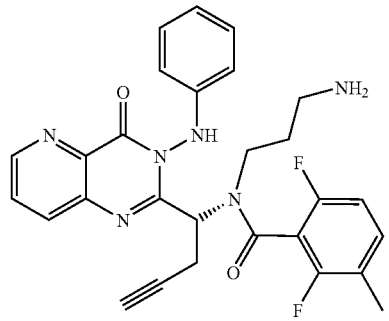

This compound was synthesized as described in general procedure E, except 2,6-di-fluoro-3-methy benzoyl chloride was used instead of 2-fluoro-3-chloro benzoyl chloride as a yellow solid, M.p. 198-200° C. LCMS: m/e 517 [M+H]. 1H NMR (DMSO-d₆): δ 9.14 (m. 1H), 8.88 (m, 1H), 8.31 (m, 1H), 7.96 (m, 1H), 7.81 (s, 1H), 7.12 (m, 2H), 6.85 (m, 2H), 6.60 (d, J=7.6 Hz, 1H), 6.28 (m, 1H), 5.99 (m, 1H), 5.08 (m, 1H), 3.76 (s, 2H), 3.38-3.21 (m, 2H), 3.18 (m, 1H), 2.92 (m, 1H), 2.26 (s, 2H), 2.12 (s, 1H), 2.03 (s, 1H), 1.98 (s, 1H), 1.24 (s, 2H).

Example 101

(R)-N-(3-Aminopropyl)-2,3,4,5-tetrafluoro-N-(1-(4-oxo-3-(phenylamino)-3,4-dihydropyrido[3,2-d]pyrimidin-2-yl)but-3-ynyl)benzamide (86)

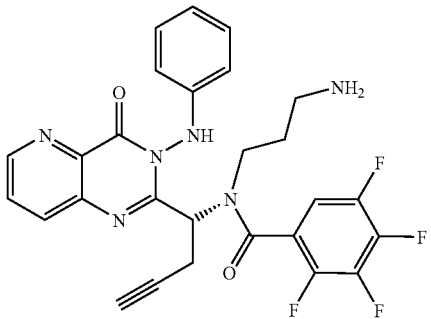

This compound was synthesized as described in general procedure E, except 2,3,4,5-tetra-fluoro benzoyl chloride was used instead of 2-fluoro-3-chloro benzoyl chloride as a pale yellow solid, M.p. 180-182° C. LCMS: m/e 539 [M+H]. 1H NMR (DMSO-$d_6$): δ 9.24 (m. 1H), 8.89 (m, 1H), 8.31 (m, 1H), 7.96-7.71 (m, 3H), 7.20 (m, 1H), 7.13 (m, 1H), 6.94-6.67 (m, 1H), 6.58 (d, J=8.0 Hz, 1H), 5.40 (br, 3H), 3.50 (m, 1H), 3.45 (m, 1H), 3.29 (m, 2H), 3.20 (m, 1H), 2.71 (m, 1H), 1.82-1.54 (m, 2H), 1.30-1.20 (m, 2H).

Example 102

Fluorescence Detection of HsEg5 ATPase Activity and Compound Inhibition

Purified HsEg5 motor fragment was activated by mixture with preformed MT polymer (Cytoskeleton, Denver, Colo.) at room temperature for 20 minutes. MT activated ATPase activity was measured using ADP Quest (DiscoverX, Fremont, Calif.) in which a coupled-enzyme assay can translate accumulation of ADP into detectable resorufin signal (FIG. 1A). Fluorescence was measured at $λ_{Ex}$=535 nm and $λ_{Em}$=590 nm on a Wallac Victor 2 plate reader (Perkin-Elmer Life Sciences, Boston, Mass.). Reagent A and B from ADP Quest kit were aliquoted and frozen in 20° C. before use. A standard curve was determined using the provided ADP reagent in the reaction buffer that consisted of 50 mM Pipes (pH7.0), 5.0 mM $MgCl_2$, 20 μM paclitaxel and 0.5 μM tubulin. The same buffer was used for $K_m$ determination with HsEg5 concentration of 10 nM.

For inhibitor screening, 4 μL of compounds were incubated with 10 μL of MT-activated HsEg5 such that the final concentrations for compound range from 100 μM to 5 nM (1 to 3 serial dilutions, final concentration) and final concentration for HsEg5 is 10 nM. The mixture was incubated at room temperature for 10 minutes with mild shaking. The screening assay contained 0.3% DMSO in all reaction wells. We used wells containing only DMSO as negative controls and wells without ATP as background. Addition of 6 μL ATP (final concentration of 20 μM) initiated the ATP hydrolysis reaction. The 20 μL-reaction was allowed to proceed at room temperature for 10 minutes before addition of 10 μL of reagent A and 20 μL of reagent B. After 20-minute development at room temperature, the fluorescence was measured and data analysis was performed using GraphPad Prism version 3.0 (GraphPad Software, San Diego, Calif.)

Example 103

Robotic Settings for High-Throughput Screening

For the purpose of high-throughput screening, we automated the fluorescence assay using a Sciclone ALH3000 (Caliper Life Sciences, Hopkinton, Mass.) and Multidrop 384 (Thermo Electron Corp, Waltham, Mass.). First, compound dilution plates for screening (at 10 μM or 1 μM) and $IC_{50}$ determination (10 data points from 100 μM to 5 nM) were made in Corning polypropylene V-bottom 96-well plates. In both cases, the 1st and $7^{th}$ column contained background (No ATP addition) and negative control (DMSO only). For screening compounds at 10 μM or 1 μM, 4 μl of each compound at 50 μM or 5 μM were used in a 20 μL assay reaction. For $IC_{50}$ determination, the mother compound plate contained 24 μL of tested compound at stock concentration of 30 mM. 6 μL of each test compound in 30 mM was added to each well in the column 2 and followed by 1:3 serial dilutions in DMSO with the Sciclone ALH3000. 234 μL of assay buffer was then added using a Multidrop 384. Then 4 μL of diluted compounds was used in 20 μL-reaction. The final concentration was a 1:300 dilution of the original stock. Second, a reagent source plate was prepared with three rows designated to MT-activated HsEg5, Reagent A and Reagent B respectively. MTs were diluted with assay buffer and polymerized at room temperature for 10 minutes. Just before use, HsEg5 protein was thawed on ice and activated by addition of MT polymers at room temperature for 20 minutes. HsEg5/MT was then added to Row A of the reagent source plate. The final assay concentration was 10 nM HsEg5 and 500 nM MTs. Reagent A and B were stored at −20° C. and thawed at room temperature followed by transferring to rows B & C of the reagent source plate. Third, ATP substrate plate was prepared by transferring 80 μM ATP solution to each well of a V-shape 96-well plate except the wells in the first row where assay buffer was added instead to have no-ATP blanks. The final concentration for ATP in the assay was 20 μM.

The assay was programmed on Sciclone ALH3000 with the following procedures: 1) Addition of 4 μL compounds to the assay plate, followed by addition of 10 μL of MT-activated HsEg5. The mixture was incubated at room temperature for 10 minutes with occasionally shaking; 2) HsEg5 ATPase reaction was initiated by addition of 6 μL of ATP and proceeded at room temperature for 10 minutes. 3) Addition of 10 μL reagent A and 20 μL reagent B to the plate and incubation at room temperature for exactly 20 minutes. The fluorescence was measured at Wallac Victor 2 multilabel counter with excitation and emission wavelength stated previously.

Example 104

Luminescent Detection of HsEg5 ATPase Activity and Compound Inhibition

Purified HsEg5 motor fragment was activated by mixture with preformed MT polymer (Cytoskeleton, Denver, Colo.) at room temperature for 20 minutes. MT activated ATPase activity was measured using Kinase-Glo® Plus Luminescent Kinase Assay (Promega, Madison, Wis.).

For inhibitor screening, 5 μL of compounds were incubated with 20 μL of MT-activated HsEg5 such that the final concentrations for compound range from 100 μM to 5 nM (1 to 3 serial dilutions, final concentration) and final concentration for HsEg5 is 25 nM. The mixture was incubated at room temperature for 20 minutes with mild shaking. The screening assay contained 0.3% DMSO in all reaction wells. We used wells containing only DMSO as negative controls and wells without ATP as background. Addition of 15 μL of 13 μM ATP (final concentration of 5 μM) initiated the ATP hydrolysis reaction. The 40 μL-reaction was allowed to proceed at room temperature for 45 minutes before addition of 40 μL of Kinase®-Glo Plus. After 15-minute development at room temperature, the luminescent was measured.

Example 105

MTS Assay

Cell viability was determined by measuring the activity of dehydrogenase enzymes in metabolically active cells using a tetrazolium compound, MTS. The assay was performed as described in Promega Technical Bulletin No. 169 (CellTiter 96 Aqueous Non-Radioactive Cell Proliferation Assay). Two human cancer cell lines were assayed (see, Table 1). Cells were maintained at 37° C. and 5% $CO_2$ in DMEM media (4.5 g/L glucose) supplemented with 10% heat-inactivated FBS, 10 mM L-glutamine, and 10 mM Hepes pH 7.5. Briefly, cells were seeded in 96-well plates as set forth in Table 1 and incubated for 16-24 hours. Candidate compounds were serially diluted in DMSO, further diluted in cell culture media, and then added to cells (final DMSO concentration of 0.33%). Cells were incubated in the presence of candidate compound for 72 hours. MTS stock solution (MTS 2 gm/L, PMS 46.6 mg/ml in PBS) was added to the cells (final concentration MTS 2 gm/L and PMS 7.67 mg/L) and incubated for 4 hours. SDS was added to a final concentration of 1.4% and absorbance at 490 nM was measured within two hours using a plate reader. The $IC_{50}$ was defined as the concentration of compound that results in a 50% reduction in the number of viable cells as compared to control wells treated with DMSO only (0.33%) and was calculated using non-linear regression analysis. $IC_{50}$ values were given in Table 2 for the compounds listed. The Compound Numbers in Table 2 correspond to the numbers listed parenthetically in the Example titles.

TABLE 1

| Cell Line | Cancer Type | Cells/well |
|---|---|---|
| A549 | non small cell lung | 400 |
| NCI-H460 | non small cell lung | 180 |

TABLE 2

| Compound Number | Molecular weight | Eg5 $IC_{50}$* (μM) | MTS NCI H460 $IC_{50}$ (μM) | MTS NCI A549 $IC_{50}$ (μM) |
|---|---|---|---|---|
| 1 | 552.43 | 0.028 | 0.36 | 0.42 |
| 2 | 568.90 | 0.645 | 1.75 | 2.37 |
| 3 | 504.03 | 0.702 | 1.19 | 2.3 |
| 4 | 524.45 | 0.72 | 1.14 | 2.4 |
| 5 | 535.00 | 1.05 | 2.39 | 4.4 |
| 6 | 558.89 | 0.418 | 1.16 | 1.87 |
| 7 | 525.98 | 0.566 | 1.77 | 2.57 |
| 8 | 507.99 | 2.13 | 2.83 | 4.75 |
| 9 | 525.98 | 1.16 | 2.39 | 3.57 |
| 10 | 543.97 | 0.599 | 1.14 | 2.36 |
| 11 | 558.89 | 0.735 | 2.44 | 3.01 |
| 12 | 558.89 | 0.818 | 2.11 | 3.37 |
| 13 | 542.44 | 0.749 | 2.21 | 3.57 |
| 14 | 568.90 | 1.0 | 3.25 | 3.44 |
| 15 | 615.90 | 1.65 | 2.27 | 3.08 |
| 16 | 522.02 | 1.15 | 0.929 | 1.36 |
| 17 | 540.01 | 1.6 | 1.59 | 2.56 |
| 18 | 522.02 | 1.25 | 2.5 | 3.92 |
| 19 | 542.44 | 0.582 | 0.894 | 1.57 |
| 20 | 560.43 | 0.844 | 1.0 | 1.8 |
| 21 | 540.01 | 1.25 | 1.08 | 1.93 |
| 22 | 541.05 | 1.61 | 1.17 | 2.08 |
| 23 | 556.07 | 1.02 | 1.12 | 2.49 |
| 24 | 522.02 | 1.05 | 1.09 | 1.79 |
| 25 | 522.02 | 1.43 | 0.959 | 1.52 |
| 26 | 540.01 | 0.944 | 0.889 | 1.25 |
| 27 | 504.03 | 1.28 | 1.08 | 2.22 |
| 28 | 483.61 | 1.59 | 1.35 | 2.5 |
| 29 | 505.02 | 2.17 | 2.09 | 3.31 |
| 30 | 550.05 | NA | 12.0 | 7.1 |
| 31 | 544.05 | 1.43 | NA | 10.8 |
| 32 | 519.04 | 1.39 | 0.956 | 1.87 |
| 33 | 558.10 | 4.22 | 10.4 | NA |
| 34 | 532.09 | 1.65 | 5.47 | 6.36 |
| 35 | 554.04 | 1.96 | 6.15 | 4.52 |
| 36 | 586.95 | 1.86 | 3.77 | 4.37 |
| 37 | 570.49 | 1.66 | 4.49 | 5.02 |
| 38 | 588.53 | 4.59 | 3.59 | NA |
| 39 | 586.10 | 3.01 | 4.49 | 6.09 |
| 40 | 602.16 | 2.83 | 8.35 | 6.12 |
| 41 | 544.87 | 3.37 | 6.28 | 5.67 |
| 42 | 540.01 | 0.476 | 2.08 | 4.28 |
| 43 | 522.02 | 0.833 | 2.81 | 3.49 |
| 44 | 582.93 | 1.85 | 13.4 | 13.8 |
| 45 | 574.46 | 0.743 | 3.17 | 3.24 |
| 46 | 536.05 | 0.246 | 0.678 | NA |
| 47 | 555.08 | 3.23 | 2.7 | 4.09 |
| 48 | 637.00 | 2.57 | 4.36 | 4.93 |
| 49 | 572.13 | 3.44 | 4.41 | 4.69 |
| 50 | 594.08 | 1.18 | 3.12 | 3.77 |
| 51 | 576.09 | 2.8 | 5.38 | 4.45 |
| 52 | 594.08 | 1.25 | 3.47 | 4.29 |
| 53 | 610.54 | 2.62 | 4.44 | 5.26 |
| 54 | 636.96 | 2.41 | 11.9 | 12.2 |
| 55 | 622.04 | 4.16 | 16.1 | 33.7 |
| 56 | 570.42 | 0.138 | 1.86 | 3.82 |
| 57 | 552.43 | 0.0506 | 0.766 | 0.433 |
| 58 | 610.98 | 3.69 | 5.55 | 5.88 |
| 59 | 532.08 | 52.3 | 4.24 | NA |
| 60 | 510.42 | 3.99 | 10 | NA |
| 61 | 490.00 | 3.89 | 12.5 | 14.2 |
| 62 | 525.98 | 3.74 | 22.8 | 21.7 |
| 63 | 507.99 | 3.34 | 10.5 | 7.02 |
| 64 | 528.41 | 1.46 | 6.81 | 12.6 |
| 65 | 525.98 | 4.08 | 11.4 | 12.4 |
| 66 | 500.05 | NA | 3.20 | 2.35 |
| 67 | 490.05 | 8.3 | 13.1 | 15.5 |
| 68 | 490.05 | NA | 2.59 | 3.86 |
| 69 | 508.04 | NA | 3.77 | 3.9 |
| 70 | 476.02 | NA | 4.23 | 6.91 |
| 71 | 571 | 0.16 | 0.32 | 0.84 |
| 72 | 571 | 0.04 | 0.33 | 0.62 |
| 73 | 555 | 0.12 | 0.33 | 0.49 |
| 74 | 565 | 5.90 | 1.23 | 1.80 |
| 75 | 513 | 0.09 | 1.50 | 2.80 |
| 76 | 549 | 0.13 | 0.86 | 1.30 |
| 77 | 565 | 0.07 | 0.53 | 0.86 |
| 78 | 565 | 0.04 | 0.70 | 1.45 |
| 79 | 570 | 0.55 | 0.43 | 1.30 |
| 80 | 535 | 0.09 | 0.10 | 0.58 |
| 81 | 553 | 0.16 | 0.34 | 0.66 |
| 82 | 535 | 0.03 | NA | NA |
| 83 | 517 | 6.60 | 27.0 | >100 |

Eg5 $IC_{50}$ data was generated using both fluorescence and Luminescence detection assays as described above. Compounds 1-69 were screened using automated fluorescence assay while compounds 70-83 were screened using Luminescence detection assay. (See reference "Zhang B, Senator D, Wilson C J, Ng S C. (2005) "Development of a high-throughput robotic fluorescence-based assay for HsEg5 inhibitor screening" Anal Biochem. 345:326-335").

Example 106

In Vivo Data

Six-week old female athymic nude mice (NCR nu/nu; Charles River Laboratory, Wilmington, Mass.) were acclimated to the animal housing facility for at least 1 week before the study. Efficacy studies were performed in athymic mice bearing PACA2 tumor xenografts to determine the effect of compound on tumor growth. Tumor cells ($1 \times 10^7$ PACA2 cells/animal) were inoculated subcutaneously on day 0. Tumor dimensions were measured by a digital microcaliper, and tumor volumes were calculated as length×width$^2$/2. When tumors reached a volume of ~100 mm$^3$, mice were randomized into groups and treated 3× weekly (Monday-Wednesday-Friday, followed by a 2-day dosing holiday) intraperitoneally with either vehicle control or 6.25 and 12.5 mg/kg compound formulated in PEG400: 40% Water: 60% at 10 mg/ml for a total of 4 weeks. Results are expressed as mean tumor volume±SE. To assess differences in tumor size between groups, a Mann-Whitney non-parametric t test was performed and significance was assessed for p values<0.05. Tumor size was evaluated periodically during treatment at the indicated days post-inoculation. Results are represented as the mean of tumor volume in mm$^3$±SE of several tumors (n=10) in function of the treatment period. Significant reductions in tumor growth were observed in groups treated with well-tolerated doses of 6.25 or 12.5 mg/kg of N-(3-amino-propyl)-3-chloro-N-[(R)-O-(7-chloro-4-oxo-3-phenylamino-3,4-dihydro-quinazolin-2-yl)-but-3-ynyl]-2-fluoro-benzamide on PACA-2 xenograft model compared to the vehicle control group. (See FIG. 1A).

Example 107

In Vivo Data

Figure 1B:
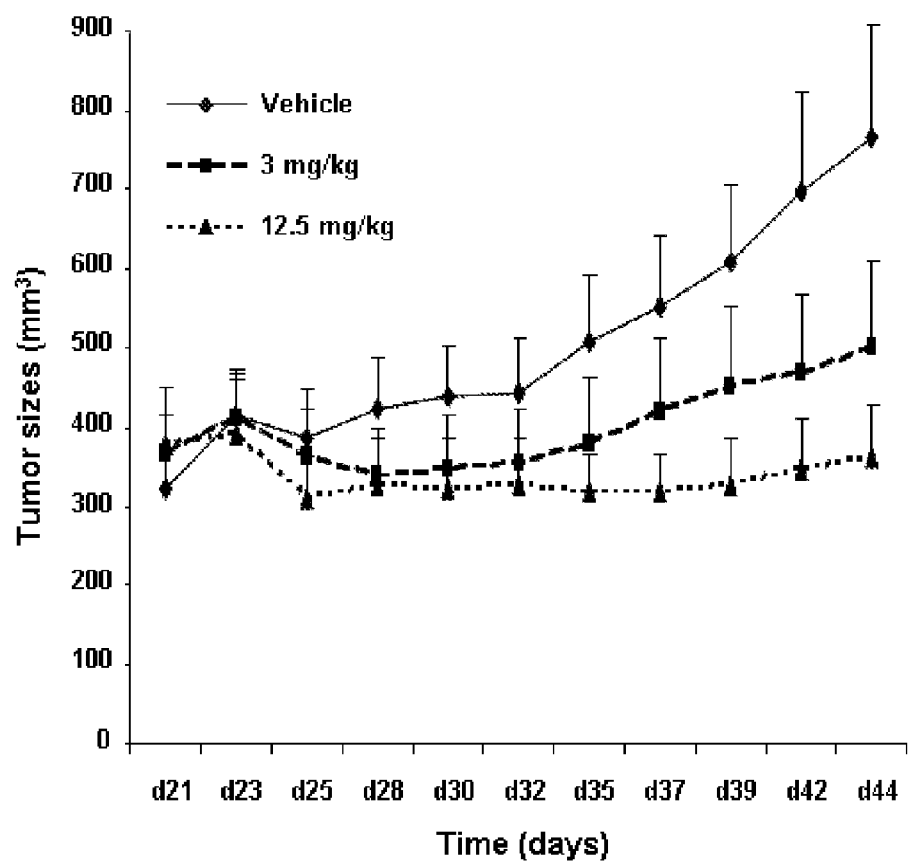

Six weeks old female athymic nude mice (NCR nu/nu) received from Charles River Laboratory, acclimated to the animal housing facility for one week before initiation of the study. Mice were housed in sterile cages of 4 each with autoclaved bedding, provided with autoclaved food and water ad libitum. Efficacy studies were performed in athymic mice bearing PACA2 tumor xenografts to determine the effect of compound on tumor growth. Tumor cells ($1 \times 10^7$ PACA2 cells/animal) were inoculated subcutaneously on day 0. Tumor dimensions were measured three times weekly by a digital microcaliper, and tumor volumes were calculated as length×width$^2$/2. When tumors reached a volume of ~300 mm$^3$, mice were randomized into groups and treated 3× weekly (Monday-Wednesday-Friday, followed by a 2-day dosing holiday) intraperitoneally. With either vehicle control or 3 mg/kg and 12.5 mg/kg compound formulated in DMA/PEG400/water (20:40:40). Results are expressed as mean tumor volume±SE. To assess differences in tumor size between groups, student's t test was performed and significance was assessed for p values<0.05. Tumor size was evaluated periodically during treatment at the indicated days post-inoculation. Results are represented as the mean of tumor volume in mm$^3$±SE of several tumors (n=10) in function of the treatment period. Significant reductions in tumor growth were observed in groups treated with well-tolerated doses of 3 mg/kg or 12.5 mg/kg of N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide on PACA-2 xenograft model compared to the vehicle control group. (See FIG. 1B).

Example 108

In Vivo Data

Figure 2:
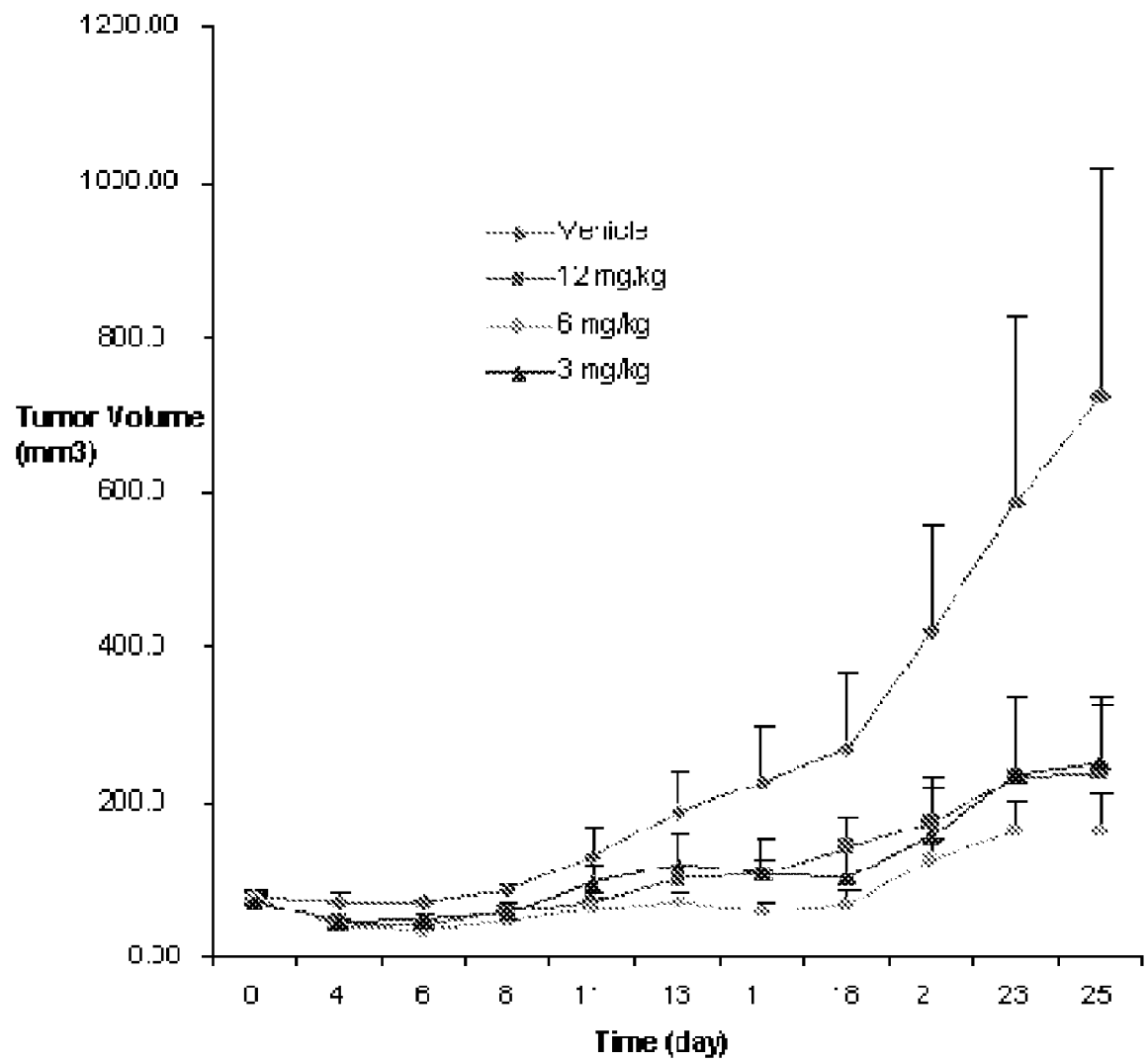
FIG. 2 shows the effect of N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide on MDA-MB-231 xenograft model.

Six weeks old female athymic nude mice (NCR nu/nu) received from Charles River Laboratory, acclimated to the animal housing facility for one week before initiation of the study. Mice were housed in sterile cages of 4 each with autoclaved bedding, provided with autoclaved food and water ad libitum. Efficacy studies were performed in athymic mice bearing MDA-MB-231 tumor xenografts to determine the effect of compound on tumor growth. Tumor cells ($5 \times 10^6$ MDA-MB-231 cells/animal) were inoculated subcutaneously on day 0. Tumor dimensions were measured three times weekly by a digital microcaliper, and tumor volumes were calculated as length×width$^2$/2. When tumors reached a volume of ~100 mm$^3$, mice were randomized into groups and treated 3× weekly (Monday-Wednesday-Friday, followed by a 2-day dosing holiday) intraperitoneally. With either vehicle control or 3 mg/kg, 6 mg/kg and 12 mg/kg compound formulated in DMA/PEG400/water (4:8:88). Results are expressed as mean tumor volume±SE. To assess differences in tumor size between groups, student's t test was performed and significance was assessed for p values<0.05. Tumor size was evaluated periodically during treatment at the indicated days post-inoculation. Results are represented as the mean of tumor volume in mm$^3$±SE of several tumors (n=8) in function of the treatment period. Significant reductions in tumor growth were observed in groups treated with well-tolerated doses of 3 mg/kg, 6 mg/kg or 12 mg/kg of N-(3-amino-propyl)-3-chloro-N-[(R)-1-(7-chloro-4-oxo-3-phenylamino-3,4-dihydro-quinazolin-2-yl)-but-3-ynyl]-2-fluoro-benzamide on MDA-MB-231 xenograft model compared to the vehicle control group (See FIG. 2).

Other embodiments are within the following claims. While several embodiments have been shown and described, various modifications may be made without departing from the spirit and scope of the present invention.

What is claimed is:
1. A compound of formula I, or pharmaceutically acceptable salts thereof:

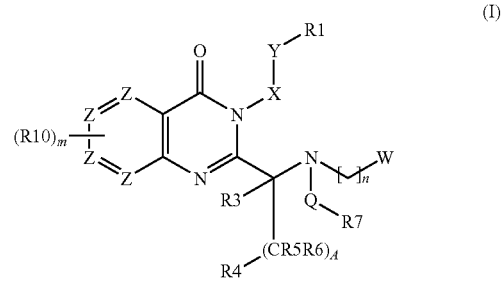

(I)

Wherein
m, n and A are independently selected from the group consisting of 0, 1, 2, 3, and 4;
R1 is selected from the group consisting of H, alkyl, aryl, haloaryl, and fluoroaryl;
Y is selected from the group consisting of a bond;
X is selected from the group consisting of NR2, O, and S;
R2 is selected from the group consisting of hydrogen, alkyl including lower alkyl, alkenyl, and alkynyl;
R3 is selected from H, alkyl, alkenyl, and alkynyl;
R4 is selected from H, alkyl, aryl, substituted aryl, heteroaryl, alkenyl, alkynyl, and S-alkyl;
Each R5 and each R6 are independently selected from the group consisting of H, halogen, hydroxyl, nitrogen, amino, cyano, alkoxy, alkylthio, methylenedioxy, or haloalkyloxy; or alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido;

Q is either absent or selected from the group consisting of —CO—, and —SO$_2$—;

R7 is selected from the group consisting of aryl, alkylaryl, heteroaryl, aryl substituted with one or more of alkyl, halogen, —NO$_2$, alkyloxy, and heterocycles;

W is selected from H or NR8R9; where R8 and R9 are independently selected from the group consisting of hydrogen, alkyl, aryl, heteroaryl, alkenyl, akynyl, COR13, —CO$_2$R13, —CONR14R14, —SOR13, —SO$_2$R13, —C(=S)R14, —C(=NH)R14, and —C(=S)NR14R15; or R8 and R9 together with the N they are bonded to optionally form a heterocycle or substituted heterocycle;

Each Z is C—R10:

Each R10 is independently selected from the group consisting of hydrogen, halogen, hydroxyl, nitro, amino, cyano, alkoxy, alkylthio, methylenedioxy, or haloalkyloxy; alkyl, alkenyl, alkynyl, aryl, substituted aryl, heteroaryl, alkylamino, dialkylamino, alkylsulfonyl, arylsulfonyl, alkylcarboxy, carboxyamino, carboxyamido, aminocarbonyl, and alkylsulfonamido; and R11, R12, R13, R14, and R15 are independently selected from the group consisting of hydrogen, alkyl, aryl, alkylaryl, heteroaryl, oxaalkyl, oxaalkylaryl, and substituted oxaalkylaryl.

2. The compound of claim 1 wherein A is 0, 1, or 2.

3. The compound of claim 2, wherein A is 1 or 2 and R5 and R6 are independently selected from the group consisting of H, halogen, hydroxyl, nitrogen, amino, cyano, alkoxy, alkylthio, methylenedioxy, or haloalkyloxy; or alkyl, alkenyl, alkynyl, aryl, heteroaryl, alkylamino, dialkylamino, alkylsulfonyl, arylsulfonyl, alkylcarboxy, carboxyamino, carboxyamido, aminocarbonyl, and alkylsulfonamido.

4. The compound of claim 1 wherein A is 1, and R5 and R6 are H.

5. The compound of claim 1 wherein m is 1.

6. The compound of claim 1 wherein n is 3.

7. The compound of claim 1 wherein n is 2.

8. The compound of claim 1 wherein R8 and R9 are H.

9. The compound of claim 1 wherein X is NR2.

10. The compound of claim 1 wherein X is NH.

11. The compound of claim 1 wherein X is O or S.

12. The compound of claim 1 wherein R1 is phenyl.

13. The compound of claim 1 wherein R2 is H.

14. The compound of claim 1 wherein R3 is H.

15. The compound of claim 1 wherein R4 is ethynyl, methyl, ethyl, propyl, propynyl, butynyl, or tert-butyl.

16. The compound of claim 1 wherein R5 and R6 are H.

17. The compound of claim 1 wherein Q is CO.

18. The compound of claim 1 wherein R7 is unsubstituted or substituted phenyl.

19. The compound of claim 1 wherein W is H.

20. The compound of claim 17 wherein R8 and R9 are H.

21. The compound of claim 1 wherein the compound is (R)-N-(3-Amino-propyl)-3-chloro-N-[1-(7-chloro-4-oxo-3-phenylamino-3,4-dihydro-quinazolin-2-yl)-but-3-ynyl]-2-fluoro-benzamide.

22. A pharmaceutical composition comprising a compound of claim 1 in combination with a pharmaceutically acceptable carrier or excipient.

23. The compound of claim 1 wherein stereochemistry is of "R" configuration.

24. The compound of claim 1 wherein the compound is N-(3-Amino-propyl)-3-chloro-N-[1-(7-chloro-4-oxo-3-phenylamino-3,4-dihydro-quinazolin-2-yl)-but-3-ynyl]-2-fluoro-benzamide.

25. A pharmaceutical composition comprising a compound of claim 21 in combination with a pharmaceutically acceptable carrier or excipient.

26. A pharmaceutical composition comprising a compound of claim 24 in combination with a pharmaceutically acceptable carrier or excipient.

* * * * *